(12) United States Patent
Conroy et al.

(10) Patent No.: US 12,065,475 B2
(45) Date of Patent: Aug. 20, 2024

(54) T CELL RECEPTORS AND FUSION PROTEINS THEREOF

(71) Applicant: Immunocore Ltd, Abingdon (GB)

(72) Inventors: Paul Conroy, Abingdon (GB); Stephen Hearty, Abingdon (GB); Lok Hang Mak, Abingdon (GB)

(73) Assignee: Immunocore Ltd, Abingdon (GB)

( * ) Notice: Subject to any disclaimer, the term of this patent is extended or adjusted under 35 U.S.C. 154(b) by 0 days.

(21) Appl. No.: 18/542,441

(22) Filed: Dec. 15, 2023

(65) Prior Publication Data

US 2024/0109950 A1    Apr. 4, 2024

Related U.S. Application Data

(63) Continuation of application No. 18/451,415, filed on Aug. 17, 2023.

(60) Provisional application No. 63/399,095, filed on Aug. 18, 2022.

(51) Int. Cl.
| | | |
|---|---|---|
| *A61P 35/00* | (2006.01) | |
| *C07K 14/725* | (2006.01) | |
| *C12N 15/63* | (2006.01) | |

(52) U.S. Cl.
CPC .......... *C07K 14/7051* (2013.01); *A61P 35/00* (2018.01); *C12N 15/63* (2013.01); *C07K 2317/52* (2013.01); *C07K 2317/565* (2013.01); *C07K 2317/622* (2013.01); *C07K 2319/30* (2013.01)

(58) Field of Classification Search
CPC ....................................... A61P 35/00
USPC ....................................... 424/134.1
See application file for complete search history.

(56) References Cited

U.S. PATENT DOCUMENTS

| | | |
|---|---|---|
| 4,816,567 A | 3/1989 | Cabilly |
| 5,500,362 A | 3/1996 | Robinson |
| 5,545,806 A | 8/1996 | Lonberg |
| 5,545,807 A | 8/1996 | Surani |
| 5,569,825 A | 10/1996 | Lonberg |
| 5,591,828 A | 1/1997 | Bosslet |
| 5,625,126 A | 4/1997 | Lonberg |
| 5,633,425 A | 5/1997 | Lonberg |
| 5,641,870 A | 6/1997 | Rinderknecht |
| 5,661,016 A | 8/1997 | Lonberg |
| 5,731,168 A | 3/1998 | Carter |
| 5,807,706 A | 9/1998 | Carter |
| 5,821,333 A | 10/1998 | Carter |
| 5,821,337 A | 10/1998 | Carter |
| 5,959,177 A | 9/1999 | Hein |
| 6,040,498 A | 3/2000 | Stomp |
| 6,075,181 A | 6/2000 | Kucherlapati |
| 6,150,584 A | 11/2000 | Kucherlapati |
| 6,417,429 B1 | 7/2002 | Hein |
| 6,420,548 B1 | 7/2002 | Vezina |
| 6,982,321 B2 | 1/2006 | Winter |
| 7,087,409 B2 | 8/2006 | Barbas, III |
| 7,125,978 B1 | 10/2006 | Vezina |
| 7,642,228 B2 | 1/2010 | Carter |
| 7,695,936 B2 | 4/2010 | Carter |
| 8,216,805 B2 | 7/2012 | Carter |
| 11,505,590 B2 | 11/2022 | Hayes et al. |
| 2007/0082362 A1 | 4/2007 | Jakobsen |
| 2009/0214551 A1 | 8/2009 | Jakobsen |
| 2009/0324566 A1 | 12/2009 | Shiku |
| 2013/0089553 A1 | 4/2013 | Carter |
| 2013/0109053 A1 | 5/2013 | Macdonald |
| 2014/0371085 A1 | 12/2014 | Jakobsen |
| 2014/0378389 A1 | 12/2014 | Robbins |
| 2019/0092834 A1* | 3/2019 | Hayes .................... C07K 16/30 |
| 2023/0322895 A1 | 10/2023 | Hayes et al. |
| 2024/0092859 A1 | 3/2024 | Conroy |

FOREIGN PATENT DOCUMENTS

| | | |
|---|---|---|
| CO | 20170010502 A2 | 1/2018 |
| CO | 20180010453 A2 | 10/2018 |
| CO | 20180010811 A2 | 10/2018 |
| EP | 0404097 B1 | 9/1996 |
| WO | 199110741 A1 | 7/1991 |
| WO | 199311161 A1 | 6/1993 |
| WO | 199633735 A1 | 10/1996 |
| WO | 199634096 A1 | 10/1996 |
| WO | 199824893 A2 | 6/1998 |
| WO | 199839482 A1 | 9/1998 |
| WO | 199918129 A1 | 4/1999 |
| WO | 2000020445 A2 | 4/2000 |
| WO | 2000020445 A3 | 7/2000 |
| WO | 200148145 A2 | 7/2001 |

(Continued)

OTHER PUBLICATIONS

Aleksic, M. et al. (2012). "Different Affinity Windows For Virus And Cancer-Specific T-Cell Receptors: Implications For Therapeutic Strategies," Eu J Immunol. 42(12): 3174-3179.

Altschul, S.F. et al. (Oct. 5, 1990). "Basic Local Alignment Search Tool," J. Mol. Biol. 215(3):403-410.

Altschul, S.F. et al. (Sep. 1, 1997). "Gapped BLAST and PSI-BLAST: A New Generation of Protein Database Search Programs," Nucleic Acids Res. 25(17):3389-3402.

Arstila, T.P. et al. (Oct. 29, 1999). "A Direct Estimate Of The Human αβ T Cell Receptor Diversity," Science 286 (5441):958-961.

(Continued)

*Primary Examiner* — Sean E Aeder
(74) *Attorney, Agent, or Firm* — Morrison & Foerster LLP

(57) ABSTRACT

The present disclosure provides T cell receptor (TCR) fusion proteins comprising a TCR that binds to a GVYDGREHTV (SEQ ID NO:34) HLA-A*02 complex that is covalently linked to a T cell engaging domain that binds a protein expressed on a cell surface of a T cell and an antibody Fc domain, as well as polynucleotides, vectors, kits, host cells, pharmaceutical compositions, methods, and uses related thereto.

21 Claims, 20 Drawing Sheets

Specification includes a Sequence Listing.

(56) References Cited

FOREIGN PATENT DOCUMENTS

| WO | 200162908 | A2 | 8/2001 |
|---|---|---|---|
| WO | 200148145 | A3 | 1/2002 |
| WO | 2003020763 | A2 | 3/2003 |
| WO | 2003020763 | A3 | 5/2003 |
| WO | 2004023973 | A2 | 3/2004 |
| WO | 2004033685 | A1 | 4/2004 |
| WO | 2004042072 | A2 | 5/2004 |
| WO | 2004023973 | A3 | 9/2004 |
| WO | 2004074322 | A1 | 9/2004 |
| WO | 2004092219 | A2 | 10/2004 |
| WO | 2005100402 | A1 | 10/2005 |
| WO | 2006029879 | A2 | 3/2006 |
| WO | 2010133828 | A1 | 11/2010 |
| WO | 2013053021 | A1 | 4/2013 |
| WO | 2014096803 | A1 | 6/2014 |
| WO | 2014118236 | A2 | 8/2014 |
| WO | 2014118236 | A3 | 10/2014 |
| WO | 2014160030 | A2 | 10/2014 |
| WO | 2014160030 | A3 | 11/2014 |
| WO | 2016007570 | A2 | 1/2016 |
| WO | 2016022400 | A1 | 2/2016 |
| WO | 2016007570 | A3 | 3/2016 |
| WO | 2017175006 | A1 | 10/2017 |
| WO | 2020157211 | A1 | 8/2020 |
| WO | 2023099606 | | 6/2023 |

OTHER PUBLICATIONS

Barbas III, C.F. et al. (Apr. 1994). "In Vitro Evolution Of A Neutralizing Human Antibody To Human Immunodeficiency Virus Type 1 To Enhance Affinity and Broaden Strain Cross-Reactivity," Proc Nat. Acad. Sci. USA 91:3809-3813.

Bedouelle, H. et al. (Jan. 2006). "Diversity and Junction Residues As Hotspots of Binding Energy In an Antibody Neutralizing The Dengue Virus," FEBS J. 273(1):34-46.

Bergeron, A. et al. (2009, e-pub. Apr. 14, 2009). "High Frequency Of MAGE-A4 and MAGE-A9 Expression In High-Risk Bladder Cancer," Int J Cancer 125(6): 1365-1371.

Boerner, P. et al. (Jul. 1, 1991). "Production of Antigen-Specific Human Monoclonal Antibodies from In Vitro-Primed Human Splenocytes," J. Immunol. 147(1):86-95.

Bossi, G. (May 2014, e-pub. Feb. 15, 2014). "ImmTAC-Redirected Tumour Cell Killing Induces and Potentiates Antigen Cross-Presentation By Dendritic Cells," Cancer Immunology, Immunotherapy 63(5):437-448.

Bossi, G. et al. (Nov. 2013). "Examining The Presentation Of Tumor-Associated Antigens On Peptide-Pulsed T2 Cells," Oncolummunology 2(11): e26840, 7 pages.

Boulter, J.M. et al. (2003). "Stable, Soluble T-Cell Receptor Molecules For Crystallization and Therapeutics," Protein Eng 16(9):707-711.

Bragado, R. et al. (1994). "Allelic Polymorphism in the Coding Region of Human TCR C Alpha Gene and Characterization of Structural variability in the Alpha Chain Constant Domain," International Immunology 6(2):223-230.

Brown, M. et al. (May 1, 1996). "Tolerance of Single, But Not Multiple, Amino Acid Replacements in Antibody VH CDR 2: A Means of Minimizing B Cell Wastage From Somatic Hypermutation?," J. Immunol. 156(9):3285-3291.

Brüggemann, M. et al. (1993). "Designer Mice: The Production of Human Antibody Repertoires in Transgenic Animals," Year in Immunol. 7:33-40.

Brüggemann, M. et al. (Nov. 1, 1987). "Comparison of the Effector Functions of Human Immunoglobulins Using a Matched Set of Chimeric Antibodies," J. Exp. Med. 166:1351-1361.

Cabezón, T et al. (2013). "Proteomic Profiling of Triple-Negative Breast Carcinomas in Combination With a Three-tier Orthogonal Technology Approach Identifies Mage-A4 as Potential Therapeutic Target in Estrogen Receptor Negative Breast Cancer," Mol Cell Proteomics 12(2):381-394.

Cameron, B.J et al. (Aug. 7, 2013). "Identification of a Titin-Derived HLA-A1-Presented Peptide As A Cross-Reactive Target For Engineered MAGE A3-Directed T Cells," Sci Trans Med. 5(197): 197ra103, 24 pages.

Capel, P.J.A. et al. (Feb. 1994). "Heterogeneity of Human IgG Fc Receptors," Immunomethods 4(1):25-34.

Cat. No. MHC-LC1146 "APC-A*02:01/Human MAGEA4 (GVYDGREHTV) MHC Tetramer," retrieved from https://www.creativebiolabs.net/pdf/MHC-LC1146.pdf, 2 pages.

Chen, X. et al. (Oct. 15, 2013). "Fusion Protein Linkers: Property, Design and Functionality," Advanced Drug Delivery Reviews 65(10): 1357-1369, 32 pages.

Chervin, A.S. et al. (Dec. 31, 2008). "Engineering Higher Affinity T Cell Receptors Using A T Cell Display System," J. Immuno. Methods 339(2): 175-184, 21 pages.

Chothia, C. (1976). "The Nature of the Accessible and Buried Surfaces in Proteins," J. Mol. Biol. 105:1-14.

Chothia, C. et al. (Aug. 20, 1987). "Canonical Structures for the Hypervariable Regions of Immunoglobulins," J. Mol. Biol. 196(4): 901-917.

Clackson, T. et al. (Aug. 15, 1991). "Making Antibody Fragments Using Phage Display Libraries," Nature 352:624-628.

Clynes, R. et al. (Jan. 1998). "Fc Receptors are Required in Passive and Active Immunity to Melanoma," Proc. Natl. Acad. Sci. USA 95:652-656.

Cole, S.P.C. et al. (1985). "The EBV-Hybridoma Technique and Its Application to Human Lung Cancer," in Monoclonal Antibodies and Cancer Therapy, Alan R. Liss, p. 77-96.

Colman, P.M. (1994). "Effects Of Amino Acid Sequence Changes On Antibody-Antigen Interactions," Research in Immunology 145(1):33-36.

Cragg, M.S. et al. (Apr. 1, 2004, e-pub. Oct. 9, 2003). "Antibody Specificity Controls In Vivo Effector Mechanisms Of Anti-CD20 Reagents," Blood 103(7):2738-2743, 7 pages.

Cragg, M.S. et al. (Feb. 1, 2003). "Complement-Mediated Lysis By Anti-CD20 Mab Correlates With Segregation Into Lipid Rafts," Blood 101(3): 1045-1052.

Cuffel, C. et al. (2011). "Pattern and Clinical Significance Of Cancer-Testis Gene Expression In Head and Neck Squamous Cell Carcinoma," Int J Cancer 128(11): 2625-2634.

Cunha-Neto, E. (Feb. 1999). "MHC-Restricted Antigen Presentation and Recognition: Constraints On Gene, Recombinant and Peptide Vaccines In Humans," Brazilian Journal of Medical and Biological Research 32:199-205.

Davis, M.M. et al. (Apr. 1998). "Ligand Recognition By αβ T Cell Receptors," Annu Rev Immunol 16:(15):523-544.

Daëron, M. (1997). "Fc Receptor Biology," Ann. Rev. Immunol. 15:203-234.

De Haas, M. et al. (1995). "Fcγ Receptors of Phagocytes," J. Lab. Clin. Med. 126(4):330-341.

De La Hera, A. et al. (1991). "Structure of the T Cell Antigen Receptor (TCR): Two CD3 Epsilon Subunits in a Functional TCR/CD3 Complex," The Journal of Experimental Medicine 173(1):7-17.

De Plaen, E. et al. (1994). "Structure, Chromosomal Localization, and Expression Of 12 Genes Of The MAGE Family," Immunogenetics 40(5):360-369.

Dennis, M.S. et al. (Sep. 20, 2002). "Albumin Binding as a General Strategy for Improving the Pharmacokinetics of Proteins," J Biol Chem. 277(38): 35035-35043.

Devereux, J. et al. (1984). "A Comprehensive Set Of Sequence Analysis Programs For The VAX," Nucleic Acids Research 12(1): 387-395.

Dolgin, E. (Mar. 24, 2022). "First Soluble TCR Therapy Opens 'New Universe' if Cancer Targets," Nature Biotechnology 40(4): 441-444.

Dozier, J.K. et al. (Oct. 28, 2015). "Site-Specific PEGylation of Therapeutic Proteins," Int J Mol Sci. 16 (10):25831-25864.

Duffour, M.-T. et al. (1999). "A MAGE-A4 Peptide Presented By HLA-A2 Is Recognized By Cytolytic T Lymphocytes," Eur J Immunol 29(10):3329-3337.

(56) References Cited

OTHER PUBLICATIONS

Epel, M. et al. (Nov. 2002, e-pub. Sep. 13, 2002). "A Functional Recombinant Single-Chain T Cell Receptor Fragment Capable Of Selectively Targeting Antigen-Presenting Cells," Cancer Immunol Immunother. 51 (10):565-573.

Fellouse, F.A. et al. (Aug. 24, 2004). "Synthetic Antibodies From a Four-Amino-Acid Code: A Dominant Role for Tyrosine in Antigen Recognition," Proc. Natl. Acad. Sci. USA 101(34): 12467-12472.

Fishwild, D.M. et al. (Jul. 1996). "High-Avidity Human IgGK Monoclonal Antibodies from a Novel Strain of Minilocus Transgenic Mice," Nature Biotechnol. 14:845-851.

Folch, G. et al. (2000). "The Human T Cell Receptor Beta Diversity (TRBD) and Beta Joining (TRBJ) Genes," Exp Clin Immunogenet 17(2):107-114.

Folch, G. et al. (2000). "The Human T cell Receptor Beta Variable (TRBV) Genes," Exp Clin Immunogenet 17 (1): 42-54.

Forghanifard, M.M. et al. (Aug. 1, 2011). "Cancer-Testis Gene Expression Profiling In Esophageal Squamous Cell Carcinoma: Identification Of Specific Tumor Marker And Potential Targets For Immunotherapy," Cancer Biol Ther 12(3): 191-197.

Garboczi, D.N. et al. (Apr. 1992). "HLA-A2-Peptide Complexes: Refolding and Crystallization Of Molecules Expressed In *Escherichia coli* and Complexed With Single Antigenic Peptides," Proc Natl Acad Sci USA 89 (8):3429-3433.

Gasser, B. et al. (Feb. 2007). "Antibody Production With Yeasts and Filamentous Fungi: On the Road to Large Scale?," Biotechnology Letters 29(2):201-212.

Gazzano-Santoro, H. et al. (1997). "A Non-Radioactive Complement-Dependent Cytotoxicity Assay for Anti-CD20 Monoclonal Antibody," J. Immunol. Methods 202:163-171.

Ghetie, V. et al. (Dec. 1997). "FcRn: the MHC Class I-Related Receptor That Is More Than An IgG Transporter," Immunol. Today 18(12):592-598, 7 pages.

Ghetie, V. et al. (Jul. 1997). "Increasing the Serum Persistence of an IgG Fragment by Random Mutagenesis," Nat Biotech 15:637-640.

Graham, F. L. et al. (Jul. 1977). "Characteristics of a Human Cell Line Transformed by DNA from Human Adenovirus Type 5," J Gen Virol. 36(1): 59-72.

Guyer, R.L. et al. (Aug. 1976). "Immunoglobulin Binding By Mouse Intestinal Epithelial Cell Receptors," J. Immunol. 117(2):587-593.

Hamers-Casterman, C. et al. (Jun. 3, 1993). "Naturally Occurring Antibodies Devoid of Light Chains," Nature 363:446-448.

Hammerling, G.J. et al. (1981). "Production of Antibody-Producing Hybridomas in the Rodent System," Chapter 12, in Monoclonal Antibodies and T-Cell Hybridomas, Elsevier/North Holland Biomedical Press, New York, pp. 563-587, 14 pages.

Harris, W.J. (1995). "Production of Humanized Monoclonal and Antibodies for in vivo Imaging and Therapy," Biochem. Soc. Transactions 23:1035-1038.

Hawkins, R.E. et al. (1992). "Selection of Phage Antibodies by Binding Affinity: Mimicking Affinity Maturations," J. Mol. Biol. 226:889-896.

Hellstrom, I. et al. (Mar. 1985). "Strong Antitumor Activities of IgG3 Antibodies to a Human Melanoma-Associated Ganglioside," Proc. Natl. Acad. Sci. USA 82:1499-1502.

Hellstrom, I. et al. (Sep. 1986). "Antitumor Effects of L6, an IgG2a Antibody That Reacts With Most Human Carcinomas," Proc. Natl. Acad. Sci. USA 83:7059-7063.

Hinton, P.R. et al. (Feb. 20, 2004). "Engineered Human IgG Antibodies with Longer Serum Half-lives in Primates," J. Biol. Chem. 279(8):6213-6216.

Holler, P.D. et al. (May 9, 2000). "In vitro Evolution Of A T Cell Receptor With High Affinity For Peptide/MHC," Proc Natl Acad Sci USA 97(10):5387-5392.

Holliger, P. et al. (Jul. 1993), "Diabodies': Small Bivalent and Bispecific Antibody Fragments," Proc. Natl. Acad. Sci. USA 90:6444-6448.

Hongo, J.A.S. et al. (1995). "Development and Characterization of Murine Monoclonal Antibodies to the Latency-Associated Peptide of Transforming Growth Factor Beta1," Hybridoma 14(3):253-260.

Hoogenboom, H.R. et al. (Sep. 20, 1992). "By-Passing Immunisation. Human Antibodies From Synthetic Repertoires of Germline VH Gene Segments Rearranged in Vitro," J. Mol. Biol. 227:381-388.

Hurle, M.R. et al. (1994). "Protein Engineering Techniques for Antibody Humanization," Curr. Op. Biotech. 5:428-433.

Inaguma, Y. et al. (Jun. 2014, e-pub. Apr. 3, 2014). "Construction and Molecular Characterization of a T-Cell Receptor-Like Antibody and CAR-T Cells Specific For Minor Histocompatibility Antigen HA-1H," Gene Therapy 21 (6):575-584.

International Preliminary Report on Patentability, issued Oct. 9, 2018, for PCT Application No. PCT/GB2017/050985, filed Apr. 7, 2017, 7 pages.

International Search Report and Written Opinion mailed on Nov. 6, 2023, for PCT Application No. PCT/EP2023/072739, filed on Aug. 17, 2023, 16 pages.

International Search Report and Written Opinion of the International Search Authority, mailed Jun. 19, 2017, for PCT Application No. PCT/GB2017/050985, filed Apr. 7, 2017, 14 pages.

Jackson, J.R. et al. (Apr. 1, 1995). "In Vitro Antibody Maturation. Improvement Of A High Affinity, Neutralizing Antibody Against IL-1 Beta," J. Immunol. 154(7):3310-3319.

Jakobovits, A. et al. (Mar. 18, 1993). "Germ-Line Transmission and Expression of a Human-Derived Yeast Artificial Chromosome," Nature 362:255-258.

Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90:2551-2555.

Jefferis, R. (Mar. 2009). "Glycosylation As A Strategy To Improve Antibody-Based Therapeutics," Nat Rev Drug Discov 8(3): 226-234.

Jevsevar, S. et al. (Jan. 2010). "PEGylation Of Therapeutic Proteins," Biotechnol J. 5(1): 113-128, 52 pages.

Johnson, G. et al. (2003). "The Kabat Database and a Bioinformatics Example," Chapter 2 in Methods in Molecular Biology, Lo, B.K.C, Humana Press, Totawa, N.J., 248: 11-25.

Jones, P.T. et al. (May 29, 1986). "Replacing the Complementarity-Determining Regions in a Human Antibody With Those From a Mouse," Nature 321:522-525.

June, C.H. et al. (Sep. 2014). "Engineered T Cells For Cancer Therapy," Cancer Immunol Immunother 63 (9):969-975, 11 pages.

Karimi, S. et al. (May 2012). "Characterization of Melanoma-Associated Antigen-A Genes Family Differential Expression in Non-Small-Cell Lung Cancers," Clin Lung Cancer 13(3):214-219.

Karlin, S. et al. (Jun. 1993). "Applications and Statistics For Multiple High-Scoring Segments In Molecular Sequences," Proc. Natl. Acad. Sci. USA 90:5873-5877.

Karlin, S. et al. (Mar. 1990). "Methods For Assessing The Statistical Significance Of Molecular Sequence Features By Using General Scoring Schemes," Proc. Natl. Acad. Sci. USA 87(6):2264-2268.

Kim, J-K. et al. (Apr. 1994). "Localization of the Site of the Murine IgGI Molecule That is Involved in Binding to the Murine Intestinal Fc Receptor," Eur. J. Immunol. 24:2429-2434.

Kohler, G. et al. (Aug. 7, 1975). "Continuous Culture of Fused Cells Secreting Antibody of Predefined Specificity," Nature 256:495-497.

Kuball, J. et al. (Feb. 16, 2009). "Increasing Functional Avidity of TCR-Redirected T Cells by removing Defined N-Glycosylation Sited in the TCR Constant Domain," Journal of Experimental Medicine 206(2):463-475.

Lee, C.V. et al. (2004). "Bivalent Antibody Phage Display Mimics Natural Immunoglobulin," J. Immunol. Methods 284 (1-2):119-132.

Lee, C.V. et al. (2004). "High-affinity Human Antibodies From Phage-displayed Synthetic Fab Libraries With a Single Framework Scaffold," J. Mol. Biol. 340(5): 1073-1093.

Lefranc, M.P. (2003). "IMGT® Databases, Web Resources And Tools For Immunoglobulin and T Cell Receptor Sequence Analysis, http://imgt.cines.fr," Leukemia 17(1):260-266.

(56) References Cited

OTHER PUBLICATIONS

Li, J. et al. (Mar. 7, 2006). "Human Antibodies for Immunotherapy Development Generated Via a Human B Cell Hybridoma Technology," Proc. Natl. Acad. Sci. USA 103(10):3557-3562.
Li, Y. et al. (Mar. 2005, e-pub. Feb. 20, 2005). "Directed Evolution Of Human T-Cell Receptors With Picomolar Affinities By Phage Display," Nat Biotechnol. 23(3): 349-354.
Liddy, N. et al. (Jun. 2012). "Monoclonal TCR-Redirected Tumor Cell Killing," Nat Med 18(6):980-987.
Lissin, N.M. et al. (2013). "Chapter 32—High-Affinity Monoclonal T-Cell Receptor (mTCR) Fusions," Fusion Protein Technologies for Biopharmaceuticals: Applications and Challenges, 11 pages.
Lonberg, N. et al. (1995, e-pub. Jul. 10, 2009). "Human Antibodies From Transgenic Mice," Int. Rev. Immunol. 13 (1):65-93.
Lonberg, N. et al. (Apr. 28, 1994). "Antigen-Specific Human Antibodies From Mice Comprising Four Distinct Genetic Modifications," Nature 368(6474): 856-859.
Maeda, Y. et al. (Jul. 1, 1997). "Engineering of Functional Chimeric Protein G-Vargula Luciferase," Analytical Biochemistry 249(2): 147-152.
Marks, J.D. et al. (1991). "By-Passing Immunization: Human Antibodies From V-Genen Libraries Displayed on Phage," J. Mol. Biol. 222:581-597.
Marks, J.D. et al. (Jul. 1992). "By-Passing Immunization: Building High Affinity Human Antibodies by Chain Shuffling," Bio/Technology 10:779-783.
Mather, J.P. et al. (1980). "Establishment and Characterization Of Two Distinct Mouse Testicular Epithelial Cell Lines," Biology of Reproduction 23:243-252.
Mather, J.P. et al. (1982). "Culture of Testicular Cells in Hormone-Supplemented Serum-Free Medium," Annals New York Academy of Sciences pp. 44-68.
Maus, M.V. et al. (Jul. 2013). "T Cells Expressing Chimeric Antigen Receptors Can Cause Anaphylaxis in Humans," Cancer Immunology Research 1(1):26-31.
Morrison, S.L. (Apr. 28, 1994). "Success in Specification," Nature 368:812-813.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.
Muller, S. et al. (Dec. 2008). "Spliceosomal Peptide P140 for Immunotherapy of Systemic Lupus Erthematosus: Results of an Early Phase II Clinical Trial." Arthritis & Rheumatism: Offical Journal of the American College of Rheumatology 58(12): 3783-3883.
Mullis, K.B. et al. (1994). PCR: The Polymerase Chain Reaction, Mullis et al. eds., Birkauswer Press, Boston, 5 pages.
Myers, E.W. et al. (Mar. 1988). "Optimal Alignments in Liner Space," CABIOS 4(1): 11-17.
Nazarov, V.I. (2015). "Review of Analysis Methods, Generation Models and Repertoire Selection Models Immune Receptor," New Information Technology in Automated Systems 18:270-280. English Abstract.
Neuberger, M. (Jul. 1996). "Generating High-Avidity Human Mabs in Mice," Nature Biotechnology 14:826.
Non-Final Office Action, mailed Mar. 3, 2022, for U.S. Appl. No. 16/092,174, filed Oct. 8, 2018, 13 pages.
O'Callaghan, C.A et al. (1999). "BirA Enzyme: Production and Application in the Study of Membrane Receptor ±Ligand Interactions by Site-Specific Biotinylation," Anal Biochem 266(1):9-15.
Oates, M.E. et al. (2013, e-pub. Nov. 29, 2012). "$D^2P^2$: Database Of Disordered Protein Predictions," Nucleic Acids Res. 41(D1): D508-D516.
Pearson, W.R. et al. (Apr. 1988). "Improved Tools For Biological Sequence Comparison," Proc. Natl. Acad. Sci. USA 85(8): 2444-2448.
Petkova, S.B. et al. (2006, e-pub. Oct. 31, 2006). "Enhanced Half-Life of Genetically Engineered Human IgG1 Antibodies in a Humanized FcRn Mouse Model: Potential Application in Humorally Mediated Autoimmune Disease," Int'l. Immunol. 18(12): 1759-1769.
Plückthun, A. (1994). "Antibodies from *Escherichia Coli*," in Chapter 11 The Pharmacology of Monoclonal Antibodies, vol. 113, Rosenburg and Moore eds., Springer-Verlag, New York, pp. 269-315, 48 pages.
Presta, L.G. (1992). "Antibody Engineering," Current Opinion in Structural Biology 2:593-596.
Purbhoo. M.A et al. (2006). "Quantifying and Imaging NY-ESO-1/LAGE-1-Derived Epitopes on Tumor Cells Using High Affinity T Cell Receptors," J Immunol 176(12):7308-7316.
Rashtchian, A. (Feb. 1995). "Novel Methods For Cloning and Engineering Genes Using The Polymerase Chain Reaction," Curr Opin Biotechnol 6(1):30-36.
Ravetch, J.V. et al. (1991). "Fc Receptors," Annu. Rev. Immunol. 9:457-492.
Riechmann, L. et al. (Mar. 24, 1988). "Reshaping Human Antibodies for Therapy," Nature 332:323-327.
Robbins, P.F. et al. (2008). "Single and Dual Amino Acid Substitutions in TCR CDRs Can Enhance Antigen-Specific T Cell Functions," J Immunol. 180:6116-6131.
Robins, H.S. et al. (Nov. 5, 2009, e-pub. Aug. 25, 2009). "Comprehensive Assessment of T-cell Receptor β-Chain Diversity In αβ T Cells," Blood 114(19):4099-4107, 10 pages.
Robins, H.S. et al. (Nov. 5, 2009, e-pub. Aug. 25, 2009). "Comprehensive Assessment Of T-Cell Receptor β-Chain Diversity In αβ T Cells," Blood 114(19):4099-4107, 20 pages.
Rosenberg, S.A. et al. (Apr. 2008). "Adoptive Cell Transfer: A Clinical Path To Effective Cancer Immunotherapy," Nat Rev Cancer 8(4):299-308, 22 pages.
Rudikoff, S. et al. (Mar. 1982). "Single Amino Acid Substitution Altering Antigen-Binding Specificity," Proc. Natl. Acad. Sci. USA 79:1979-1983.
Sambrook, J. et al. (1989). Molecular Cloning—A Laboratory Manual, 2nd Edition, Maniatis, T.(ed.) et al., Cold Spring Harbor Laboratory Press, New York, NY pp. v-xxxii, 28 pages, (Table of Contents only).
Sambrook, J. et al. (2001). Molecular Cloning: A Laboratory Manual Cold Spring Harbor Laboratory Press, Cold Spring Harbor, N.Y., 3rd ed., 1 page, Table of Contents.
Scaviner, D. et al. (2000). "The Human T Cell Receptor Alpha Joining (TRAJ) Genes," Exp Clin Immunogenet 17 (2):97-106.
Scaviner, D. et al. (2000). "The Human T Cell Receptor Alpha Variable (TRAV) Genes," Exp Clin Immunogenet 17 (2):83-96.
Schellenberger, V. et al. (Dec. 2009, e-pub. Nov. 15, 2009). "A Recombinant Polypeptide Extends The in vivo Half-Life Of Peptides And Proteins In A Tunable Manner," Nat Biotechnol. 27(12): 1186-1190, 8 pages.
Schier, R. et al. (1995). "Identification of Functional and Structural Amino-Acid Residues by Parsimonious Mutagenesis," Gene 169:147-155.
Schlapschy, M. et al. (Aug. 2013, e-pub. Jun. 10, 2013). "PASylation: A Biological Alternative To PEGylation For Extending The Plasma Half-Life Of Pharmaceutically Active Proteins," Protein Eng Des Sel. 26(8): 489-501.
Schodin, B.A. et al. (Jun. 1996). "Binding Properties And Solubility Of Single-Chain T Cell Receptors Expressed In *E. Coli*," Mol Immunol 33(9): 819-829.
Sheriff, S. et al. (Sep. 1996). "Redefining the Minimal Antigen-Binding Fragment," Nature Struct. Biol. 3 (9):733-736.
Shields, R.L. et al. (Mar. 2, 2001). "High Resolution Mapping of the Binding Site on Human IgG1 for FcγRI, FcγRII. FcγRIII, and FcRn and Design of IgG1 Variants With Improved Binding to the FcγR," J. Biol. Chem. 276(9):6591-6604.
Sidhu, S.S. et al. (2004). "Phage-Displayed Antibody Libraries Synthetic Heavy Chain Complementarity Determining Regions," J. Mol. Biol. 338(2):299-310.
Sinclair, A.M. et al. (Aug. 2005). "Glycoengineering: The Effect Of Glycosylation On The Properties Of Therapeutic Proteins," Pharm Sci. 94(8): 1626-1635.
Singapore Written Opinion; dated Jan. 9, 2020, for Singapore Patent Application No. 11201808797X, filed Apr. 7, 2017, 6 pages.

(56) References Cited

OTHER PUBLICATIONS

Soo Hoo et al., "Characterization of a single-chain T-cell receptor expressed in *Escherichia coli*," Proc Natl Acad Sci USA. (1992) 89(10): 4759-4763.

Spiess, C. et al. (Aug. 2013, e-pub. Jul. 7, 2013). "Bispecific Antibodies With Natural Architecture Produced by Co-Culture of Bacteria Expressing Two Distinct Half-Antibodies," Nature Biotech. 31(8):753-758.

Stites, D.P. et al. (1994). "Immunoglobulin Protiens," Chapter 6 in Basic Clinical Immunology, 8th Edition, Appleton & Lange, Norwalk, CT, pp. 66-79.

Strohl, W.R. (2009). "Optimization of Fc-mediated effector functions of monoclonal antibodies," Curr Opin Biotechnol. 20(6):685-691.

Svobodová, S. et al. (Feb. 2011. E-pub. Nov. 4, 2010). "Cancer-Testis Antigen Expression In Primary Cutaneous Melanoma Has Independent Prognostic Value Comparable To That Of Breslow Thickness, Ulceration and Mitotic Rate," Eur J Cancer 47(3):460-469.

Teplyakov, A. et al. (2014, e-pub. Mar. 31, 2014). "Antibody Modeling Assessment II. Structures and Models," Proteins: Structure, Function, and Bioinformatics 82(8): 1563-1582.

Torelli, A. et al. (Feb. 1994). "ADVANCE and ADAM: Two Algorithms For The Analysis Of Global Similarity Between Homologous Informational Sequences," Comput. Appl. Biosci. 10(1):3-5.

Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.

Vajdos, F.F. et al. (2002). "Comprehensive Functional Maps of the Antigen Binding Site of an Anti-ErbB2 Antibody Obtained with Shotgun Scanning Mutagenesis," J. Mol. Biol. 320:415-428.

Van Dijk, M.A. et al. (Aug. 2001). "Human Antibodies as Next Generation Therapeutics," Curr. Opin. Che. Biology 5(4): 368-374.

Vaswani, S.K. et al. (Aug. 1998). "Humanized Antibodies as Potential Therapeutic Drugs," Ann. Allergy, Asthma & Immunol. 1:105-115.

Weidanz, J.A. et al. (Dec. 1, 1998). "Display Of Functional αβ Single-Chain T-Cell Receptor Molecules On The Surface Of Bacteriophage," J Immunol Methods. 221(1-2):59-76.

Willuda, J. et al. (Apr. 2001). "Tumor Targeting of Mono-, Di-, and Tetravalent Anti-p185HER-2 Miniantibodies Multimerized by Self-associating Peptides," J. Biol. Chem. 276(17): 14385-14392.

Wilson, D.B. et al. (Feb. 2004). "Specificity and Degeneracy Of T Cells," Mol Immunol 40(14-15): 1047-1055.

Wooldridge, L. et al. (Jan. 6, 2012). "A Single Autoimmune T Cell Receptor Recognizes More Than a Million Different Peptides," J Biol Chem 287(2):1168-1177.

Xu, J.L. et al. (Jul. 2000). "Diversity in the CDR3 Region of VH is Sufficient for Most Antibody Specificities," Immunity 13:37-45.

Yakirevich, E. et al. (Dec. 15, 2003). "Expression MAGE-A4 and NY-ESO_1 Cancer-Testis Antigens in Serous Ovarian Neoplasms," Clinical Cancer Research 9(17):6453-6460.

Yazaki, P.J. et al. (2003). "Expression of Recombinant Antibodies in Mammalian Cell Lines," Methods in Molecular Biology 248:255-268.

Yelton, D.E. et al. (1995). "Affinity Maturation of the BR96 Anti-Carcinoma Antibody by Codon-Based Mutagenesis," J. Immunol. 155:1994-2004.

Zamyatnin, A.A. (1972). "Protein Volume In Solution," Prog. Biophys. Mol. Biol. 24:107-123.

Zapata, G. et al. (1995). "Engineering Linear F(ab')2 Fragments for Efficient Production in *Escherichia coli* and Enhanced Antiproliferative Activity," Protein Eng. 8(10): 1057-1062.

Zhao, Y. et al. (2007). "High-Affinity TCRs Generated by Phage Display Provide CD4+ T Cells with the Ability to Recognize and Kill Tumor Cell Lines," J. Immunol, 179(9): 5845-5854.

\* cited by examiner

| Dose level | Monoglycosylated | | Aglycosylated | |
| --- | --- | --- | --- | --- |
| | T1/2 | Clearance (ml/hr/Kg) | T1/2 | Clearance (ml/hr/Kg) |
| 665 ug/Kg | 7.2d ± 0.7 | 0.357 ± 0.016 | 3.5d +/- 0.04 | 0.703 ± 0.062 |
| 66.5 ug/Kg | 7.1d ± 0.4 | 0.375 ± 0.048 | 3.6d +/- 0.08 | 0.822 ± 0.095 |
| 6.65 ug/Kg | 5.5d ± 1.4 | 0.457 ± 0.025 | 3.5d +/- 0.16 | 0.888 ± 0.085 |

FIG. 3E

| Cell line | Indication | GVYDGREHTY (average copies/cell) | MAGE-A4 RNA expression (TCGA RPKM) | MAGE-A4 RNA expression (Average of norm counts/normalization by RNA) | HLA-A2 surface (ratio A2/isotype) | *Killing EC50 (pM) mono/aglyc | TFNγ EC50 (pM) mono/aglyc |
|---|---|---|---|---|---|---|---|
| NCI-H1755 | Lung Adenocarcinoma | 4374 | 2767.5 | 8314387 | 73.1 | 2.40/1.48 | 38.6/30.6 |
| NCI-H1703 | Lung Adenocarcinoma | 1171 | 1626.7 | 3467762 | 89.5 | <0.43/<0.41 | 164.7/153.1 |
| SCaBER | Bladder Urothelial Carcinoma | 951 | 801.7 | 2460440 | 104.4 | 70.2/61.7 | 69.4/54.0 |
| H314 | Squamous cell carcinoma | 180 | Not available | 530067 | 73.2 | 113.9/108.5 | 94.0/97.2 |
| UM-UC-3 | Bladder Urothelial Carcinoma | 167 | 414.6 | 1902791 | 65.4 | ?/? | 313.6/525.9 |

FIG. 4A

T CELL RECEPTORS AND FUSION PROTEINS THEREOF

CROSS-REFERENCE TO RELATED APPLICATIONS

This application is a continuation of U.S. Non-Provisional application Ser. No. 18/451,415, filed Aug. 17, 2023, which claims the priority benefit of U.S. Provisional Application Ser. No. 63/399,095, filed Aug. 18, 2022, each of which is incorporated herein by reference in its entirety.

REFERENCE TO AN ELECTRONIC SEQUENCE LISTING

The contents of the electronic sequence listing (146392054101seqlist.xml; Size: 35,722 bytes; and Date of Creation: Nov. 29, 2023) are incorporated herein by reference in their entirety.

FIELD

The present disclosure relates to T cell receptor (TCR) fusion proteins comprising a TCR that binds to a GVYDGREHTV (SEQ ID NO:34) HLA-A*02 complex that is covalently linked to an antigen-binding domain that binds a protein expressed on a cell surface of a T cell and an antibody Fc domain, as well as related polynucleotides, vectors, kits, host cells, pharmaceutical compositions, methods, and uses.

BACKGROUND

T cell receptors (TCRs) are naturally expressed by CD4+ and CD8+ T cells. TCRs are designed to recognize short peptide antigens that are displayed on the surface of antigen presenting cells in complex with Major Histocompatibility Complex (MHC) molecules (in humans, MHC molecules are also known as Human Leukocyte Antigens, or HLA) (Davis, et al., (1998), Annu Rev Immunol 16: 523-544.). CD8+ T cells, which are also termed cytotoxic T cells, specifically recognize peptides bound to MHC class I and are generally responsible for finding and mediating the destruction of diseased cells. CD8+ T cells are able to destroy cancerous as well as virally infected cells; however, the affinity of TCRs expressed by cancer specific T cells in the natural repertoire are typically low as a result of thymic selection, meaning that cancerous cells frequently escape detection and destruction. Novel immunotherapeutic approaches aimed at promoting cancer recognition by T cells offer a highly promising strategy for the development of effective anticancer treatments.

MAGE A4 belongs to the MAGE family of germline encoded cancer antigens (De Plaen, et al., (1994), Immunogenetics 40(5): 360-369) and has the Uniprot accession number P43358. Such antigens have been found to be frequently expressed in a variety of cancers, while their expression in normal tissues is limited to adult testes and other immune-privileged sites including placenta. The cancer specific nature of these genes makes them ideal targets for anti-cancer therapeutics. The precise function of MAGE A4 remains unknown but it is believed to play a role in embryonic development. High level expression of MAGE A4 has been reported in tumours of several types including melanoma, carcinomas of the esophagus, the head and neck, the lung, the breast and the bladder (Bergeron, (2009), Int J Cancer 125(6): 1365-1371; Cabezon, et al., (2013), Mol Cell Proteomics 12(2): 381-394; Cuffel, et al., (2011), Int J Cancer 128(11): 2625-2634; Forghanifard, et al., (2011), Cancer Biol Ther 12(3): 191-197; Karimi, et al., (2012), Clin Lung Cancer 13(3): 214-219; Svobodova, et al., (2011), Eur J Cancer 47(3): 460-469). The 10-mer peptide GVYDGREHTV (SEQ ID NO: 34) corresponds to amino acids 230-239 of the full length MAGE A4 protein. This peptide binds to HLA-A*02 and the peptide-HLA complex has been shown to stimulate cytotoxic T cells leading to lysis of MAGE A4 positive, HLA-A*02 positive, tumour cells (Duffour, et al., (1999), Eur J Immunol 29(10): 3329-3337 and WO2000020445). A GVYDGREHTV (SEQ ID NO:34) HLA-A*02 complex therefore provides a useful target antigen for immunotherapeutic intervention.

Soluble TCRs and TCR fusion proteins that bind a GVYDGREHTV (SEQ ID NO:34) HLA-A*02 complex are described, e.g., in US PG Pub. No. US20190092834 and International Pub. No. WO2017175006. However, there remains a need for TCR fusion proteins that bind the MAGE A4 peptide:HLA complex with favorable properties, such as stability, binding affinity, cell-killing potency, and/or in vivo pharmacokinetics.

All references cited herein, including patent applications and publications, are incorporated by reference in their entirety.

SUMMARY

In certain aspects, provided herein is a T cell receptor (TCR) fusion protein comprising a TCR that binds to a GVYDGREHTV (SEQ ID NO:34) HLA-A*02 complex, wherein the TCR is a soluble TCR that is covalently linked to: (1) a T cell engaging domain that binds a protein expressed on a cell surface of a T cell, and (2) an antibody Fc domain; wherein the TCR comprises: (a) a TCR alpha chain comprising an alpha chain variable region, wherein the alpha chain variable region comprises (i) a CDR1 comprising the amino acid sequence of VSPFSN (SEQ ID NO:1), (ii) a CDR2 comprising the amino acid sequence of LTFSENT (SEQ ID NO:2), and (iii) a CDR3 comprising the amino acid sequence of VVNSAQGLYIPTF (SEQ ID NO:3); and (b) a TCR beta chain comprising a beta chain variable region, wherein the beta chain variable region comprises (i) a CDR1 comprising the amino acid sequence of LDHEN (SEQ ID NO:4), (ii) a CDR2 comprising the amino acid sequence of SRFATG (SEQ ID NO:5), and (iii) a CDR3 comprising the amino acid sequence of ASSSDQNSGDPYEQYF (SEQ ID NO:6); wherein the TCR is glycosylated at a single N-linked glycosylation site, wherein the N-linked glycosylation site is at residue N18 of the alpha chain variable region, numbering according to SEQ ID NO:7.

In some embodiments according to any of the embodiments described herein, the TCR comprises an amino acid substitution at every potential N-glycosylation site other than residue N18. In some embodiments, the TCR comprises amino acid substitutions at: (a) residue N24 of the alpha chain variable region, numbering according SEQ ID NO:32; (b) residues N33, N67, and N78 of the alpha chain constant region, numbering according to SEQ ID NO:10; (c) residue N84 of the beta chain variable region, numbering according SEQ ID NO:33; and (d) residue N70 of the beta chain constant region, numbering according SEQ ID NO:15. In some embodiments, the amino acid substitutions are N→Q. In some embodiments, the TCR comprises the following amino acid substitutions: (a) N24Q in the alpha chain variable region, numbering according SEQ ID NO:32; (b)

N33Q, N67Q, and N78Q in the alpha chain constant region, numbering according to SEQ ID NO:10; (c) N84Q in the beta chain variable region, numbering according SEQ ID NO:33; and (d) N70Q in the beta chain constant region, numbering according SEQ ID NO:15.

In some embodiments according to any of the embodiments described herein, the TCR comprises one or more engineered cysteine residues in the alpha and/or beta chain constant region to form a non-native disulfide bond between the alpha and beta chains. In some embodiments, the TCR comprises a cysteine residue at position 57 of the beta chain constant region, numbering according to SEQ ID NO:15.

In some embodiments according to any of the embodiments described herein, the alpha chain variable region comprises an amino acid sequence having at least 90%, at least 91%, at least 92%, at least 93%, at least 94%, at least 95%, at least 96%, at least 97%, at least 98%, at least 99%, or 100% identity to the amino acid sequence of SEQ ID NO:7. In some embodiments, the beta chain variable region comprises an amino acid sequence having at least 90%, at least 91%, at least 92%, at least 93%, at least 94%, at least 95%, at least 96%, at least 97%, at least 98%, at least 99%, or 100% identity to the amino acid sequence of SEQ ID NO:13. In some embodiments, the alpha chain variable region comprises the amino acid sequence of SEQ ID NO:7, and the beta chain variable region comprises the amino acid sequence of SEQ ID NO:13. In some embodiments, the TCR alpha chain further comprises an alpha chain constant region, and wherein the alpha chain constant region comprises an amino acid sequence having at least 90%, at least 91%, at least 92%, at least 93%, at least 94%, at least 95%, at least 96%, at least 97%, at least 98%, at least 99%, or 100% identity to the amino acid sequence of SEQ ID NO:9. In some embodiments, the TCR beta chain further comprises a beta chain constant region, and wherein the beta chain constant region comprises an amino acid sequence having at least 90%, at least 91%, at least 92%, at least 93%, at least 94%, at least 95%, at least 96%, at least 97%, at least 98%, at least 99%, or 100% identity to the amino acid sequence of SEQ ID NO:14. In some embodiments, the TCR alpha chain further comprises an alpha chain constant region comprising the amino acid sequence of SEQ ID NO:9, and the TCR beta chain further comprises a beta chain constant region comprising the amino acid sequence of SEQ ID NO:14. In some embodiments, the alpha chain comprises an amino acid sequence having at least 90%, at least 91%, at least 92%, at least 93%, at least 94%, at least 95%, at least 96%, at least 97%, at least 98%, at least 99%, or 100% identity to the amino acid sequence of SEQ ID NO:11. In some embodiments, the beta chain comprises an amino acid sequence having at least 90%, at least 91%, at least 92%, at least 93%, at least 94%, at least 95%, at least 96%, at least 97%, at least 98%, at least 99%, or 100% identity to the amino acid sequence of SEQ ID NO:16. In some embodiments, the alpha chain comprises the amino acid sequence of SEQ ID NO:11, and the beta chain comprises the amino acid sequence of SEQ ID NO:16.

In some embodiments according to any of the embodiments described herein, the antibody Fc domain is a human Fc domain. In some embodiments, the antibody Fc domain is a human IgG1, human IgG2, or human IgG4 Fc domain. In some embodiments, the antibody Fc domain comprises one or more mutations that attenuate an effector function of the Fc domain. In some embodiments, the antibody Fc domain is a human IgG1 Fc domain comprising a mutation at residue N297, numbering according to EU index. In some embodiments, the antibody Fc domain is a human IgG1 Fc domain comprising an N297G substitution, numbering according to EU index. In some embodiments, the antibody Fc domain is a human IgG1 Fc domain comprising one or more mutation(s) at residue(s) E233, L234, L235, and/or G236, numbering according to EU index. In some embodiments, the antibody Fc domain is a human IgG1 Fc domain comprising substitutions N297G, E233P, L234V, L235A, and a deletion at G236, numbering according to EU index. In some embodiments, the antibody Fc domain is a human IgG1 Fc domain comprising one or more mutation(s) at residue(s) L234, L235, and P329, numbering according to EU index. In some embodiments, the antibody Fc domain is a human IgG1 Fc domain comprising substitutions L234A, L235A, and P329G, numbering according to EU index. In some embodiments, the antibody Fc domain is fused to the TCR via a hinge sequence. In some embodiments, the hinge sequence comprises the amino acid sequence of DKTHTCPP (SEQ ID NO:31) or DKTHTCPPC (SEQ ID NO:36). In some embodiments, the TCR fusion protein further comprises a second antibody Fc domain, wherein the second antibody Fc domain is associated with the first antibody Fc domain via: (1) one or more covalent linkages; and/or (2) one or more amino acid substitutions on one or both of the antibody Fc domains that promote heterodimerization.

In some embodiments, the first and second antibody Fc domains both comprise antibody CH2 and CH3 domains. In some embodiments, the first antibody Fc domain is fused to the TCR via a first hinge sequence, and a second hinge sequence is linked to the N-terminus of the second antibody Fc domain. In some embodiments, the first and second hinge sequences are linked via one or more interchain disulfide bonds between the first and second hinge sequences. In some embodiments, the first and second hinge sequences both comprise the amino acid sequence of DKTHTCPP (SEQ ID NO:31) or DKTHTCPPC (SEQ ID NO:36). In some embodiments, one of the first and second antibody Fc domains comprises one or more knob-forming mutations and the other of the first and second antibody Fc domains comprises one or more corresponding hole-forming mutations to promote heterodimerization of the antibody Fc domains. In some embodiments, one of the first and second antibody Fc domains comprises a T366W substitution, and the other of the first and second antibody Fc domains comprises T366S, L368A, Y407V substitutions, numbering according to EU index. In some embodiments, one of the first and second antibody Fc domains comprises the amino acid sequence of SEQ ID NO:27, and the other of the first and second antibody Fc domains comprises the amino acid sequence of SEQ ID NO:26. In some embodiments, the first antibody Fc domain that is covalently linked to the TCR comprises the amino acid sequence of SEQ ID NO:27, and the second antibody Fc domain comprises the amino acid sequence of SEQ ID NO:26.

In some embodiments according to any of the embodiments described herein, the T cell engaging domain binds human CD3 expressed on the cell surface of a T cell. In some embodiments, the T cell engaging domain comprises an antibody antigen binding domain. In some embodiments, the T cell engaging domain (e.g., an antibody antigen binding domain) is a single chain variable fragment (scFv). In some embodiments, the scFv comprises the amino acid sequence of SEQ ID NO:17. In some embodiments, the scFv comprises the amino acid sequence of SEQ ID NO:35. In some embodiments, the T cell engaging domain is covalently linked to the TCR via linker. In some embodiments, the linker comprises an amino acid sequence selected from the group consisting of SEQ ID Nos:18-25. In some embodiments, the C-terminus of the T cell engaging domain is covalently linked to the N-terminus of the TCR beta chain variable domain. In some embodiments, the C-terminus of the T cell engaging domain is covalently linked to the N-terminus of the TCR beta chain variable domain via a further linker. In some embodiments, the linker comprises an amino acid sequence selected from the group consisting of SEQ ID Nos:18-25. In some embodiments, the N-terminus of the antibody Fc domain is covalently linked to the C-terminus of the TCR alpha chain constant domain. In some embodiments, the N-terminus of the antibody Fc domain is covalently linked to the C-terminus of the TCR alpha chain constant domain via a hinge sequence. In some embodiments, the TCR fusion comprises three polypeptides comprising: (a) a first polypeptide comprising, from N-terminus to C-terminus: the TCR alpha chain variable region, an alpha chain constant region, a first hinge sequence, and a first antibody Fc domain; (b) a second polypeptide comprising, from N-terminus to C-terminus: a single chain variable fragment (scFv) that binds human CD3 expressed on the cell surface of a T cell, a linker, the beta chain variable region, and a beta chain constant region; and (c) a third polypeptide comprising, from N-terminus to C-terminus: a second hinge sequence and a second antibody Fc domain. In some embodiments, the first and second polypeptides are linked via one or more disulfide bonds between the alpha and beta chain constant regions. In some embodiments, the first and third polypeptides are linked via: (1) one or more interchain disulfide bonds between the first and second hinge sequences; and/or (2) one or more corresponding knob-forming and hole-forming mutations on the antibody Fc domains. In some embodiments, the first polypeptide comprises the amino acid sequence of SEQ ID NO:29, wherein the second polypeptide comprises the amino acid sequence of SEQ ID NO:30, and wherein the third polypeptide comprises the amino acid sequence of SEQ ID NO:28.

In other aspects, provided herein is a T cell receptor (TCR) fusion protein comprising a first polypeptide comprising the amino acid sequence of SEQ ID NO:29, a second polypeptide comprising the amino acid sequence of SEQ ID NO:30, and a third polypeptide comprising the amino acid sequence of SEQ ID NO:28.

In other aspects, provided herein are polynucleotides encoding the TCR fusion protein according to any one of the above embodiments. Further provided herein is a kit of polynucleotides comprising a first polynucleotide encoding a first polypeptide according to any one of the above embodiments, a second polynucleotide encoding a second polypeptide according to any one of the above embodiments, and a third polynucleotide encoding a third polypeptide according to any one of the above embodiments. In other aspects, provided herein are vectors comprising the polynucleotide(s) according to any one of the above embodiments. Further provided herein is a kit of vectors comprising a first vector encoding a first polypeptide according to any one of the above embodiments, a second vector encoding a second polypeptide according to any one of the above embodiments, and a third vector encoding a third polypeptide according to any one of the above embodiments. In some embodiments, the vector(s) are expression vector(s).

In other aspects, provided herein are host cells comprising the polynucleotide(s), kit of polynucleotides, vector(s), or kit of vectors according to any one of the above embodiments. In some embodiments, the host cell is a mammalian cell. In some embodiments, the mammalian cell is a Chinese hamster ovary (CHO) cell.

In other aspects, provided herein are methods of producing a TCR fusion protein, comprising culturing the host cell according to any one of the above embodiments under conditions suitable for production of the TCR fusion protein. In some embodiments, the methods further comprise recovering the TCR fusion protein from the host cell. Further provided herein are TCR fusion proteins produced by the method according to any one of the above embodiments.

In other aspects, provided herein are pharmaceutical compositions comprising the TCR fusion protein according to any one of the above embodiments and a pharmaceutically acceptable carrier.

In other aspects, provided herein are methods of treating cancer, comprising administering an effective amount of the TCR fusion protein according to any one of the above embodiments or the pharmaceutical composition according to any one of the above embodiments to an individual. Further provided herein is the TCR fusion protein according to any one of the above embodiments for use in medicine, preferably in a human subject. Further provided herein is the TCR fusion protein according to any one of the above embodiments for use in treating cancer, preferably in a human subject. Further provided herein is the use of the TCR fusion protein according to any one of the above embodiments in the manufacture of a medicament for treating cancer.

In some embodiments according to any of the embodiments described herein, the individual is a human. In some embodiments, the individual has a cancer that expresses MAGE-A4. In some embodiments, the individual is of HLA-A*02 subtype. In some embodiments, the TCR fusion protein or composition is administered intravenously or by intratumoral injection. In some embodiments, the methods further comprise administering to the individual a second anti-cancer agent.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 1B shows more detailed features, including knobs-into-holes (KIH) mutations to provide Fc heterodimerization (in this example, T366W on one chain and T366S/L368A/Y407V on the other), disulfide bonds in the hinge region, an engineered disulfide bond between the TCR alpha and beta chains, the TCR constant regions (Cα and Cβ on the alpha and beta chains, respectively), and the TCR variable regions (Vα and Vβ on the alpha and beta chains, respectively).

FIG. 2A shows a schematic representation of all 7 N-glycosylation sites on the TCR (left), as well as occupancy of each N-glycosylation site (right). FIG. 2B shows variant TCRs with sets of substitution mutations (e.g., N→Q) at various glycosylation sites, resulting in aglycosylated (left) or monoglycosylated (right) TCRs. Arrow indicates single remaining N-glycosylation site.

FIG. 2C shows that removing N-glycosylation sites (using N→Q substitutions) from TCR variable regions led to a significant reduction in yield, whereas removing N-glycosylation sites from the TCR constant regions did not affect yield. FIG. 2D shows that preserving N-glycosylation at residue N18 of the alpha chain variable region was the most critical site for boosting yield.

FIGS. 3A-3E show in vivo pharmacokinetic properties of TCR:anti-CD3 fusion molecules. FIG. 3A shows in vivo pharmacokinetic properties of various formats of TCR:anti-CD3 fusion molecules with or without an Fc domain, as indicated. FIG. 3B shows serum concentration over time of N297G control, aglycosylated, or monoglycosylated TCR:anti-CD3 fusion molecules having the indicated Fc format in a SCID mouse model. FIGS. 3C & 3D show serum concentration over time of monoglycosylated or aglycosylated (respectively) TCR:anti-CD3 fusion molecule shown in FIG. 3B in a SCID mouse model. FIG. 3E shows half-life and clearance of aglycosylated or monoglycosylated TCR:anti-CD3 fusion molecules shown in FIG. 3B administered at the indicated dose level.

FIGS. 4A-4D show potency and selectivity of aglycosylated or monoglycosylated TCR:anti-CD3 fusion molecules. FIG. 4A shows the name and type of each cell line, the average copy number and mRNA expression of MAGE-A4 of each cell line, HLA-A2 expression of each cell line, and observed EC50 for cell killing or IFNγ release upon treatment with monoglycosylated ("mono") or aglycosylated ("aglyc") TCR:anti-CD3 fusion molecule. **denotes that data were averaged from 3 different PBMC donors. FIGS. 4B-4D show % cytolysis over time of NCI-H1755 (FIG. 4B), SCaBER (FIG. 4C), or NCI-H441 (FIG. 4D) cell lines treated with aglycosylated or monoglycosylated TCR:anti-CD3 fusion molecules in the presence of effector cells. Values shown in FIGS. 4B-4D refer to lowest concentration of TCR:anti-CD3 fusion molecule observed to give rise to a killing response.

FIGS. 5A & 5B show potency of cell killing against NCI-H1755 (FIG. 5A) or A375 (FIG. 5B) cell lines mediated by TCR:anti-CD3 fusion molecule without Fc, TCR:anti-CD3 fusion molecule with Fc, and TCR:anti-CD3 fusion molecule with Fc and variant anti-CD3 scFv. FIG. 5C shows potency of cell killing against MAGE-A4+ NCI-H1755 cells vs. MAGE-A4− MEL202A2B2M cells, demonstrating the window between on-target and off-target activity.

FIG. 6A shows the results of testing the monoglycosylated TCR:anti-CD3 fusion molecule against a panel of normal cell lines, showing no detectable reactivity against normal cells. FIG. 6B shows the results of testing the TCR:anti-CD3 fusion molecule with variant anti-CD3 scFv and Fc domain against the same molecule without an Fc domain or variant scFv, demonstrating that the therapeutic window against on-target and off-target cells was maintained.

I. GENERAL TECHNIQUES

Figure 1A:
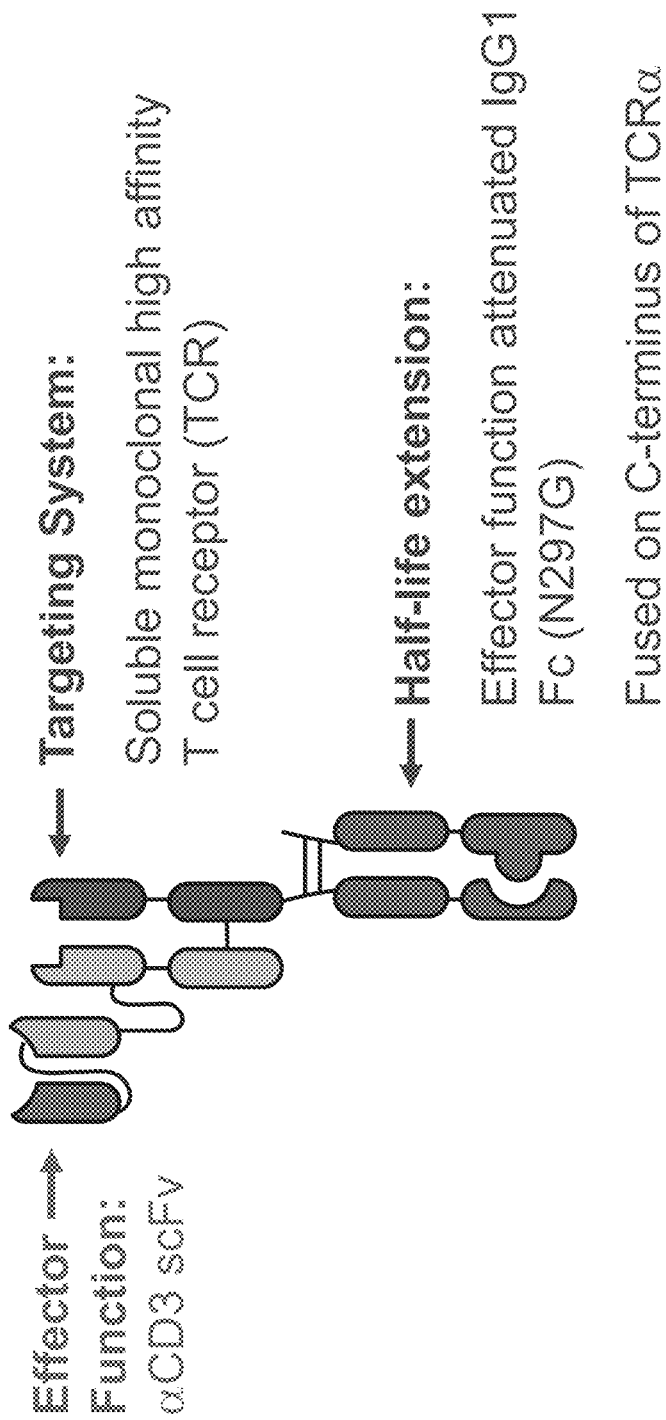
FIGS. 1A & 1B show schematic diagrams of a T-Cell Receptor (TCR):anti-CD3 fusion molecule, in accordance with some embodiments. In the example shown in FIG. 1A, effector function is provided by an anti-CD3 single chain variable fragment (scFv) fused to the N-terminus of the TCR beta chain, targeting is provided by a soluble monoclonal high-affinity TCR, and half-life extension in vivo is provided at least in part by an antibody Fc domain fused to the C-terminus of the TCR alpha chain (in this case, a human IgG1 Fc domain with N297G mutation).

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

II. DEFINITIONS

The TCR sequences defined herein are described with reference to IMGT nomenclature which is widely known and accessible to those working in the TCR field. For example, see: LeFranc and LeFranc, (2001). "T cell Receptor Factsbook", Academic Press; Lefranc, (201 1), Cold Spring Harb Protoc 201 1 (6): 595-603; Lefranc, (2001), Curr Protoc Immunol Appendix 1: Appendix 1O: and Lefranc, (2003), Leukemia 17(1): 260-266. Briefly, TCRs consist of two disulfide linked chains. Each chain (alpha and beta) is generally regarded as having two domains, namely a variable and a constant domain. A short joining region connects the variable and constant domains and is typically considered part of the alpha variable region. Additionally, the beta chain usually contains a short diversity region next to the joining region, which is also typically considered part of the beta variable region.

The variable domain of each chain is located N-terminally and comprises three Complementarity Determining Regions (CDRs) embedded in a framework sequence. The CDRs comprise the recognition site for peptide-MHC binding. There are several genes coding for alpha chain variable (Vα) regions and several genes coding for beta chain variable (Vβ) regions, which are distinguished by their framework, CDR1 and CDR2 sequences, and by a partly defined CDR3 sequence. The Vα and Vβ genes are referred to in IMGT nomenclature by the prefix TRAV and TRBV respectively (Folch and Lefranc, (2000), Exp Clin Immunogenet 17(1): 42-54; Scaviner and Lefranc, (2000), Exp Clin Immunogenet 17(2): 83-96; LeFranc and LeFranc, (2001), "T cell Receptor Factsbook", Academic Press). Likewise there are several joining or J genes, termed TRAJ or TRBJ, for the alpha and beta chain respectively, and for the beta chain, a diversity or D gene termed TRBD (Folch and Lefranc, (2000). Exp Clin Immunogenet 17(2): 107-1 14: Scaviner and Lefranc, (2000), Exp Clin Immunogenet 17(2): 97-106; LeFranc and LeFranc, (2001), "T cell Receptor Factsbook", Academic Press). The huge diversity of T cell receptor chains results from combinatorial rearrangements between the various V, J and D genes, which include allelic variants, and junctional diversity (Arstila, et al., (1999), Science 286(5441): 958-961; Robins et al., (2009), Blood 1 14(19): 4099-4107.) The constant, or C, regions of TCR alpha and beta chains are referred to as TRAC and TRBC respectively (Lefranc, (2001), Curr Protoc Immunol Appendix 1: Appendix 10).

"Engineered TCR" and "mutant TCR" are used synonymously herein to mean a TCR which has one or more mutations introduced relative to the native MAGE A4 TCR, in particular in the alpha chain variable domain and/or the beta chain variable domain thereof. Mutation(s) typically improve the binding affinity of the TCR to a GVYDGREHTV (SEQ ID NO: 34) HLA-A*02 complex, but may additionally or alternatively confer other advantages such as improved stability in an isolated form and improved specificity. Mutations at one or more positions may additionally or alternatively affect the interaction of an adjacent position with the cognate pMHC complex, for example by enabling a more favourable angle for interaction. To improve binding of the TCR to a GVYDGREHTV (SEQ ID NO: 34) HLA-A*02 complex, mutations are preferably made within one or more of the CDR regions.

Within the scope of the present disclosure are phenotypically silent variants of any TCR disclosed herein. As used herein the term "phenotypically silent variants" is understood to refer to a TCR which incorporates one or more further amino acid changes, including substitutions, insertions and deletions, in addition to those set out above, which TCR has a similar phenotype to the corresponding TCR without said change(s). For the purposes of this application, TCR phenotype comprises antigen binding affinity ($K_D$ and/or binding half-life) and antigen specificity. A phenotypically silent variant may have a $K_D$ and/or binding half-life for a GVYDGREHTV (SEQ ID NO: 34) HLA-A*02 complex within 50%, or more preferably within 20%, of the measured $K_D$ and/or binding half-life of the corresponding TCR without said change(s), when measured under identical conditions (for example at 25° C. and/or on the same SPR chip). As is known to those skilled in the art, it may be possible to produce TCRs that incorporate changes in the variable domains thereof compared to those detailed above without altering the affinity of the interaction with a GVYDGREHTV (SEQ ID NO:34) HLA-A*02 complex. In particular, such silent mutations may be incorporated within parts of the sequence that are known not to be directly involved in antigen binding (e.g. the CDRs, or parts of the CDRs that do not contact the peptide antigen). Such trivial variants are included in the scope of this disclosure.

Phenotypically silent variants may contain one or more conservative substitutions and/or one or more tolerated substitutions. Tolerated and conservative substitutions may result in a change in the $K_D$ and/or binding half-life for a GVYDGREHTV (SEQ ID NO: 34) HLA-A*02 complex within 50%, or more preferably within 20%, even more preferable within 10%, of the measured $K_D$ and/or binding half-life of the corresponding TCR without said conservative and/or tolerated substitution(s), when measured under identical conditions (for example at 25'C and/or the same SPR chip), provided that the change in $K_D$ does not result in the affinity being less than (i.e. weaker than) 200 µM. By tolerated substitutions it is meant those substitutions which do not fall under the definition of conservative as provided below but are nonetheless phenotypically silent.

The TCRs of the present disclosure may include one or more conservative substitutions which have a similar amino acid sequence and/or which retain the same function (i.e. are phenotypically silent as defined above). The skilled person is aware that various amino acids have similar properties and thus are 'conservative'. One or more such amino acids of a protein, polypeptide or peptide can often be substituted by one or more other such amino acids without eliminating a desired activity of that protein, polypeptide or peptide.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains): aspartate and glutamate (amino acids having acidic side chains); asparagine and glutamine (amino acids having amide side chains); and cysteine and methionine (amino acids having sulphur containing side chains). It should be appreciated that amino acid substitutions within the scope of the present disclosure can be made using naturally occurring or non-naturally occurring amino acids. For example, it is contemplated herein that the methyl group on an alanine may be replaced with an ethyl group, and/or that minor changes may be made to the peptide backbone. Whether or not natural or synthetic amino acids are used, it is preferred that only L-amino acids are present.

"Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984), BLASTP, BLASTN, and FASTA (Atschul et al., J. Molec. Biol. 215,403 (1990)).

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present disclosure.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The N BLAST and XBLAST programs of Altschul, et al. (1990) J. Mol. Biol. 215:403-410 have incorporated such an algorithm. BLAST nucleotide searches can be performed with the NBLAST program, score=100, wordlength=12 to obtain nucleotide sequences homologous to nucleic acid molecules. BLAST protein searches can be performed with the XBLAST program, score=50, wordlength=3 to obtain amino acid sequences homologous to protein molecules for use in the present disclosure. To obtain gapped alignments for comparison purposes, Gapped BLAST can be utilised as described in Altschul et al. (1997) Nucleic Acids Res. 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., XBLAST and NBLAST) can be used. See www.ncbi.nlm.nih.gov. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search.

Mutations, including conservation and tolerated substitutions, insertions and deletions, may be introduced into the sequences provided using any appropriate method including, but not limited to, those based on polymerase chain reaction (PCR), restriction enzyme-based cloning, or ligation independent cloning (LIC) procedures. These methods are detailed in many of the standard molecular biology texts.

The TCRs of the present disclosure may be as heterodimers. TCRs of the present disclosure may be in single chain format. Single chain formats include, but are not limited to, as TCR polypeptides of the Vα-L-Vβ, Vβ-L-Vα, Vα-Cα-L-Vβ, Vα-L-Vβ-Cβ, or Vα-Cα-L-Vβ-Cβ types, wherein Vα and Vβ are TCR α and β variable regions respectively, Cα and Cβ are TCR α and β constant regions respectively, and L is a linker sequence (Weidanz et al., (1998) J Immunol Methods. December 1; 221 (1-2):59-76; Epel et al., (2002), Cancer Immunol Immunother. November; 51 (10):565-73; WO 2004/033685; WO9918129). One or both of the constant domains may be full length, or they may be truncated as described above, and/or contain mutations. The alpha chain extracellular constant may have an asparagine (N) or a lysine (K) residue at position 4 due to a natural polymorphism. In certain embodiments single chain TCRs of the present disclosure may have an introduced disulfide bond between residues of the respective constant domains, as described in WO 2004/033685. Single chain TCRs are further described in WO2004/033685; WO98/39482; WO01/62908; Weidanz et al. (1998) J Immunol Methods 221 (1-2): 59-76; Hoo et al. (1992) Proc Natl Acad Sci USA 89(10): 4759-4763: Schodin (1996) Mol Immunol 33(9): 819-829).

The term "antibody" includes monoclonal antibodies (including full length antibodies which have an immunoglobulin Fc domain), antibody compositions with polyepitopic specificity, multispecific antibodies (e.g., bispecific antibodies, diabodies, and single-chain molecules, as well as antibody fragments (e.g., Fab, F(ab')$_2$, and Fv). The term "immunoglobulin" (Ig) is used interchangeably with "antibody" herein.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the a and 7 chains and four $C_H$ domains for p and F isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, C T, 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2A, IgG2B, IgG3, IgG4, IgA1 and IgA2.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, MD (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, the hybridoma method (e.g., Kohler and Milstein., *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2$^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically whole antibodies include those with heavy and light chains including an Fc domain. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10): 1057-1062 [1995]); single-chain antibody molecules and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain (V$_H$), and the first constant domain of one heavy chain (C$_H$1). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the C$_H$1 domain including one or more cysteines from the hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc domain, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the V$_H$ and V$_L$ antibody domains connected into a single polypeptide chain. Preferably, the sFv polypeptide further comprises a polypeptide linker between the V$_H$ and V$_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies of the invention comprise a portion of an intact antibody, generally including the antigen binding or variable region of the intact antibody or the Fc domain of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR are typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227: 381 (1991); Marks et al., *J. Mol. Biol.,* 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.,* 147(1):86-95 (1991). See also van Dijk and van de Winkel, *Curr. Opin. Pharmacol.,* 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N J, 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, MD. (1991)). Chothia refers instead to the location of the structural loops (Chothia and Lesk, J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, 5$^{th}$ Ed. Public Health Service, National Institutes of Health, Bethesda, MD (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

An "amino-acid modification" at a specified position, e.g. of the Fc domain, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and VL-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of $\leq 1$ µM, $\leq 100$ nM, $\leq 10$ nM, $\leq 1$ nM, or $\leq 0.1$ nM. In certain embodiments, an antibody specifically binds to an epitope on a protein that is conserved among the protein from different species. In another embodiment, specific binding can include, but does not require exclusive binding.

The term "Fc domain" herein is used to define a C-terminal region of an immunoglobulin heavy chain, including native-sequence Fc domains and variant Fc domains. Although the boundaries of the Fc domain of an immunoglobulin heavy chain might vary, the human IgG heavy-chain Fc domain is usually defined to stretch from an amino acid residue at position Cys226, or from Pro230, to the carboxyl-terminus thereof. The C-terminal lysine (residue 447 according to the EU numbering system) of the Fc domain may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc domains for use in the antibodies of the invention include human IgG1, IgG2 (IgG2A, IgG2B), IgG3 and IgG4.

"Fc receptor" or "FcR" describes a receptor that binds to the Fc domain of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus. Guyer et al., *J. Immunol.* 117: 587 (1976) and Kim et al., *J. Immunol.* 24: 249 (1994). Methods of measuring binding to FcRn are known (see, e.g., Ghetie and Ward, *Immunol. Today* 18: (12): 592-8 (1997); Ghetie et al., *Nature Biotechnology* 15 (7): 637-40 (1997); Hinton et al., *J. Biol. Chem.* 279 (8): 6213-6 (2004); WO 2004/92219 (Hinton et al.). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc domain are administered. WO 2004/42072 (Presta) describes antibody variants which improved or diminished binding to FcRs. See also, e.g., Shields et al., *J. Biol. Chem.* 9(2): 6591-6604 (2001).

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

A "package insert" refers to instructions customarily included in commercial packages of medicaments that contain information about the indications customarily included in commercial packages of medicaments that contain information about the indications, usage, dosage, administration, contraindications, other medicaments to be combined with the packaged product, and/or warnings concerning the use of such medicaments, etc.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

III. T CELL RECEPTORS AND FUSION PROTEINS

In one aspect, provided herein are TCR fusion proteins comprising a TCR that binds to a GVYDGREHTV (SEQ ID NO:34) HLA-A*02 complex. In some embodiments, the TCR is a soluble TCR. In some embodiments, the TCR fusion protein comprises a TCR of the present disclosure (e.g., a soluble monoclonal TCR) that is fused or linked to (e.g., covalently linked to) a T cell engaging domain that binds a protein expressed on a cell surface of a T cell, and an antibody Fc domain. In some embodiments, the TCR is glycosylated, e.g., at a single N-linked glycosylation site. In some embodiments, the N-linked glycosylation site is at residue N18 of the alpha chain variable region, e.g., numbering according to ANQVEQSPQSLII-LEGKNVTLQCQYTVSPFSNLRWYKQDT-GRGPVSLTILTFSENTKSNG RYTATLDADTKQSSLHITASQLSDSASYICVVNSAQG-LYIPTFGRGTSLIVHP (SEQ ID NO:7).

In some embodiments, the TCR comprises a TCR alpha chain comprising an alpha chain variable region and a TCR beta chain comprising a beta chain variable region. In some embodiments, the alpha chain variable region comprises (i) a CDR1 comprising the amino acid sequence of VSPFSN (SEQ ID NO:1), (ii) a CDR2 comprising the amino acid sequence of LTFSENT (SEQ ID NO:2), and (iii) a CDR3 comprising the amino acid sequence of VVNSAQGLYIPTF (SEQ ID NO:3) and/or the beta chain variable region comprises (i) a CDR1 comprising the amino acid sequence of LDHEN (SEQ ID NO:4), (ii) a CDR2 comprising the amino acid sequence of SRFATG (SEQ ID NO:5), and (iii) a CDR3 comprising the amino acid sequence of ASSSDQNSGDPYEQYF (SEQ ID NO:6).

As is well-known in the art, TCRs may be subject to post translational modifications. Glycosylation is one such modification, which comprises the covalent attachment of oligosaccharide moieties to defined amino acids in the TCR chain. For example, asparagine residues, or serine/threonine residues are well-known locations for oligosaccharide attachment. The glycosylation status of a particular protein depends on a number of factors, including protein sequence, protein conformation and the availability of certain enzymes. Furthermore, glycosylation status (i.e. oligosaccharide type, covalent linkage and total number of attachments) can influence protein function, Therefore, when producing recombinant proteins, controlling glycosylation is often desirable. Controlled glycosylation has been used to improve antibody based therapeutics. (Jefferis et al., (2009) Nat Rev Drug Discov March; 8(3):226-34.). For soluble TCRs of the present disclosure glycosylation may be controlled in vivo, by using particular cell lines for example, or in vitro, by chemical modification. Such modifications are desirable, since glycosylation can improve pharmacokinetics, reduce immunogenicity and more closely mimic a native human protein (Sinclair and Elliott, (2005) Pharm Sci. August; 94(8):1626-35).

In some embodiments, a TCR or TCR fusion protein of the present disclosure is glycosylated, e.g., at a single N-linked glycosylation site. In some embodiments, the N-linked glycosylation site is at residue N18 of the alpha chain variable region, e.g., numbering according to ANQVEQSPQSLII-
LEGKNVTLQCQYTVSPFSNLRWYKQDT-
GRGPVSLTILTFSENTKSNG RYTATLDADTKQSSLHI-
TASQLSDSASYICVVNSAQGLYIPTFGRGTSLIVHP
(SEQ ID NO:7). In some embodiments, a TCR fusion protein of the present disclosure comprises a TCR that is glycosylated at a single N-linked glycosylation site, wherein the N-linked glycosylation site is at residue N18 of the alpha chain variable region, numbering according to SEQ ID NO:7. Advantageously, the present disclosure demonstrates that TCR fusion proteins with this single glycosylated site have better manufacturability (e.g., protein production yield, resistance to thermal stress and aggregation) and in vivo pharmacokinetics (e.g., half-life), as compared to other glycosylated and/or aglycosylated variants, in addition to retaining affinity of peptide:MHC binding and potency of target cell killing.

In some embodiments, a TCR or TCR fusion protein of the present disclosure comprises an amino acid substitution at every potential N-glycosylation site other than residue N18. For example, in some embodiments, a TCR or TCR fusion protein of the present disclosure comprises amino acid substitution(s) at one or more of: residue N24 of the alpha chain variable region, numbering according SEQ ID NO:32; residues N33, N67, and N78 of the alpha chain constant region, numbering according to SEQ ID NO:10; residue N84 of the beta chain variable region, numbering according SEQ ID NO:33; and residue N70 of the beta chain constant region, numbering according SEQ ID NO:15. In some embodiments, a TCR or TCR fusion protein of the present disclosure comprises amino acid substitution(s) at all of: residue N24 of the alpha chain variable region, numbering according SEQ ID NO:32; residues N33, N67, and N78 of the alpha chain constant region, numbering according to SEQ ID NO:10; residue N84 of the beta chain variable region, numbering according SEQ ID NO:33; and residue N70 of the beta chain constant region, numbering according SEQ ID NO:15.

In some embodiments, the amino acid substitutions are asparagine to an amino acid that is not glycosylated. In some embodiments, the amino acid substitutions are asparagine to glutamine (N→Q).

In some embodiments, a TCR or TCR fusion protein of the present disclosure comprises one or more of the following amino acid substitutions: N24Q in the alpha chain variable region, numbering according SEQ ID NO:32; N33Q, N67Q, and N78Q in the alpha chain constant region, numbering according to SEQ ID NO:10; N84Q in the beta chain variable region, numbering according SEQ ID NO:33; and N70Q in the beta chain constant region, numbering according SEQ ID NO:15. In some embodiments, a TCR or TCR fusion protein of the present disclosure comprises all of the following amino acid substitutions: N24Q in the alpha chain variable region, numbering according SEQ ID NO:32; N33Q, N67Q, and N78Q in the alpha chain constant region, numbering according to SEQ ID NO:10; N84Q in the beta chain variable region, numbering according SEQ ID NO:33; and N70Q in the beta chain constant region, numbering according SEQ ID NO:15.

Alpha-beta heterodimeric TCRs of the present disclosure usually comprise an alpha chain TRAC constant domain sequence and/or a beta chain TRBC1 or TRBC2 constant domain sequence. The alpha and beta chain constant domain sequences may be modified by truncation or substitution to delete the native disulfide bond between Cys4 of exon 2 of TRAC and Cys2 of exon 2 of TRBC1 or TRBC2. The alpha and/or beta chain constant domain sequence(s) may be modified by substitution of cysteine residues for Thr 48 of TRAC and Ser 57 of TRBC1 or TRBC2, the said cysteines forming a disulfide bond between the alpha and beta constant domains of the TCR. TRBC1 or TRBC2 may additionally include a cysteine to alanine mutation at position 75 of the constant domain and an asparagine to aspartic acid mutation at position 89 of the constant domain. The constant domain may additionally or alternatively contain further mutations, substitutions or deletions relative to the native TRAC and/or TRBC1/2 sequences. The term TRAC and TRBC1/2 encompasses natural polymophic variants, for example N to K at position 4 of TRAC (Bragado et al Int Immunol. 1994 February; 6(2):223-30).

As will be obvious to those skilled in the art, it may be possible to truncate the sequences provided at the C-terminus and/or N-terminus thereof, by 1, 2, 3, 4, 5 or more residues, without substantially affecting the binding characteristics of the TCR. All such trivial variants are encompassed by the present disclosure.

The constant domain of a wild-type or non-soluble TCR may be full length, or may be truncated and/or mutated to produce a soluble TCR. In either case cysteine substitutions may be introduced into the TRAC and TRBC regions such that a non-native interchain disulfide bond can be formed. Suitable positions for the location of said cysteine substitutions are described in WO03020763.

In some embodiments, a TCR or TCR fusion protein of the present disclosure comprises one or more engineered cysteine residues in the alpha and/or beta chain constant region to form a non-native disulfide bond between the alpha and beta chains. In certain embodiments single chain TCRs of the present disclosure may have an introduced disulfide bond between residues of the respective constant domains, as described in WO 2004/033685. Single chain TCRs are further described in WO2004/033685; WO98/39482; WO01/62908; Weidanz et al. (1998) J Immunol Methods 221 (1-2): 59-76; Hoo et al. (1992) Proc Natl Acad Sci USA 89(10): 4759-4763; Schodin (1996) Mol Immunol 33(9): 819-829). In some embodiments, a TCR or TCR fusion protein of the present disclosure comprises a cysteine residue at position 57 of the beta chain constant region, numbering according to SEQ ID NO:15.

In some embodiments, a TCR or TCR fusion protein of the present disclosure comprises an alpha chain variable region that comprises an amino acid sequence having at least 90%, at least 91%, at least 92%, at least 93%, at least 94%, at least 95%, at least 96%, at least 97%, at least 98%, at least 99%, or 100% identity to the amino acid sequence of ANQVEQSPQSLII-LEGKNVTLQCQYTVSPFSNLRWYKQDT-GRGPVSLTILTFSENTKSNG RYTATLDADTKQSSLHI-TASQLSDSASYICVVNSAQGLYIPTFGRGTSLIVHP (SEQ ID NO:7). In some embodiments, a TCR or TCR fusion protein of the present disclosure comprises an alpha chain variable region that comprises the amino acid sequence of SEQ ID NO:7.

In some embodiments, a TCR or TCR fusion protein of the present disclosure comprises a beta chain variable region that comprises an amino acid sequence having at least 90%, at least 91%, at least 92%, at least 93%, at least 94%, at least 95%, at least 96%, at least 97%, at least 98%, at least 99%, or 100% identity to the amino acid sequence of DVKVTQSSRYLVKRTGEKVFLECVQDLD-HENMFWYRQDPGLGLRLIYFSRFATGKEKG DIP-EGYSVSREKKERFSLILESASTQQTSMYL-CASSSDQNSGDPYEQYFGPGTRLTVT (SEQ ID NO:13). In some embodiments, a TCR or TCR fusion protein of the present disclosure comprises a beta chain variable region that comprises the amino acid sequence of SEQ ID NO:13. In some embodiments, a TCR or TCR fusion protein of the present disclosure comprises an alpha chain variable region that comprises the amino acid sequence of SEQ ID NO:7 and a beta chain variable region that comprises the amino acid sequence of SEQ ID NO:13.

In some embodiments, a TCR or TCR fusion protein of the present disclosure comprises a TCR alpha chain comprising an alpha chain variable region of the present disclosure and an alpha chain constant region. In some embodiments, a TCR or TCR fusion protein of the present disclosure comprises an alpha chain constant region that comprises an amino acid sequence having at least 90%, at least 91%, at least 92%, at least 93%, at least 94%, at least 95%, at least 96%, at least 97%, at least 98%, at least 99%, or 100% identity to the amino acid sequence of YIQKPD-PAVYQLRD-SKSSDKSVCLFTDFDSQTQVSQSKDSDVYITDKCVL DMRSMDFKS NSAVAWSQKSDFACANAFQNSIIPEDT (SEQ ID NO:9). In some embodiments, a TCR or TCR fusion protein of the present disclosure comprises an alpha chain constant region that comprises the amino acid sequence of SEQ ID NO:9.

In some embodiments, a TCR or TCR fusion protein of the present disclosure comprises a TCR beta chain comprising a beta chain variable region of the present disclosure and a beta chain constant region. In some embodiments, a TCR or TCR fusion protein of the present disclosure comprises a beta chain constant region that comprises an amino acid sequence having at least 90%, at least 91%, at least 92%, at least 93%, at least 94%, at least 95%, at least 96%, at least 97%, at least 98%, at least 99%, or 100% identity to the amino acid sequence of EDLKNVFPPEVAVFEPSE-AEISHTQKATLVCLATGFYPDHVELSWWVNGKEV-HSGVCT DPQPLKEQPALQDSRY-ALSSRLRVSATFWQDPRNHFRCQVQFYGLSENDEWT QDRAKP VTQIVSAEAWGRAD (SEQ ID NO:14). In some embodiments, a TCR or TCR fusion protein of the present disclosure comprises a beta chain constant region that comprises the amino acid sequence of SEQ ID NO:14. In some embodiments, a TCR or TCR fusion protein of the present disclosure comprises an alpha chain constant region that comprises the amino acid sequence of SEQ ID NO:9 and a beta chain constant region that comprises the amino acid sequence of SEQ ID NO:14.

In some embodiments, a TCR or TCR fusion protein of the present disclosure comprises an alpha chain comprising an alpha chain variable region that comprises the amino acid sequence of SEQ ID NO:7 and an alpha chain constant region that comprises the amino acid sequence of SEQ ID NO:9; and a beta chain comprising a beta chain variable region that comprises the amino acid sequence of SEQ ID NO:13 and a beta chain constant region that comprises the amino acid sequence of SEQ ID NO:14.

In some embodiments, a TCR or TCR fusion protein of the present disclosure comprises an alpha chain that comprises an amino acid sequence having at least 90%, at least 91%, at least 92%, at least 93%, at least 94%, at least 95%, at least 96%, at least 97%, at least 98%, at least 99%, or 100% identity to the amino acid sequence of ANQVEQSPQSLII-LEGKNVTLQCQYTVSPFSNLRWYKQDT-GRGPVSLTILTFSENTKSNG RYTATLDADTKQSSLHI-TASQLSDSASYICVVNSAQGLYIPTFGRGTSLIVHPYI QKPDPA VYQLRD-SKSSDKSVCLFTDFDSQTQVSQSKDSDVYITDKCVL DMRSMDFKSNSAVAWS QKSDFACANAFQNSIIPEDT (SEQ ID NO:11). In some embodiments, a TCR or TCR fusion protein of the present disclosure comprises an alpha chain that comprises the amino acid sequence of SEQ ID NO:11.

In some embodiments, a TCR or TCR fusion protein of the present disclosure comprises a beta chain that comprises an amino acid sequence having at least 90%, at least 91%, at least 92%, at least 93%, at least 94%, at least 95%, at least 96%, at least 97%, at least 98%, at least 99%, or 100% identity to the amino acid sequence of DVKVTQSSRYL-VKRTGEKVFLECVQDLD-HENMFWYRQDPGLGLRLIYFSRFATGKEKG DIP-EGYSVSREKKERFSLILESASTQQTSMYLCASSSDQN SGDPYEQYFGPGTRLTVTEDL KNVFPPEVAVFEPSE-AEISHTQKATLVCLATGFYPDHVELSWWVNGKEV-HSGVCTDPQP LKEQPALQDSRY-ALSSRLRVSATFWQDPRNHFRCQVQFYGLSENDEWT QDRAKPVTQI VSAEAWGRAD (SEQ ID NO:16). In some embodiments, a TCR or TCR fusion protein of the present disclosure comprises a beta chain that comprises the amino acid sequence of SEQ ID NO:16. In some embodiments, a TCR or TCR fusion protein of the present disclosure comprises an alpha chain that comprises the amino acid sequence of SEQ ID NO:11 and a beta chain that comprises the amino acid sequence of SEQ ID NO:16.

In some embodiments, a TCR fusion protein of the present disclosure comprises a T cell engaging domain that binds a protein expressed on a cell surface of a T cell. In some embodiments, the T cell engaging domain binds a protein expressed on a cell surface of a T cell and recruits the T cell to a cell expressing a GVYDGREHTV (SEQ ID NO:34) HLA-A*02 complex. In some embodiments, the T cell engaging domain binds a protein expressed on a cell surface of a T cell and activates the T cell, e.g., via binding to the protein expressed on the cell surface. In some embodiments, the protein expressed on the cell surface of the T cell is a cell surface receptor. In some embodiments, the protein expressed on the cell surface of the T cell is a human CD3 polypeptide.

In some embodiments, the T cell engaging domain comprises an antibody antigen binding domain. In some embodiments, the antibody antigen binding domain binds to a cell surface receptor expressed by a T cell. In some embodiments, the antibody antigen binding domain binds to a cell surface receptor expressed by a T cell and causes activation of the T cell. In some embodiments, the T cell engaging domain is part of, or comprises, a single chain variable fragment (scFv). In some embodiments, the scFv is an anti-CD3 scFv. Other single chain antibody fragment formats are known in the art.

In some embodiments, the scFv is a U28 variant anti-CD3 scFv. In some embodiments, the scFv comprises the amino acid sequence of AIQMTQSPSSLSASVGDRVTIT-CRASQDIRNYLNWYQQKPGKAPKLLIYYTSR-LESGVPS RFSGSGSGTDYTLTISSLQPEDFA-TYYCQQGNTLPWTFGQGTKVEIKGGGGSGGGGSGG GGSGGGGSGGGSEVQLVESGGGLVQPGGSLRLS-CAASGYSFTGYAMNWVRQAPGKGL EWVAL-INPYKGVSTYNQKFKDRFTFSVDKSKNTAYLQMNSL-RAEDTAVYYCARSGYY GDSDWYFDVWGQGTLVTVSS (SEQ ID NO:17). In some embodiments, the scFv comprises the amino acid sequence of AIQMTQSPSSLSASVGDRVTITCRASQDIR-NYLNWYQQKPGKAPKLLIYYTSRLESGVPS RFSGSGSGTDYTLTISSLQPEDFA-TYYCQQGNTLPWTFGQGTKVEIKGGGGSGGGGSGG GGSGGGGSGGGSEVQLVESGGGLVQPGGSLRLS-CAASGYSFTGYTMNWVRQAPGKGL EWVAL-INPYKGVSTYNQKFKDRFTISVDKSKNTAYLQMNSL-RAEDTAVYYCARSGYYG DSDWYFDVWGQGTLVTVSS (SEQ ID NO:35).

In some embodiments, the T cell engaging domain that binds a protein expressed on a cell surface of a T cell (e.g., the scFv) is covalently linked to the TCR via linker. In some embodiments, the linker is a Gly-Ser linker. In some embodiments, the linker comprises an amino acid sequence selected from the group consisting of SEQ ID Nos:18-25.

In some embodiments, the C-terminus of the T cell engaging domain that binds a protein expressed on a cell surface of a T cell (e.g., the scFv) is covalently linked to the N-terminus of the TCR beta chain variable domain via a linker of the present disclosure.

In some embodiments, the N-terminus of the antibody Fc domain is covalently linked to the C-terminus of the TCR alpha chain constant domain via a hinge sequence. In some embodiments, the hinge sequence comprises the amino acid sequence of DKTHTCPP (SEQ ID NO:31) or DKTH-TCPPC (SEQ ID NO:36).

In some embodiments, a TCR fusion protein of the present disclosure comprises an antibody Fc domain, e.g., a human antibody Fc domain. In some embodiments, a TCR fusion protein of the present disclosure comprises a human IgG1, human IgG2, or human IgG4 Fc domain. Advantageously, the present disclosure demonstrates that TCR fusion proteins with the Fc domain fused to the alpha or beta chain were found to have substantially improved pharmacokinetics, as compared to similar molecules without an Fc expressed from E. coli or CHO cells.

In some embodiments, the antibody Fc domain comprises one or more mutations that attenuate an effector function of the Fc domain. Exemplary effector functions include, without limitation, complement-dependent cytotoxicity (CDC) and/or antibody-dependent cellular cytotoxicity (ADCC). In exemplary embodiments, the modification to attenuate effector function is a modification that alters the glycosylation pattern of the Fc domain, e.g., a modification that results in an aglycosylated Fc domain. In exemplary embodiments, the modification to attenuate effector function is a modification that does not alter the glycosylation pattern of the Fc domain. In certain embodiments, the modification to attenuate effector function reduces or eliminates binding to human effector cells, binding to one or more Fc receptors, and/or binding to cells expressing an Fc receptor. In an exemplary embodiment, the Fc variants described herein comprise an N297G or N297A modification in the Fc domain of human IgG1. In an exemplary embodiment, the Fc variants described herein comprise the following modifications: L234A, L235A and P329G in the Fc domain of human IgG1, that result in attenuated effector function. In some embodiments, the antibody Fc domain is a human IgG1 Fc domain comprising a mutation at residue N297, numbering according to EU index. For example, in some embodiments, the mutation is an N297G substitution. Other suitable mutations (e.g., at residue N297) are known to those skilled in the art.

In various embodiments, Fc variants having reduced effector function refer to Fc variants that reduce effector function (e.g., CDC, ADCC, and/or binding to FcR, etc. activities) by at least 10%, 20%, 30%, 40%, 50%, 60%, 70%, 80%, 90%, 95%, 97%, 98%, 99% or more as compared to the effector function achieved by a wild-type Fc domain (e.g., an Fc domain not having a mutation to reduce effector function, although it may have other mutations). In certain embodiments, Fc variants having reduced effector function refer to Fc variants that eliminate all detectable effector function as compared to a wild-type Fc domain. Assays for measuring effector function are known in the art and described below.

In vitro and/or in vivo cytotoxicity assays can be conducted to confirm the reduction/depletion of CDC and/or ADCC activities. For example, Fc receptor (FcR) binding assays can be conducted to ensure that the Fc domain or fusion protein lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)). In certain embodiments, the Fc variants described herein comprise modifications to the Fc domain that reduce effector function as described in Strohl, Current Opinion in Biotechnology, 20; 685-691 (2009).

In some embodiments, the antibody Fc domain is a human IgG1 Fc domain comprising one or more mutation(s) at residue(s) E233, L234, L235, and/or G236, numbering according to EU index. For example, in some embodiments, the antibody Fc domain is a human IgG1 Fc domain comprising substitutions N297G, E233P, L234V, L235A, and a deletion at G236, numbering according to EU index.

In some embodiments, the antibody Fc domain is a human IgG1 Fc domain comprising one or more mutation(s) at residue(s) L234, L235, and P329, numbering according to EU index. For example, in some embodiments, the antibody Fc domain is a human IgG1 Fc domain comprising substitutions L234A, L235A, and P329G, numbering according to EU index.

In some embodiments, the antibody Fc domain is fused to a TCR of the present disclosure via a hinge sequence. In some embodiments, the hinge sequence comprises the amino acid sequence of DKTHTCPP (SEQ ID NO:31) or DKTHTCPPC (SEQ ID NO:36).

In some embodiments, a TCR fusion protein of the present disclosure comprises two antibody Fc domains. In some embodiments, one of the two antibody Fc domains is fused or linked (e.g., covalently linked) with a TCR of the present disclosure. FIG. 1B discloses a configuration in which one of the two antibody Fc domains is linked with a TCR alpha chain (e.g., via the alpha chain constant domain), in accordance with some embodiments. In some embodiments, the two antibody Fc domains are associated with each other, e.g., via one or more covalent linkages and/or one or more amino acid substitutions on one or both of the antibody Fc domains that promote heterodimerization.

In some embodiments, the first antibody Fc domain is fused to the TCR via a first hinge sequence, and a second hinge sequence is linked to the N-terminus of the second antibody Fc domain. In some embodiments, the first and second hinge sequences are linked via one or more interchain disulfide bonds between the first and second hinge sequences. In some embodiments, the first and second antibody Fc domains both further comprise a hinge sequence, and the first and second hinge sequences are linked via one or more interchain disulfide bonds between the first and second hinge sequences. In some embodiments, the first and second hinge sequences both comprise the amino acid sequence of DKTHTCPP (SEQ ID NO:31) or DKTHTCPPC (SEQ ID NO:36). In some embodiments, a hinge sequence of the present disclosure is an antibody hinge sequence, e.g., a sequence from an antibody hinge region.

In some embodiments, one of the first and second antibody Fc domains comprises one or more knob-forming mutations and the other of the first and second antibody Fc domains comprises one or more corresponding hole-forming mutations to promote heterodimerization of the antibody Fc domains.

In some embodiments, heterodimerization of two antibody Fc domains is promoted by "knob-in-hole" engineering. For example, two polypeptides comprising antibody Fc domains can be assembled into a TCR fusion protein in vitro, where a first antibody Fc domain comprises an amino acid modification in its CH3 domain that forms a protuberance, and the second antibody Fc domain comprises an amino acid modification in its CH3 domain that forms a cavity. The protuberance is positionable into the cavity, thereby forming the TCR fusion protein upon assembly.

In this approach, two polypeptides comprising an antibody Fc domain each comprise an interface. An interface of one polypeptide interacts with a corresponding interface on the other polypeptide, thereby allowing the two polypeptides to associate. These interfaces may be engineered such that a "knob" or "protuberance" (these terms may be used interchangeably herein) located in the interface of one polypeptide corresponds with a "hole" or "cavity" (these terms may be used interchangeably herein) located in the interface of the other polypeptide. In some embodiments, the hole is of identical or similar size to the knob and suitably positioned such that when the two interfaces interact, the knob of one interface is positionable in the corresponding hole of the other interface. Without wishing to be bound to theory, this is thought to stabilize the heteromultimer and favor formation of the heteromultimer over other species, for example homomultimers. In some embodiments, this approach may be used to promote the heteromultimerization of two different polypeptides, promoting association of the two antibody Fc domains.

In some embodiments, a knob may be constructed by replacing a small amino acid side chain with a larger side chain. In some embodiments, a hole may be constructed by replacing a large amino acid side chain with a smaller side chain. Knobs or holes may exist in the original interface, or they may be introduced synthetically. For example, knobs or holes may be introduced synthetically by altering the nucleic acid sequence encoding the interface to replace at least one "original" amino acid residue with at least one "import" amino acid residue. Methods for altering nucleic acid sequences may include standard molecular biology techniques well known in the art. The side chain volumes of various amino acid residues are shown in the following table. In some embodiments, original residues have a small side chain volume (e.g., alanine, asparagne, aspartic acid, glycine, seine, threonine, or valine), and import residues for forming a knob are naturally occurring amino acids and may include arginine, phenylalanine, tyrosine, and tryptophan. In some embodiments, original residues have a large side chain volume (e.g., arginine, phenylalanine, tyrosine, and tryptophan), and import residues for forming a hole are naturally occurring amino acids and may include alanine, serine, threonine, and valine.

TABLE B

Properties of amino acid residues

| Amino acid | One-letter abbreviation | Mass[a] (daltons) | Volume[b] (Å$^3$) | Accessible surface area[c] (Å$^2$) |
|---|---|---|---|---|
| Alanine (Ala) | A | 71.08 | 88.6 | 115 |
| Arginine (Arg) | R | 156.20 | 173.4 | 225 |
| Asparagine (Asn) | N | 114.11 | 117.7 | 160 |
| Aspartic Acid (Asp) | D | 115.09 | 111.1 | 150 |
| Cysteine (Cys) | C | 103.14 | 108.5 | 135 |
| Glutamine (Gln) | Q | 128.14 | 143.9 | 180 |
| Glutamic Acid (Glu) | E | 129.12 | 138.4 | 190 |
| Glycine (Gly) | G | 57.06 | 60.1 | 75 |
| Histidine (His) | H | 137.15 | 153.2 | 195 |
| Isoleucine (Ile) | I | 113.17 | 166.7 | 175 |
| Leucine (Leu) | L | 113.17 | 166.7 | 170 |
| Lysine (Lys) | K | 128.18 | 168.6 | 200 |
| Methionine (Met) | M | 131.21 | 162.9 | 185 |
| Phenylalanine (Phe) | F | 147.18 | 189.9 | 210 |
| Proline (Pro) | P | 97.12 | 122.7 | 145 |

TABLE B-continued

Properties of amino acid residues

| Amino acid | One-letter abbreviation | Mass[a] (daltons) | Volume[b] (Å$^3$) | Accessible surface area[c] (Å$^2$) |
|---|---|---|---|---|
| Serine (Ser) | S | 87.08 | 89.0 | 115 |
| Threonine (Thr) | T | 101.11 | 116.1 | 140 |
| Tryptophan (Trp) | W | 186.21 | 227.8 | 255 |
| Tyrosine (Tyr) | Y | 163.18 | 193.6 | 230 |
| Valine (Val) | V | 99.14 | 140.0 | 155 |

[a]Molecular weight of amino acid minus that of water. Values from Handbook of Chemistry and Physics, 43$^{rd}$ ed. Cleveland, Chemical Rubber Publishing Co., 1961.
[b]Values from A.A. Zamyatnin, Prog. Biophys. Mol. Biol. 24:107-123, 1972.
[c]Values from C. Chothia, J. Mol. Biol. 105:1-14, 1975. The accessible surface area is defined in FIGS. 6-20 of this reference.

In some embodiments, original residues for forming a knob or hole are identified based on the three-dimensional structure of the heteromultimer. Techniques known in the art for obtaining a three-dimensional structure may include X-ray crystallography and NMR. In some embodiments, the interface is the CH3 domain of an immunoglobulin constant domain. In these embodiments, the CH3/CH3 interface of human IgG$_1$ involves sixteen residues on each domain located on four anti-parallel β-strands. Without wishing to be bound to theory, mutated residues are preferably located on the two central anti-parallel β-strands to minimize the risk that knobs can be accommodated by the surrounding solvent, rather than the compensatory holes in the partner CH3 domain. In some embodiments, the mutations forming corresponding knobs and holes in two immunoglobulin polypeptides correspond to one or more pairs provided in the following table.

TABLE C

Exemplary sets of corresponding knob-and hole-forming mutations

| CH3 of first Fc | CH3 of second Fc |
|---|---|
| T366Y | Y407T |
| T366W | Y407A |
| T366W | T366S:L368A:Y407V |
| F405A | T394W |
| Y407T | T366Y |
| T366Y:F405A | T394W:Y407T |
| T366W:F405W | T394S:Y407A |
| F405W:Y407A | T366W:T394S |
| F405W | T394S |

Mutations are denoted by the original residue, followed by the position using the Kabat numbering system, and then the import residue (all residues are given in single-letter amino acid code).
Multiple mutations are separated by a colon.

In some embodiments, an antibody Fc domain comprises a CH3 domain comprising one or more amino acid substitutions listed in Table C above. In some embodiments, a TCR fusion protein comprises a first antibody Fc domain comprising a CH3 domain comprising one or more amino acid substitutions listed in the left column of Table C, and a second antibody Fc domain comprising a CH3 domain comprising one or more corresponding amino acid substitutions listed in the right column of Table C.

For example, in some embodiments, one of the first and second antibody Fc domains comprises a T366W substitution, and the other of the first and second antibody Fc domains comprises T366S, L368A, Y407V substitutions, numbering according to EU index.

In some embodiments, one of the antibody Fc domains comprises the amino acid sequence of SEQ ID NO:27, and the other of the antibody Fc domains comprises the amino acid sequence of SEQ ID NO:26. In some embodiments, the first antibody Fc domain is covalently linked to the TCR and comprises the amino acid sequence of SEQ ID NO:27, and the second antibody Fc domain comprises the amino acid sequence of SEQ ID NO:26.

Following mutation of the DNA as discussed above, polynucleotides encoding modified antibody Fc domains with one or more corresponding knob- or hole-forming mutations may be expressed and purified using standard recombinant techniques and cell systems known in the art. See, e.g., U.S. Pat. Nos. 5,731,168; 5,807,706; 5,821,333; 7,642,228; 7,695,936; 8,216,805; U.S. Pub. No. 2013/0089553; and Spiess et al., Nature Biotechnology 31: 753-758, 2013. Corresponding knob- and hole-bearing antibody Fc domain containing-polypeptides may be expressed in host cells in co-culture and purified together as a heteromultimer, or they may be expressed in single cultures, separately purified, and assembled in vitro. Standard techniques known in the art that allow for measuring the abundance of homo-multimeric vs. hetero-multimeric species may include size exclusion chromatography. In some embodiments, each modified polypeptide is expressed separately using standard recombinant techniques, and they may be assembled together in vitro. Assembly may be achieved, for example, by purifying each modified polypeptide, mixing and incubating them together in equal mass, reducing disulfides (e.g., by treating with dithiothreitol), concentrating, and reoxidizing the polypeptides. Formed TCR fusion proteins may be purified using standard techniques including cation-exchange chromatography and measured using standard techniques including size exclusion chromatography. For a more detailed description of these methods, see Speiss et al., Nat Biotechnol 31:753-8, 2013. In some embodiments, polypeptides comprising modified antibody Fc domains may be expressed separately in CHO cells and assembled in vitro using the methods described above.

In some embodiments, a TCR fusion protein of the present disclosure comprises: a first polypeptide comprising, from N-terminus to C-terminus: the TCR alpha chain variable region, an alpha chain constant region, a first hinge sequence, and a first antibody Fc domain; a second polypeptide comprising, from N-terminus to C-terminus: a single chain variable fragment (scFv) that binds human CD3 expressed on the cell surface of a T cell, a linker, the beta chain variable region, and a beta chain constant region; and a third polypeptide comprising, from N-terminus to C-terminus: a second hinge sequence and a second antibody Fc domain. Advantageously, the present disclosure demonstrates that this TCR fusion protein format (see, e.g., FIG. 1B) had the most favorable pharmacokinetic properties and highest activity (i.e., potency and selectivity) of the formats tested.

In some embodiments, the first and second polypeptides are linked via one or more disulfide bonds between the alpha and beta chain constant regions, e.g., as described herein.

In some embodiments, the first and third polypeptides are linked via one or more interchain disulfide bonds between the first and second hinge sequences and/or one or more corresponding knob-forming and hole-forming mutations on the antibody Fc domains.

In some embodiments, a TCR fusion protein of the present disclosure comprises a first polypeptide comprising the amino acid sequence of SEQ ID NO:29, a second polypeptide comprising the amino acid sequence of SEQ ID NO:30, and a third polypeptide comprising the amino acid sequence of SEQ ID NO:28.

Further provided herein are polynucleotides encoding any of the TCRs and TCR fusion proteins disclosed herein. For example, in some embodiments, the present disclosure provides a kit of polynucleotides comprising one, two, or three polynucleotides encoding one, two, or three polypeptides of the present disclosure. In some embodiments, the present disclosure provides a kit of polynucleotides comprising a first polynucleotide encoding a first polypeptide comprising the amino acid sequence of SEQ ID NO:29, a second polynucleotide encoding a second polypeptide comprising the amino acid sequence of SEQ ID NO:30, and a third polynucleotide encoding a third polypeptide comprising the amino acid sequence of SEQ ID NO:28.

Further provided herein are vectors (e.g., expression vectors) comprising any of the polynucleotides of the present disclosure. In some embodiments, a vector of the present disclosure comprises polynucleotides encoding one, two, or three (e.g., all) polypeptides of a TCR fusion protein of the present disclosure. For example, in some embodiments, a vector comprises a first polynucleotide encoding a first polypeptide comprising the amino acid sequence of SEQ ID NO:29, a second polynucleotide encoding a second polypeptide comprising the amino acid sequence of SEQ ID NO:30, and a third polynucleotide encoding a third polypeptide comprising the amino acid sequence of SEQ ID NO:28. In some embodiments, a vector encodes a first polypeptide comprising the amino acid sequence of SEQ ID NO:29, a second polypeptide comprising the amino acid sequence of SEQ ID NO:30, and a third polypeptide comprising the amino acid sequence of SEQ ID NO:28. Further provided herein is a kit of vectors (e.g., expression vectors) comprising a first vector comprising a first polynucleotide encoding a first polypeptide comprising the amino acid sequence of SEQ ID NO:29, a second vector comprising a second polynucleotide encoding a second polypeptide comprising the amino acid sequence of SEQ ID NO:30, and a third vector comprising a third polynucleotide encoding a third polypeptide comprising the amino acid sequence of SEQ ID NO:28.

For recombinant production of a TCR fusion protein, nucleic acids encoding the TCR fusion protein, e.g., as described above, are isolated and inserted into one or more vectors for further cloning and/or expression in a host cell. Such nucleic acids may be readily isolated and sequenced using conventional procedures (e.g., by using oligonucleotide probes that are capable of binding specifically to genes encoding the polypeptide chains of the TCR fusion protein) or produced by recombinant methods or obtained by chemical synthesis.

Further provided herein are host cells comprising any of the polynucleotides and/or vectors of the present disclosure. Suitable host cells for cloning or expression of polynucleotides and/or vectors of the present disclosure are known in the art. Suitable host cells for the expression of (glycosylated) proteins are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells (as described, e.g., in Mather, J. P. et al., Annals N.Y. Acad. Sci. 383 (1982) 44-68); MRC 5 cells; and FS4 cells. Other useful mammalian host cell lines include Chinese hamster ovary (CHO) cells, including DHFR− CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, NJ (2004), pp. 255-268. In one aspect, the host cell is eukaryotic, e.g., a Chinese Hamster Ovary (CHO) cell or lymphoid cell (e.g., Y0, NS0, Sp20 cell).

Further provided herein are methods for producing any of the TCR fusion proteins disclosed herein. In some embodiments, the methods comprise culturing a host cell of the present disclosure under conditions suitable for production of a TCR fusion protein. In some embodiments, the methods further comprise recovering the TCR fusion protein from the host cell.

IV. METHODS AND USES

Certain aspects of the present disclosure relate to methods of treating cancer. In some embodiments, the methods comprise administering an effective amount of a TCR fusion protein or pharmaceutical composition of the present disclosure to an individual. In some embodiments, the individual is a human.

In some embodiments, the individual has a cancer that expresses MAGE-A4.

For example, the cancer or tumor may be of the breast, esophagus, stomach (e.g. gastric cancer), head & neck, lung, ovary, or bladder. The cancer or tumor may express MAGE A4, and/or may be a solid tumor. In some embodiments, the cancer or tumor is synovial sarcoma. In some embodiments, the cancer or tumor has squamous cell histology, i.e., is a squamous cell cancer or tumor.

In some embodiments, the individual is of HLA-A*02 subtype.

The present disclosure further comprises pharmaceutical compositions comprising TCRs or TCR fusion proteins of the present disclosure and a pharmaceutically acceptable carrier. For administration to patients, the TCRs and TCR-anti CD3 fusion molecules of the disclosure may be provided in a pharmaceutical composition together with one or more pharmaceutically acceptable carriers or excipients. Therapeutic or imaging TCRs, or cells, in accordance with the present disclosure will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

In some embodiments, the TCR fusion protein or pharmaceutical composition is administered intravenously or by intratumoral injection. The TCR fusion protein or pharmaceutical composition may be adapted for administration by any appropriate route, such as parenteral (including subcutaneous, intramuscular, or intravenous), enteral (including oral or rectal), inhalation or intranasal routes. Such compositions may be prepared by any method known in the art of pharmacy, for example by mixing the active ingredient with the carriers) or excipient(s) under sterile conditions.

Dosages of the substances of the present disclosure can vary between wide limits, depending upon the disease or disorder to be treated, the age and condition of the individual to be treated, etc. a suitable dose range for a soluble TCR of the present disclosure associated with an anti-CD3 antibody may be between 25 ng/kg and 50 µg/kg. A physician will ultimately determine appropriate dosages to be used.

TCRs, pharmaceutical compositions, vectors, nucleic acids and cells of the present disclosure may be provided in substantially pure form, for example at least 80%, at least 85%, at least 90%, at least 91%, at least 92%, at least 93%, at least 94%, at least 95%, at least 96%, at least 97%, at least 98%, at least 99% or 100% pure.

In some embodiments, the methods of the present disclosure further comprise administering to the individual a second anti-cancer agent.

V. KITS OR ARTICLES OF MANUFACTURE

In another aspect, an article of manufacture containing materials useful for the treatment and/or prevention of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises a TCR fusion protein of the present disclosure; and (b) a second container with a composition contained therein, wherein the composition comprises a further cytotoxic or otherwise therapeutic agent. The article of manufacture in this aspect of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Engineering Glycosylation on TCR:Anti-CD3 Fusion Molecules

Fusion proteins comprising a soluble TCR with specific, high-affinity binding to the germline cancer antigen MAGE-A4 and an antibody fragment (e.g., an anti-CD3 scFv) that binds to T cells have been described as a potential immunotherapeutic. See, e.g., WO2017175006. Further engineering was undertaken in order to provide TCR:anti-CD3 fusion molecules with favorable properties, e.g., potency and in vivo pharmacokinetics.

Materials and Methods

TCR:Anti-CD3 Fusion Molecules

Monoglycosylated TCR:anti-CD3 fusion molecule comprised three polypeptide chains, corresponding to SEQ ID Nos:28-30, expressed in CHO cells. Three polypeptide chains comprised: (1) a free Fc domain with knob mutation (SEQ ID NO:26) and hinge sequence (SEQ ID NO:31); (2) soluble, monoclonal, high affinity anti-MAGE-A4 TCR alpha chain comprising an alpha chain variable region comprising the amino acid sequence of SEQ ID NO:7 and an alpha chain constant region comprising the amino acid sequence of SEQ ID NO:9 with an Fc domain with hole mutations (SEQ ID NO:27) linked to the C-terminus of the TCR alpha chain via hinge sequence (SEQ ID NO:31); and (3) an anti-CD3 scFv variant comprising the amino acid sequence of SEQ ID NO:17 linked to the N-terminus of the TCR beta chain via linker (SEQ ID NO:18), wherein the beta chain comprised a beta chain variable region comprising the amino acid sequence of SEQ ID NO:13 and a beta chain constant region comprising the amino acid sequence of SEQ ID NO:14. Compared to parental anti-CD3 scFv, the variant comprised a T164A mutation in CDR1 and an I201F mutation in FR3 (numbering according to SEQ ID NO:17).

The aglycosylated TCR:anti-CD3 fusion molecule comprised the same sub-components as the monoglycosylated form, except that the alpha chain variable region comprised the amino acid sequence of SEQ ID NO:8 (hence the full length alpha chain comprised the amino acid sequence of SEQ ID NO:12). Both aglycosylated and monoglycosylated forms had N→Q substitutions at the 3 N-glycosylation sites of the parental alpha chain constant region (SEQ ID NO:10). Both aglycosylated and monoglycosylated forms had an N→Q substitution at the N-glycosylation site of the parental beta chain constant region (SEQ ID NO:15).

Pharmacokinetics

Male SCID mice were used (N=4). Aglycosylated or monoglycosylated TCR:anti-CD3 fusion molecules were injected via single IV bolus injection at 0.665 mg/kg, 0.0665 mg/kg, or 0.00665 mg/kg. Control N297G TCR:anti-CD3 fusion molecule was injected at 0.665 mg/kg as a control. All TCR:anti-CD3 fusion molecules were provided at 0.133 mg/mL. Serial samples (25 μL blood→10 μL serum) were collected at 5 minutes, 1 hour, 24 hours, 7 days, 10 days, 14 days, and 21 days after injection. Sample was detected in serum by electrochemilluminescent immunoassay, with capture on biotinylated MAGEA4 peptide-HLA, and detection with sulfo-tagged anti-scFv antibody.

Analysis of Global N-Linked Glycan Composition

10 μg of protein were denatured with 8 M guanidine HCl at 1:1 volume ratio and reduced with 100 mM dithiothreitol for 10 min at 95° C. Samples were diluted with 100 mM Tris HCl, pH 7.5, to a final concentration of 2 M guanidine HCl, followed by overnight N-linked deglycosylation at 37° C. with 2 μl of PNGase F (P0705S, New England BioLabs). After deglycosylation, 150 ng of each sample were injected onto a HPLC system (Agilent 1260) via an autosampler. Glycans were enriched and separated on a PGC-Chip (G4240-64010, Agilent) containing porous graphitized carbon columns. A binary pump was used to deliver solvent A (99.88% water, 0.1% formic acid and 0.02% trifluoroacetic acid) and solvent B (90% acetonitrile, 9.88% water, 0.1% formic acid and 0.02% trifluoroacetic acid) as a gradient of 2% to 32% solvent B over 6 min at 0.5 μl/min and held for 1.5 min. Solvent B was then step-changed to 85% over 0.5 min and held for 1 min to clean the columns. Finally, solvent B was step-changed to 2% and held for 3 min for re-equilibration.

Separated glycans were analyzed on-line via nanospray ionization into a Q-TOF mass spectrometer (Agilent 6520) using the following parameters for data acquisition: 1.9 kV spray voltage; 325° C. gas temperature; 5 l/min drying gas flow; 160 V fragmentor voltage; 65 V skimmer voltage; 750 V oct 1 RF Vpp voltage; 400 to 3,000 m/z scan range; positive polarity; MS1 centroid data acquisition using extended dynamic range (2 GHz) instrument mode; 3 spectra/s; 333.3 ms/spectrum; 3243 transients/spectrum; and a CE setting of 0. Acquired mass spectral data were searched against a glycan library in the Agilent MassHunter Qualitative Analysis software. The software algorithm utilized a combination of accurate mass with a mass tolerance of 10 ppm and expected retention time for glycan identification. Each N-linked glycan was label-free quantified relative to the sum of all identified N-linked glycans within each sample by integrating the AUC of each extracted glycan chromatogram.

N-Linked Glycosylation Site Mapping

20 μg of protein were denatured with 8 M guanidine HCl at 1:1 volume ratio and reduced with 100 mM dithiothreitol for 10 min at 95° C. Samples were diluted with 100 mM Tris HCl, pH 7.5, to a final concentration of 2 M guanidine HCl, followed by overnight N-linked deglycosylation at 37° C. with 4 μl of PNGase F (P0705S, New England BioLabs). After deglycosylation, samples were alkylated with 40 mM iodoacetamide at room temperature for 30 min. Samples were split in half for separate enzymatic digestion with 0.1 μg trypsin (Promega) and 0.1 μg chymotrypsin (Thermo Fisher Scientific) at 37° C. overnight. Digests were quenched with 0.1% TFA and subjected to C18 stage-tip clean up with a 40% acetonitrile containing 59.9% water plus 0.1% TFA elution step. After clean up, peptides were dried down and reconstituted in 50 μl 10.1% TFA, where 1 μl was injected onto a UPLC system (Waters NanoAcquity) via an autosampler and separated on a 45° C. heated Acquity M-Class BEH C18 column (0.1 mm×100 mm, 1.7 m resin, Waters). A binary gradient pump was used to deliver solvent A (97.9% water, 2% acetonitrile and 0.1% formic acid) and solvent B (97.9% acetonitrile, 2% water and 0.1% formic acid) as a gradient of 2% to 25% solvent B over 35 min at 1 μl/min. The solvent was step-changed to 50% solvent B over 2 min and then held at 90% for 6 min to clean the column. Finally, the solvent was step-changed to 2% solvent B and held for 7 min for re-equilibration. Separated peptides were analyzed on-line via nanospray ionization into an Orbitrap Elite Hybrid Ion Trap-Orbitrap mass spectrometer (Thermo Fisher Scientific) using the following parameters for data acquisition: 60,000 resolution; 375-1,600 m/z scan range; positive polarity; centroid mode; 1 m/z isolation width with 0.25 activation Q and 10 ms activation time; CID activation; and a CE setting of 35. Data was collected in data dependent mode with the precursor ions being analyzed in the FTMS and the top 15 most abundant ions being selected for fragmentation and analysis in the ITMS.

Acquired mass spectral data was searched against the protein sequence using Byonic software (Protein Metrics Inc.) with the following parameters: 20 ppm precursor mass tolerance with 0.5 Da fragment mass tolerance; strict specificity on arginine and lysine with up to 1 missed cleavage for trypsin; strict specificity on leucine, phenylalanine, tryptophan, and tyrosine with up to 2 missed cleavages for chymotrypsin; fixed carbamidomethylation on cysteine; variable oxidation on methionine; and variable deamidation on asparagine. Byonic search results were analyzed in Byologic software (Protein Metrics Inc.) and filtered with a minimum MS2 score cut-off of 200. Peptide identification was confirmed by MS2 peptide fragmentation. Deamidated peptides containing N-linked sites were label-free quantified relative to its unmodified form by AUC integration of their extracted ion chromatograms in Thermo Xcalibur Qual Browser software (Thermo Fisher Scientific). Changes in deamidation were used to quantify glycosylation.

Binding Affinity

Anti-hIgG1 antibodies were immobilized onto a Biacore CM5 capture chip using standard EDC/NHS immobilization protocol. ImmTAC molecules were prepared in HBS-EP buffer at 1 ug/ml and captured on the anti-hIgG1 immobilized CM5 chip. Subsequently, the antigen (CD3 epsilon delta hetero dimeric Fc fusion) flew over the ImmTAC captured flow cells with 210 seconds of contact time and 300 seconds of dissociation time at a flow rate of 100 ul/min. Biacore was performed at 37° C. and the analyte (human CD3 epsilon delta hetero dimeric Fc fusion) concentration series were 0, 0.5, 2.5, 12.5, 50, 150 nM.

Results

Figure 1B:
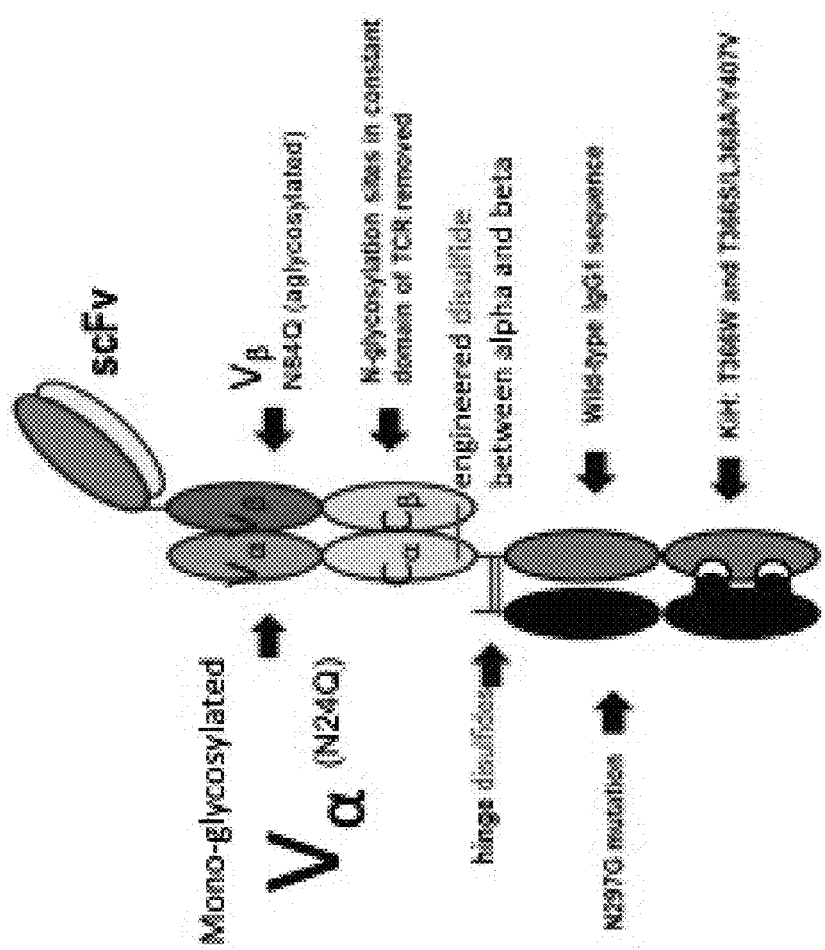
Figure 2A:
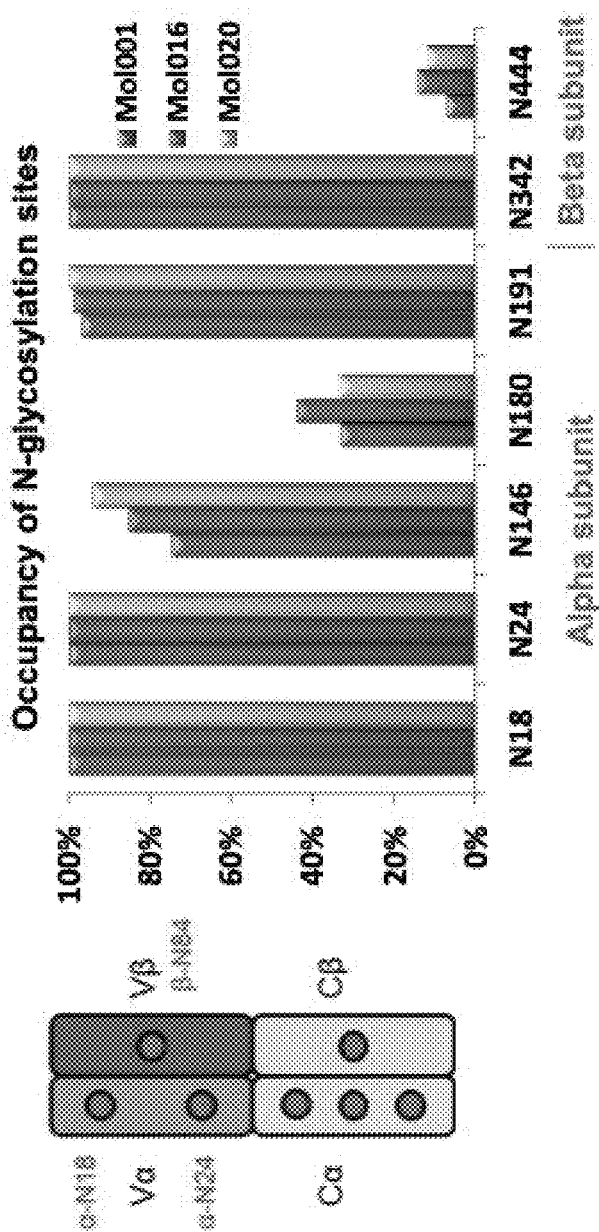
FIGS. 2A & 2B illustrate N-glycosylation of the TCR chains.
Figure 2B:
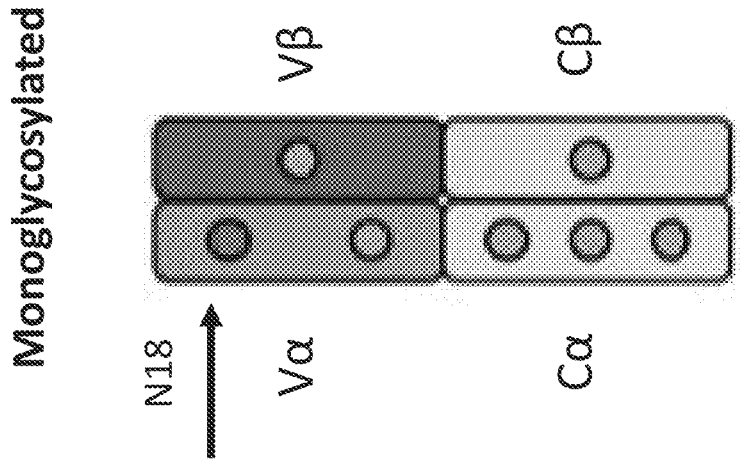
Figure 2B:
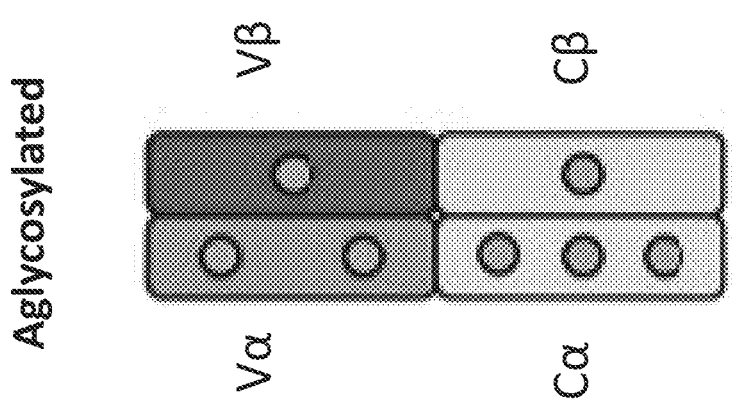

FIGS. 1A & 1B show TCR:anti-CD3 fusion molecules comprising an anti-CD3 scFv, soluble monoclonal high affinity TCR, and antibody Fc domain to extend in vivo half-life. As shown in FIG. 2A, the soluble monoclonal TCRs have 7 sites that are N-glycosylated when produced in CHO cells. All glycosylation sites were found to be removable without affecting activity or selectivity. Aglycosylated and monoglycosylated variants were selected for further study (FIG. 2B). In the monoglycosylated variant, all N-glycosylation sites were removed from the TCR constant regions using N→Q substitutions, and two of the three N-glycosylation sites from the variable regions were mutated (N24Q substitution on the alpha chain variable region, and N84Q substitution on the beta chain variable region). The aglycosylated variant comprised a further N18Q substitution on the alpha chain variable region to remove the final N-glycosylation site.

Figure 2C:
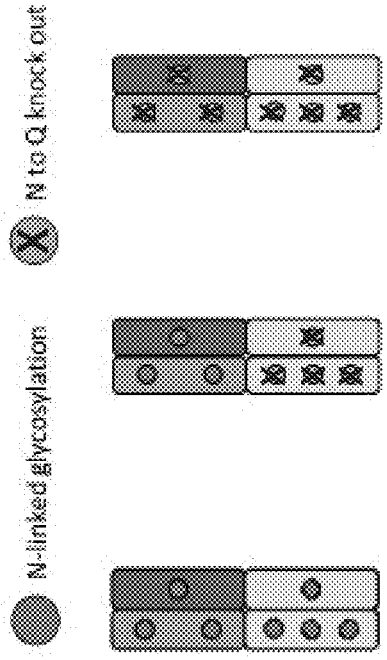
FIGS. 2C & 2D illustrate the effect of deglycosylation on TCR:anti-CD3 fusion molecule yield.
Figure 2D:
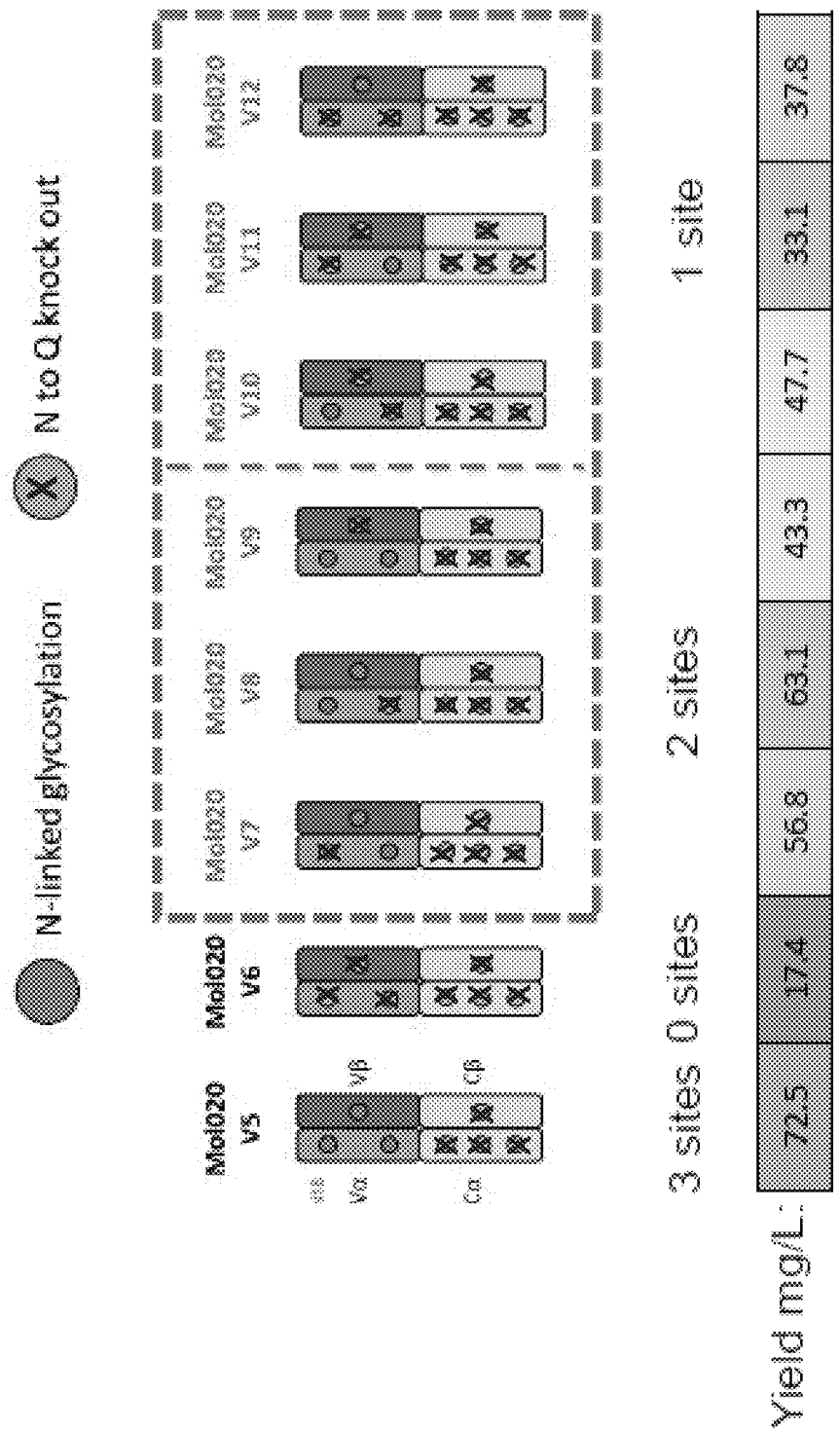

The effect of removing N-glycosylation sites from the variable and constant regions on protein yield was also examined. Removal of N-glycosylation sites from the TCR variable regions had a significant negative impact on yield, whereas removal of N-glycosylation sites from the TCR constant regions did not affect yield (FIG. 2C). A series of double and single N-glycosylation site variants was constructed to examine the effects of removing individual N-glycosylation sites from the TCR variable region (FIG. 2D). The results demonstrated a graduated loss in yield with reduced glycosylation, with the fully aglycosylated molecule showing a significant reduction in yield. However, preserving N-glycosylation at the N18 residue was found to provide the largest boost to yield of any single site.

Figure 3A:
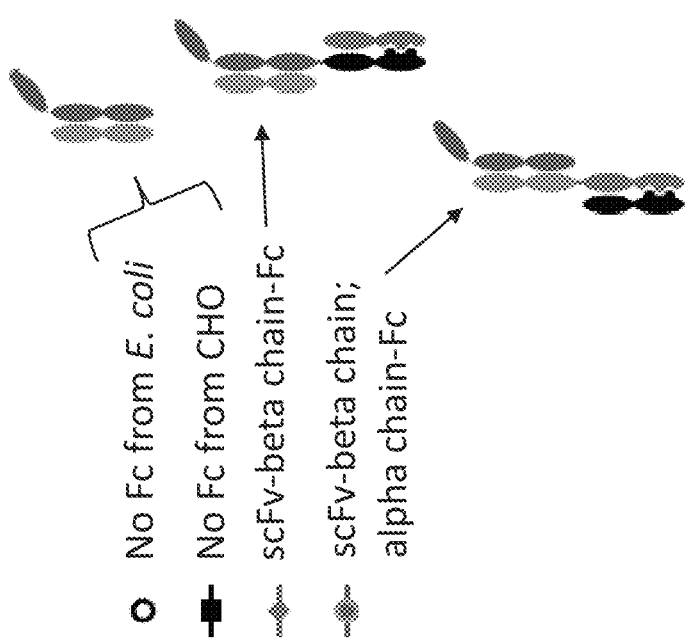
Figure 3A:
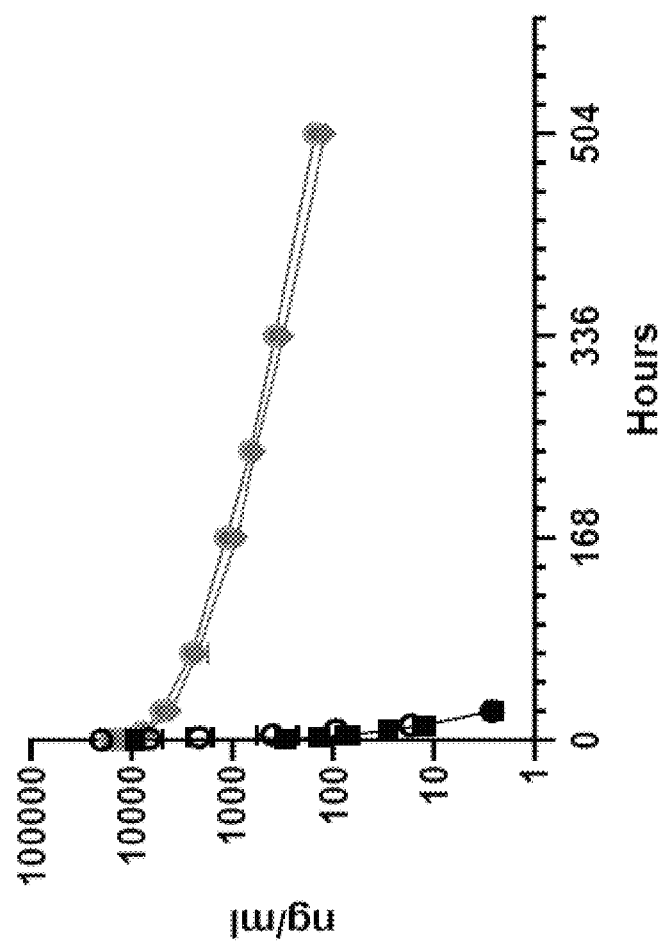
Figure 3B:
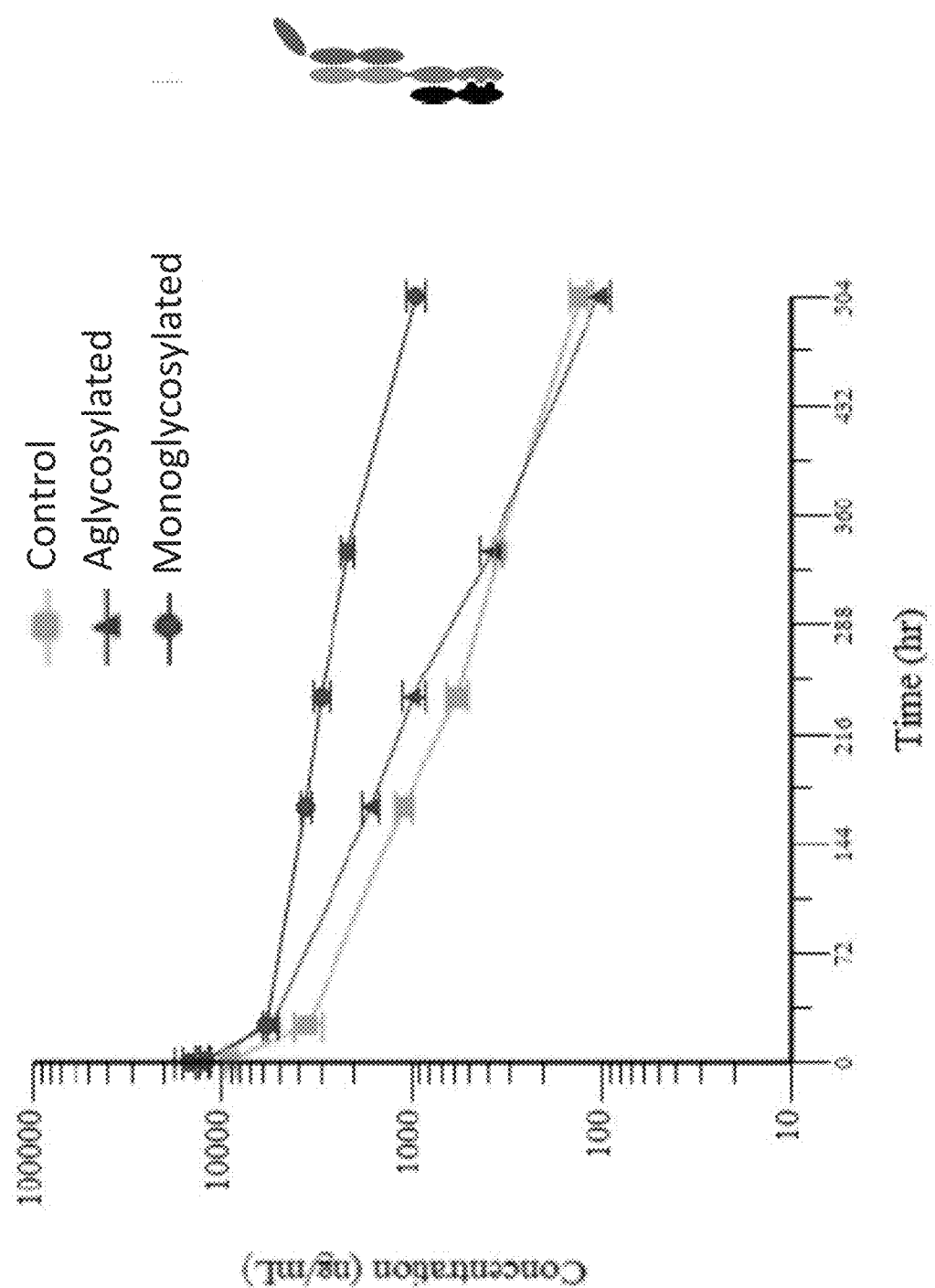

These TCR:anti-CD3 fusion molecules included an antibody Fc domain because this was found to substantially improve in vivo pharmacokinetic properties in the SCID mouse model described above. Formats with the Fc domain fused to the alpha or beta chain were found to have substantially improved pharmacokinetics, as compared to similar molecules without an Fc expressed from E. coli or CHO cells (FIG. 3A and Table A). All N-glycosylation sites for these molecules were intact. The format shown in FIG. 1B (with scFv on the N-terminus of the TCR beta chain and Fc on the C-terminus of the alpha chain) had the most favorable pharmacokinetic properties. Fusing the Fc to the C-terminus of the alpha chain also resulted in a molecule with the highest activity (i.e., potency and selectivity) among various formats tested. This format was selected for further testing.

TABLE A

Pharmacokinetics of TCR:anti-CD3 fusion molecules.

| Molecule | Cmax (ng/ml) | AUCinf (hr*ng/mL) | CL (mL/hr/kg) | $T_{1/2}$ (hr) |
| --- | --- | --- | --- | --- |
| No Fc from E. coli | 20300 | 22600 | 45.2 | 3.4 |
| No Fc from CHO | 9400 | 6210 | 163 | 4.7 |
| Fc on beta chain | 15300 | 61400 | 1.64 | 105 |
| Fc on alpha chain | 15900 | 72300 | 1.38 | 108 |

Different linker sequences were also tested in this format. No difference was observed in production yield using different linker sequences. In addition, molecules with different linkers showed comparable potency and levels of off-target activity. Finally, molecules with different linkers exhibited equivalent stability in serum. These results demonstrate that linker sequence did not affect activity, yield, or serum stability.

Figure 3C:
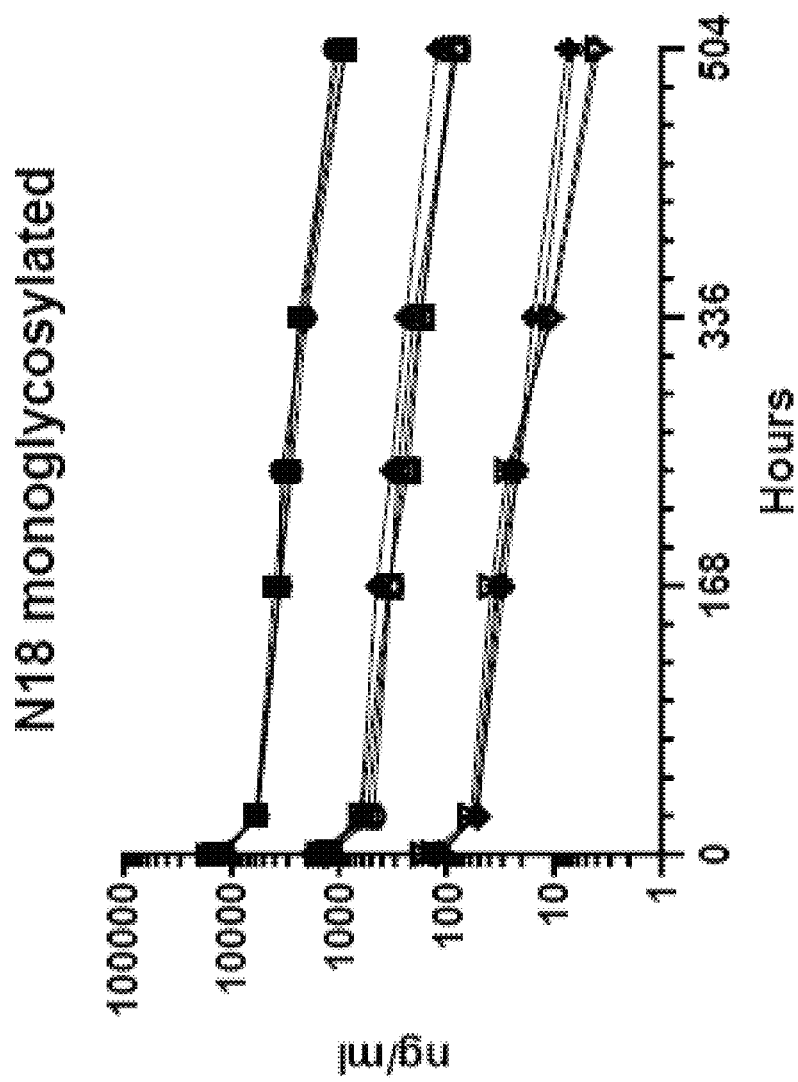
Figure 3D:
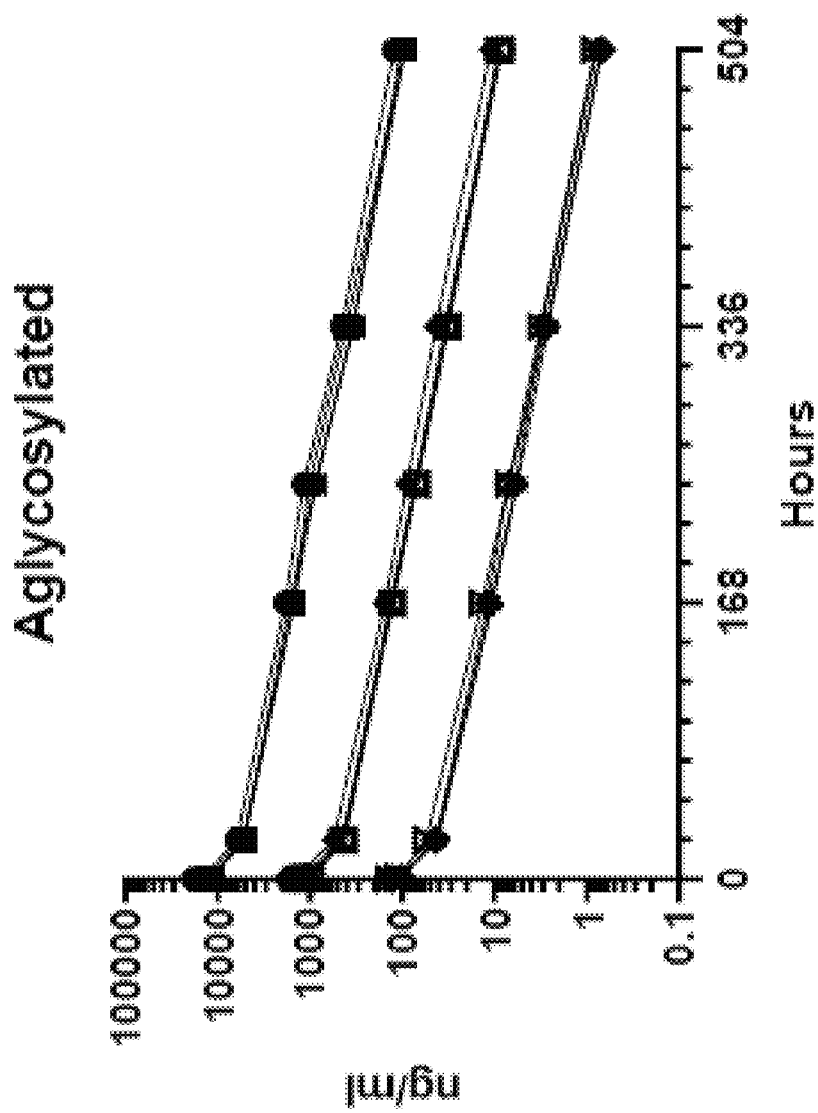

To further improve pharmacokinetics, aglycosylated and monoglycosylated variants of the same TCR:anti-CD3 fusion molecule (as shown in FIG. 2B) were generated and tested for in vivo pharmacokinetic properties in the SCID mouse model. As shown in FIGS. 3B-3E, the monoglycosylated variant showed better pharmacokinetic properties, including slower elimination, half-life, and clearance, as compared to the aglycosylated form. The monoglycosylated form showed substantially slower elimination (FIGS. 3B & 3E), while the pharmacokinetics were close to linear across a 100-fold dose range for both forms (FIGS. 3C & 3D). Thus, the monoglycosylated form with a single N-linked glycosylation site at N18 of the alpha chain variable region showed improved half-life, as compared to the aglycosylated form.

Both variants were also subjected to stability testing. For thermal stress testing, the aglycosylated and monoglycosylated variants of the same TCR:anti-CD3 fusion molecule (as shown in FIG. 2B) were exposed to 30° C. heat stress for 4 weeks at 1 mg/mL in 20 mM His-Acetate and 240 mM sucrose, pH 5.5. After incubation the monoglycosylated form showed an increase of 0.8% monomer loss by SEC, whereas the aglycosylated form showed a significantly higher 11.3% monomer loss (+6.1% vHMW forms and 4.8% dimer). Both forms demonstrated stability at all potential deamidation/isomerization sites.

Both forms were also subjected to thermal stress of 37° C. for 2 weeks at 1 mg/mL in PBS, pH 7.4. After incubation the aglycosylated molecule displayed an increase of 7.3% (4.1% vHMW forms, 1.7% dimer), while the monomer loss of the monoglycosylated was only 1.4%. Both forms demonstrated almost no change at all potential deamidation/isomerization sites.

In summary, the aglycosylated and monoglycosylated forms were found to have substantially different stability. These results demonstrated that the monoglycosylated form had better resistance to thermal stress than the aglycosylated form. Both forms also demonstrated stability at each potential oxidation site on the anti-CD3 scFv in an AAPH oxidation assay. Taken together, these results demonstrate that the glycan at position N18 in the alpha chain variable domain is critical to prevent aggregation, and suggest that the monoglycosylated form has a more preferable manufacturability profile than the aglycosylated form.

Binding affinity was also measured for aglycosylated and monoglycosylated variants. Both forms had similar affinity to MAGEA4 peptide via the TCR as measured by BIACORE, with monoglycosylated variant having a $K_D$ of 0.17 nM, and aglycosylated variant having a $K_D$ of 0.18 nM.

The affinity of aglycosylated and monoglycosylated molecules based on the anti-CD3scFv U28 variant and the original UCHT1v9 were measured via Biacore to human CD3ε. Both U28 based molecules had comparable affinity to CD3ε (14 nM $K_D$ for aglycosylated; 15 nM $K_D$ for monoglycosylated). The UCHT1v9 based molecules also had comparable affinity for CD3 (17 nM $K_D$ for aglycosylated; 18 nM $K_D$ for monoglycosylated). While the equilibrium affinity of the U28 based molecules was similar to the original UCHT1v9 based molecules, the anti-CD3 scFv were characterized with slightly different binding kinetics (U28~2-fold faster on- and off-rates).

In summary, the affinity of pMHC binding was not altered by the presence or absence of glycosylation.

Example 2: Potency and Selectivity of Monoglycosylated or Aglycosylated TCR:Anti-CD3 Fusion Molecules The aglycosylated and monoglycosylated TCR:anti-CD3 fusion molecules described in Example 1 were tested for potency and selectivity of target cell killing.

Materials and Methods

Cell Killing

Figure 4B:
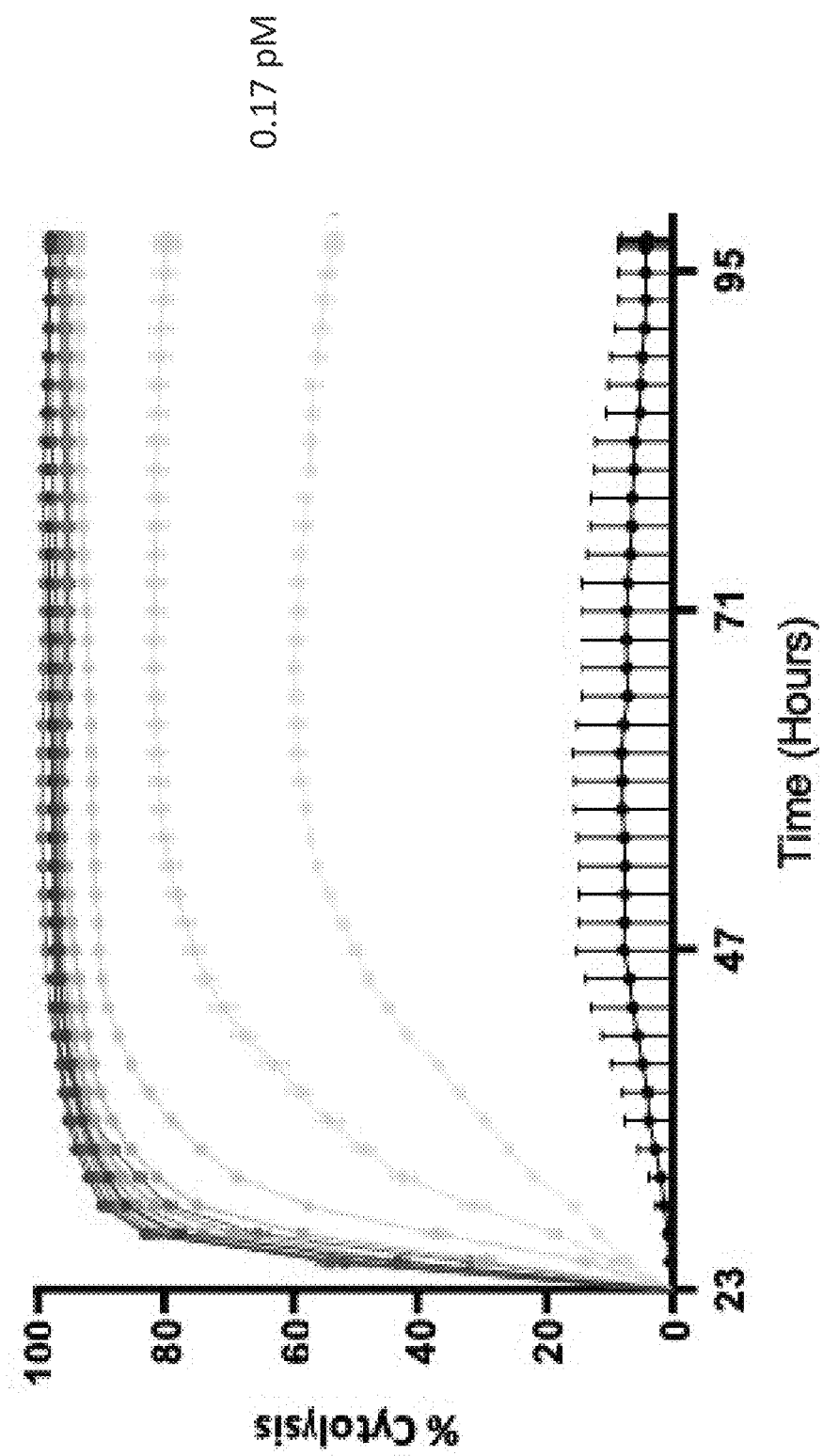
Figure 4C:
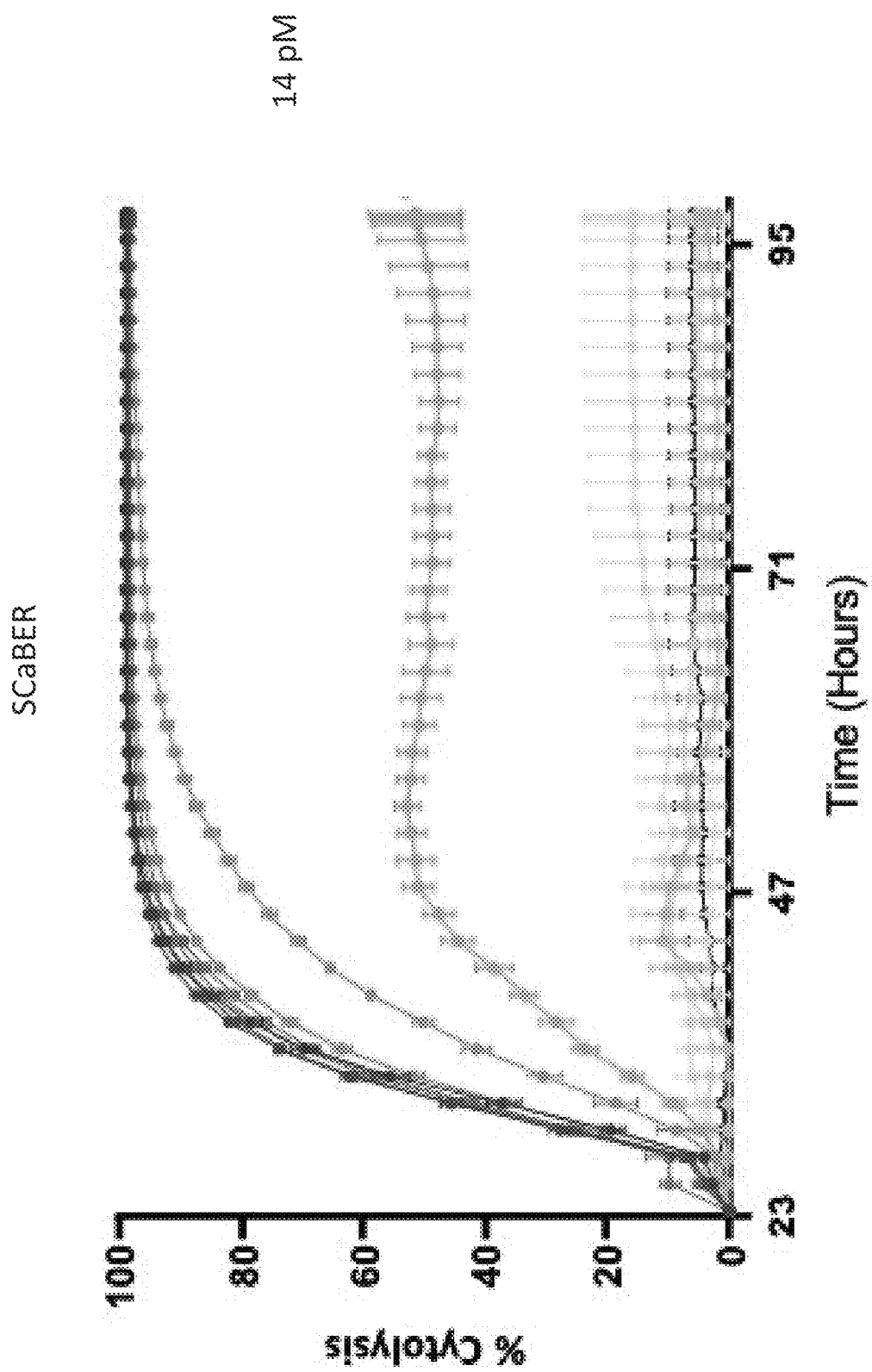
Figure 4D:
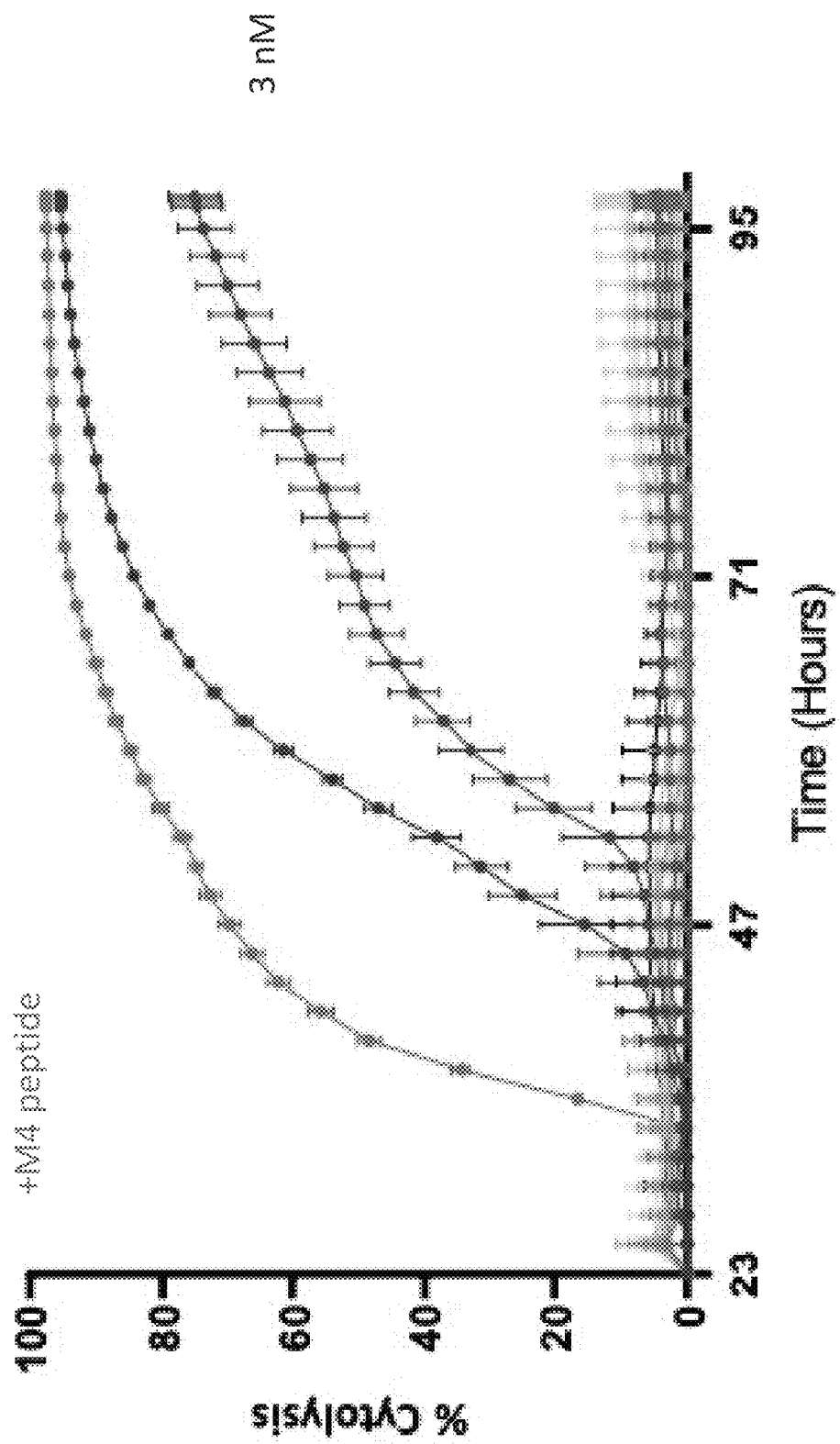

For FIGS. 4B-4D, assays were performed using the xCELLigence platform (Agilent). Effector cells were used at an effector target cell ratio of 10:1 The percentage of cytolysis was determined using the normalized cell index (impedance measurement). In all cases, assays were performed in triplicate measurements taken every 2 hours over 96 hours. EC50 values were derived from percent cytolysis curves at 72 hours. Curve fitting was performed in PRISM.

Figure 5A:
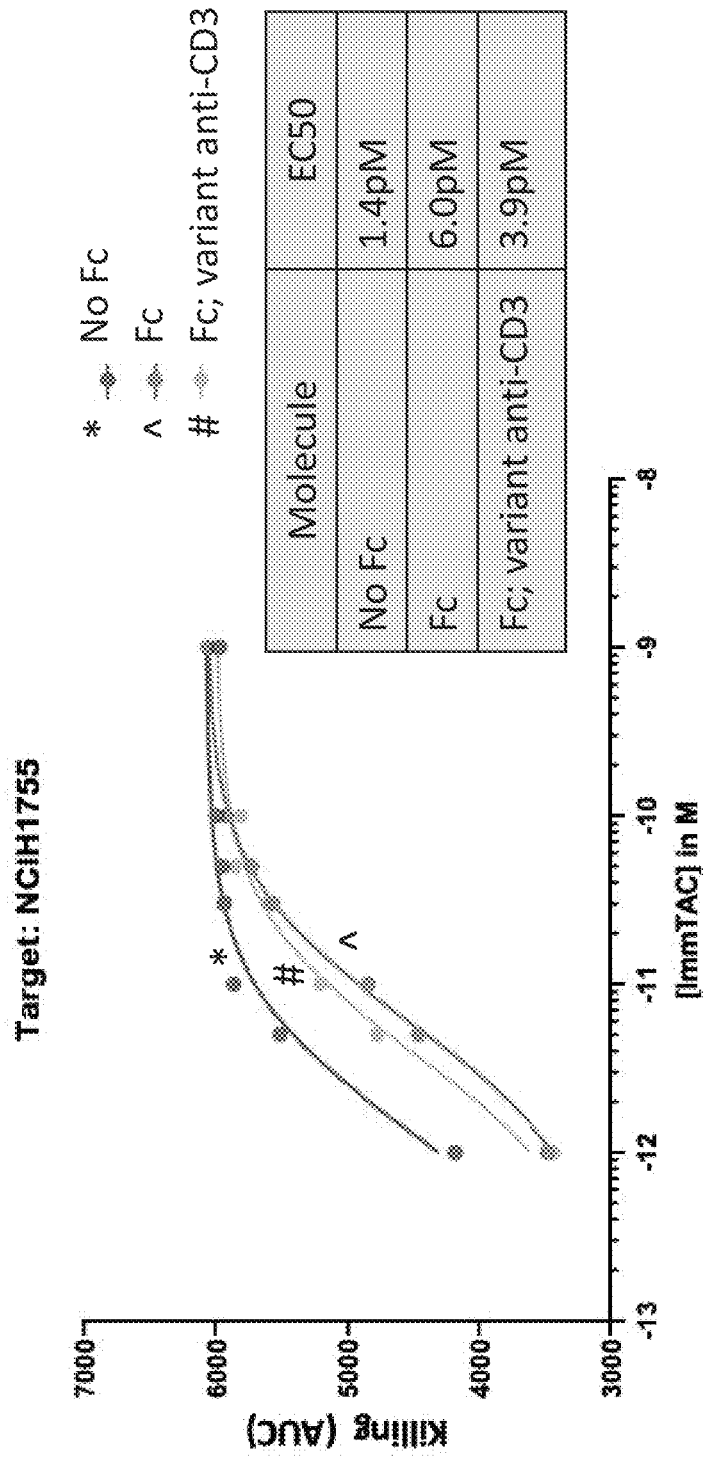
FIGS. 5A-5C show potency loss upon fusion of an Fc, which is partially offset by using a variant anti-CD3 scFv.
Figure 5B:
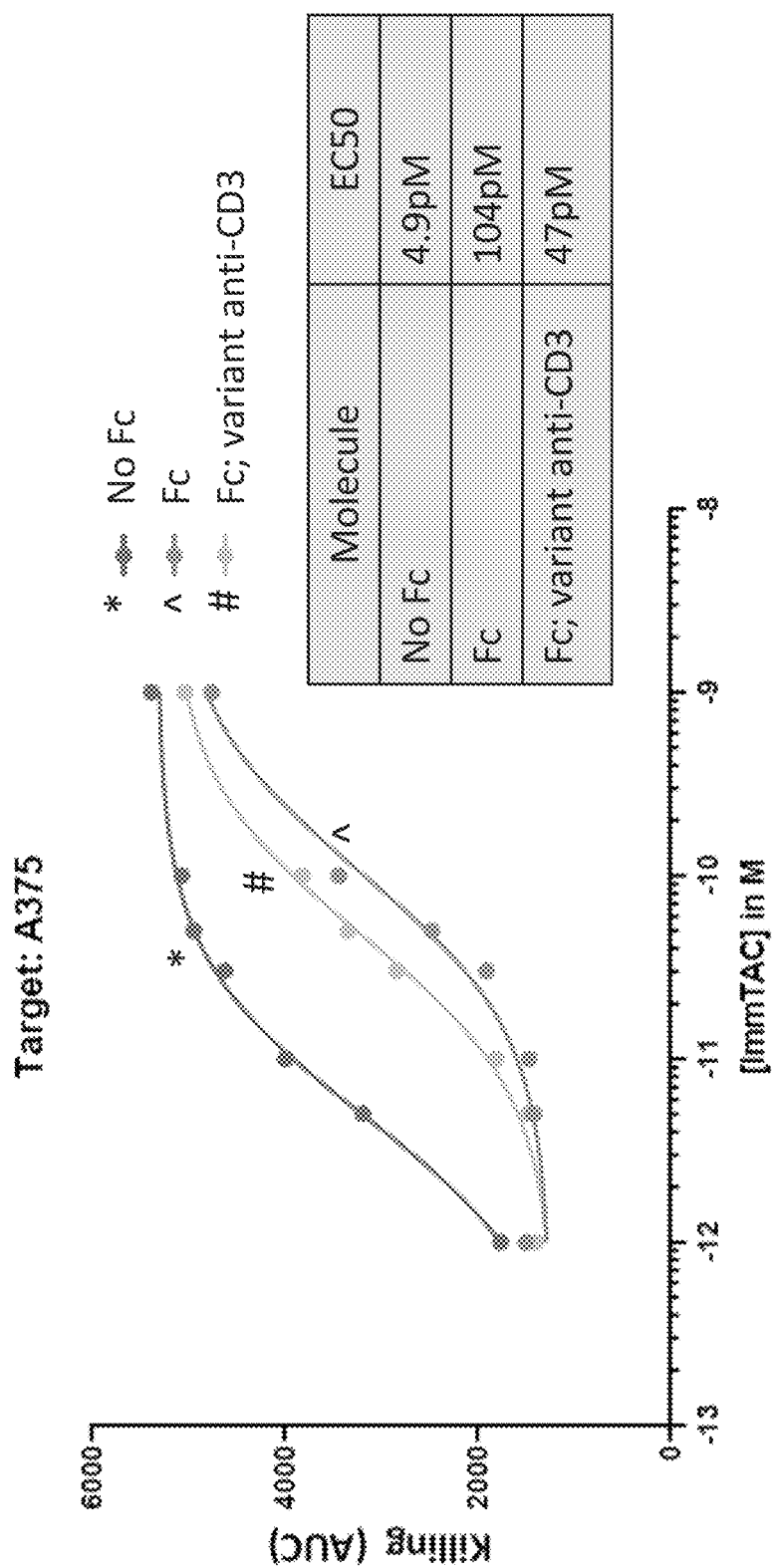

For FIGS. 5A & 5B, assays were performed using an Opera Phenix high content screening system (Perkin Elmer). Effector cells were used at an effector target cell ratio of 5:1 AUC values were obtained and curve fitting was performed in PRISM. EC50 values were calculated from the curves.

Figure 5C:
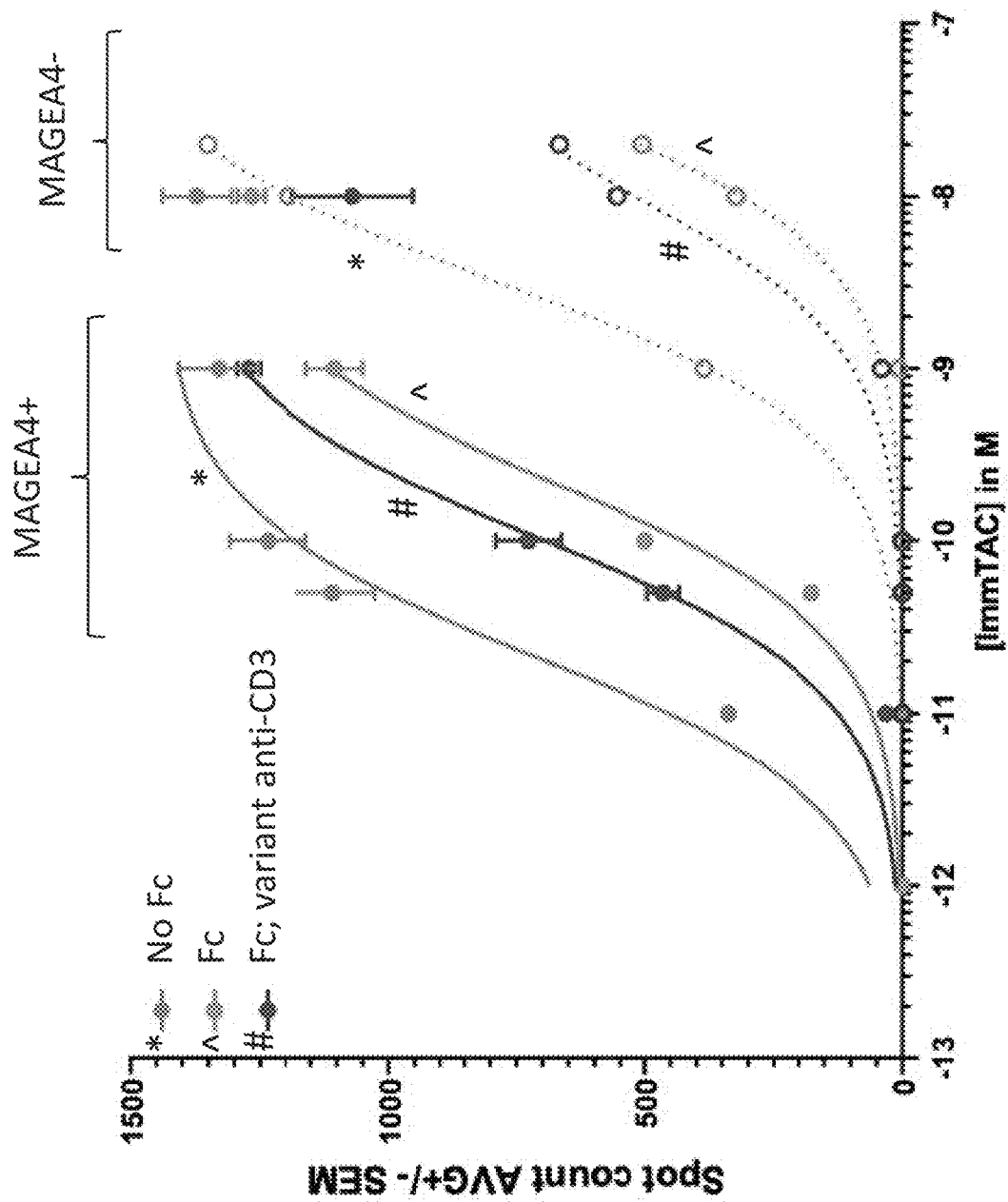

For FIG. 5C, assays were performed using a human IFN-7 ELISpot kit (BD Biosciences). Target cells were prepared at a density of 1×10⁶/ml in assay medium and plated at 50,000 cells per well in a volume of 50 µl. PBMCs isolated from fresh donor blood, were used as effector cells. Effector cells were used at an effector target cell ratio of 1:1 for antigen positive cells and 0.8:1 for antigen negative cells. Samples were detected using AEC chromagen. Spot counting was performed using a CTL analyser with Immunospot software (Cellular Technology Limited). Curve fitting was performed in PRISM and EC50 values calculated.

MAGEA4 antigen copy number was determined by quantitative mass spectrometry.

Results

A variety of cancer cell lines were used, representing a range of target MAGE-A4 antigen expression. All cell lines expressed HLA-A2. EC50 values for cytolysis against all cell lines are shown in FIG. 4A and were calculated from data obtained at the 72 hour timepoint. Killing curves and the lowest concentration of TCR:anti-CD3 fusion molecule that gave rise to a killing response are shown in FIGS. 4B-4D. Both aglycosylated and monoglycosylated TCR:anti-CD3 fusion molecules demonstrated low pM cell killing activity and selectivity. For example, cell killing against NCI-H1755 lung adenocarcinoma cells (which had the highest MAGE-A4 expression) was observed at a TCR:anti-CD3 fusion molecule concentration of 0.17 pM for both molecules (FIG. 4B). Cell killing against SCaBER bladder urothelial carcinoma cells (which an intermediate level of MAGE-A4 expression) was observed at a TCR:anti-CD3 fusion molecule concentration of 14 pM for both molecules (FIG. 4C). In contrast, cell killing against NCI-H441 cells (which are MAGE-A4 negative but HLA-A2 positive) was observed at a TCR:anti-CD3 fusion molecule concentration of 3 nM (FIG. 4D), indicating that selectivity was retained until the nM level. Thus, killing activity was associated with target (pMHC) copy number. These results indicate high potency and selectivity for both molecules.

TCR:anti-CD3 fusion molecules with an Fc fusion as described above were found to have reduced potency of cell killing against target cells expressing MAGE-A4 antigen: HLA complexes (FIGS. 5A & 5B). However, as shown in FIG. 3A, inclusion of the Fc domain was desirable in order to improve in vivo pharmacokinetics. As such, a variant anti-CD3 scFv was tested. As noted above, this variant included point mutations in CDR-H1 and FR3. It was found that the potency loss upon using an Fc fusion was offset by use of the variant anti-CD3 scFv (FIGS. 5A & 5B). Against antigen-positive cancer cells, the EC50 of cell killing of the TCR:anti-CD3 fusion molecule with Fc fusion and variant anti-CD3 scFv was within 3-10 fold of the molecule without an Fc domain.

All three molecules showed a reduction in reactivity to antigen(−) cells, similar to the reduction in potency on antigen(+) cells (FIG. 5C). These results demonstrate that the window between on-target and off-target activity was maintained for all three TCR:anti-CD3 fusion molecules tested.

Example 3: In Vitro Safety Testing of Monoglycosylated TCR:Anti-CD3 Fusion Molecules The monoglycosylated TCR:anti-CD3 fusion molecule described in Example 1 was tested in vitro for safety against normal cell lines.

Materials and Methods

In Vitro Safety Testing

For testing against normal cells, reactivity was determined by ELISpot assay to detect release of IFNγ and Granzyme B. The lowest concentration of TCR-antiCD3 fusion molecule at which each cytokine was detected was recorded. For alloreactivity (i.e. binding to alternative HLA), reactivity was assessed using IFNγ ELISpot assay against as a 6-cell lot panel covering the 5 most prevalent HLA-As (other than HLA*02:01), 4 HLA-Bs and 6 HLA-Cs in the global population. Whole blood assays were performed using the Proinflammatory Panel 1 (human) kit (Meso Scale Discovery) for detection of TNFα, IL-2, IL-6, IL-1β, IFNγ in whole blood obtained from three donors. TCR-antiCD3 fusion was applied at various concentrations between 0.01-10 nM.

Results

Figure 6A:
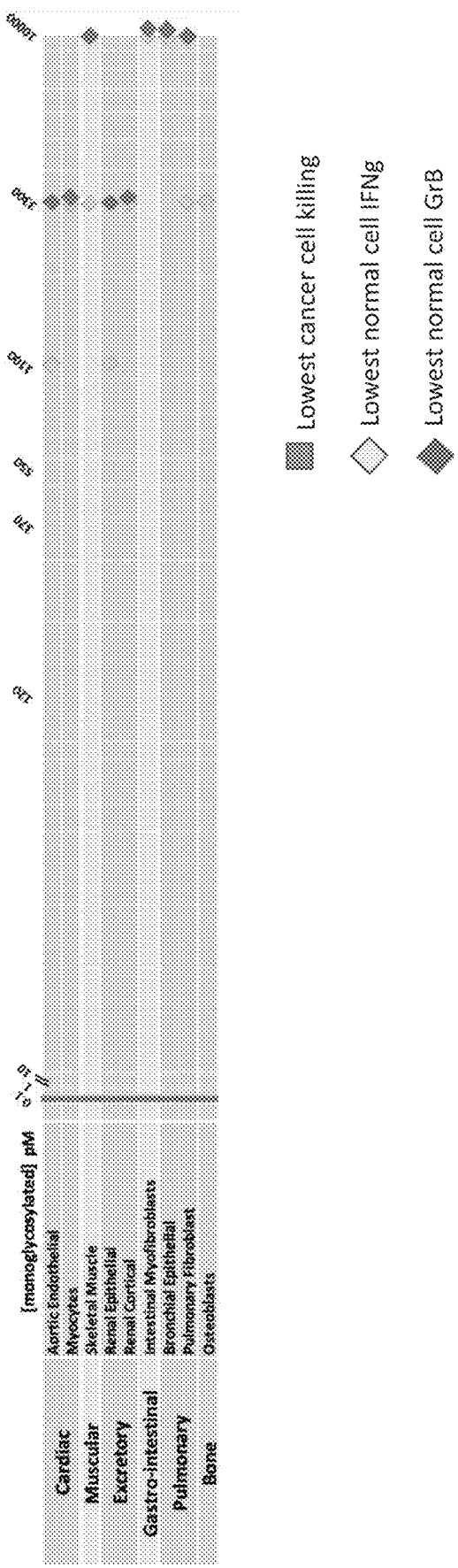
FIGS. 6A & 6B show the results of in vitro safety assays examining TCR:anti-CD3 fusion molecules.

The monoglycosylated TCR:anti-CD3 fusion molecule was tested in panel of normal cell lines covering high risk tissue types, as well as cell types that had demonstrated reactivity to anti-MAGE-A4 TCR. No detectable reactivity against normal cells was observed in a 6 cell panel covering 15 most frequent HLA types, using IFNγ as a readout (FIG. 6A). In a whole blood assay, no cytokine release was observed at less than nM concentrations. In summary, no reactivity against normal cell lines was detected at less than nM concentrations, demonstrating safety in this in vitro assay.

Figure 6B:
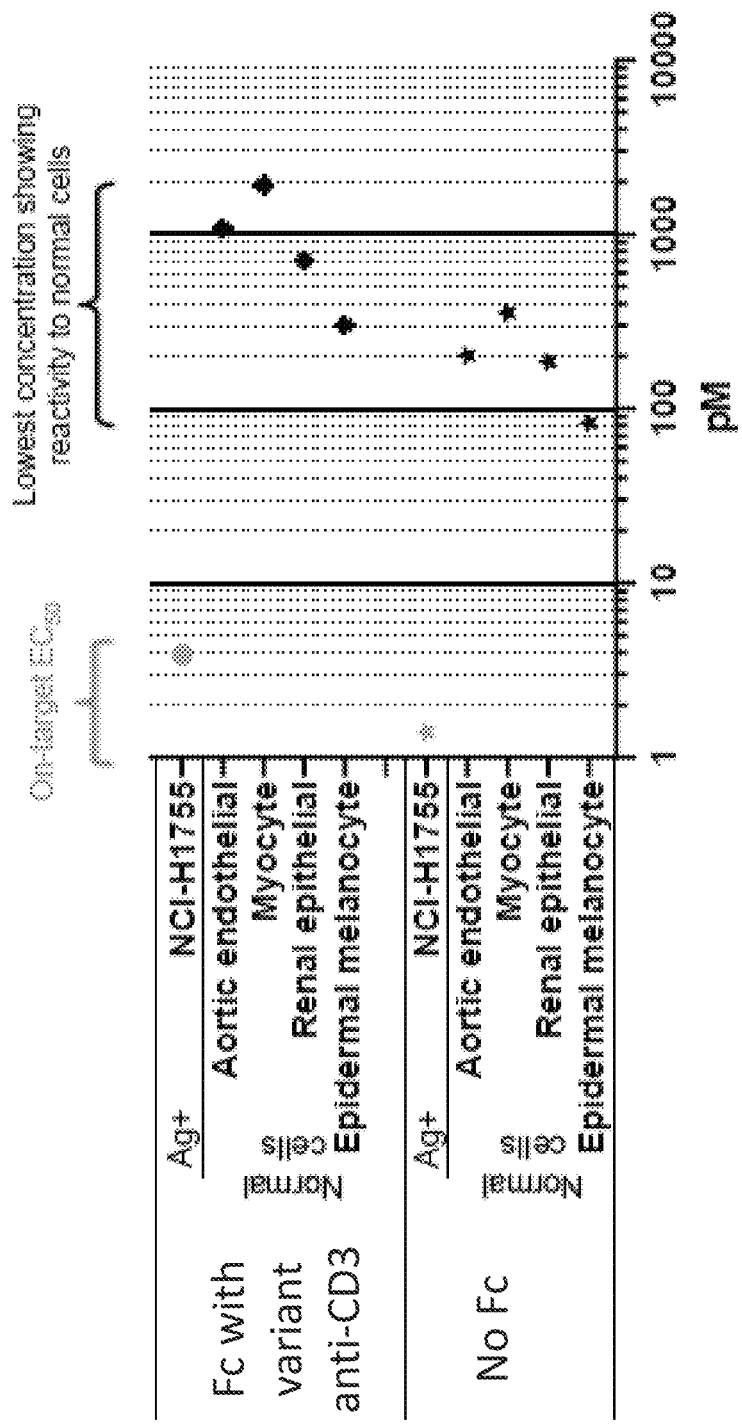

Comparing TCR:anti-CD3 fusion molecule with variant anti-CD3 scFv with TCR:anti-CD3 fusion molecule having no Fc again showed that the window in potency between on-target and off-target activity on normal cells was maintained (FIG. 6B). This demonstrates that the TCR:anti-CD3 fusion molecule with Fc domain and variant anti-CD3 scFv maintained equivalent therapeutic index to the form without an Fc fusion.

SEQUENCES

Anti-MAGE-A4 TCR Vα CDR-1
VSPFSN (SEQ ID NO: 1)

Anti-MAGE-A4 TCR Vα CDR-2
LTFSENT (SEQ ID NO: 2)

SEQUENCES

Anti-MAGE-A4 TCR Vα CDR-3
VVNSAQGLYIPTF (SEQ ID NO: 3)

Anti-MAGE-A4 TCR Vβ CDR-1
LDHEN (SEQ ID NO: 4)

Anti-MAGE-A4 TCR Vβ CDR-2
SRFATG (SEQ ID NO: 5)

Anti-MAGE-A4 TCR Vβ CDR-3
ASSSDQNSGDPYEQYF (SEQ ID NO: 6)

Anti-MAGE-A4 TCR alpha chain variable region (monoglycosylated form)
ANQVEQSPQSLIILEGKNVTLQCQYTVSPFSNLRWYKQDTGRGPVSLTILTFSENTKSNGRYTATLDADTKQ
SSLHITASQLSDSASYICVVNSAQGLYIPTFGRGTSLIVHP (SEQ ID NO: 7)

Anti-MAGE-A4 TCR alpha chain variable region (aglycosylated form)
ANQVEQSPQSLIILEGKQVTLQCQYTVSPFSNLRWYKQDTGRGPVSLTILTFSENTKSNGRYTATLDADTKQ
SSLHITASQLSDSASYICVVNSAQGLYIPTFGRGTSLIVHP (SEQ ID NO: 8)

Anti-MAGE-A4 TCR alpha chain constant region (monoglycosylated or aglycosylated form)
YIQKPDPAVYQLRDSKSSDKSVCLFTDFDSQTQVSQSKDSDVYITDKCVLDMRSMDFKSNSAVAWSQKSD
FACANAFQNSIIPEDT (SEQ ID NO: 9)

Parental anti-MAGE-A4 TCR alpha chain constant region (fully glycosylated form)
YIQKPDPAVYQLRDSKSSDKSVCLFTDFDSQTNVSQSKDSDVYITDKCVLDMRSMDFKSNSAVAWSNKSD
FACANAFNNSIIPEDT (SEQ ID NO: 10)

Anti-MAGE-A4 TCR alpha chain (monoglycosylated form)
ANQVEQSPQSLIILEGKNVTLQCQYTVSPFSNLRWYKQDTGRGPVSLTILTFSENTKSNGRYTATLDADTKQ
SSLHITASQLSDSASYICVVNSAQGLYIPTFGRGTSLIVHPYIQKPDPAVYQLRDSKSSDKSVCLFTDFDSQTQ
VSQSKDSDVYITDKCVLDMRSMDFKSNSAVAWSQKSDFACANAFQNSIIPEDT (SEQ ID NO: 11)

Anti-MAGE-A4 TCR alpha chain (aglycosylated form)
ANQVEQSPQSLIILEGKQVTLQCQYTVSPFSNLRWYKQDTGRGPVSLTILTFSENTKSNGRYTATLDADTKQ
SSLHITASQLSDSASYICVVNSAQGLYIPTFGRGTSLIVHPYIQKPDPAVYQLRDSKSSDKSVCLFTDFDSQTQ
VSQSKDSDVYITDKCVLDMRSMDFKSNSAVAWSQKSDFACANAFQNSIIPEDT (SEQ ID NO: 12)

Anti-MAGE-A4 TCR beta chain variable region (monoglycosylated or aglycosylated form)
DVKVTQSSRYLVKRTGEKVFLECVQDLDHENMFWYRQDPGLGLRLIYFSRFATGKEKGDIPEGYSVSREK
KERFSLILESASTQQTSMYLCASSSDQNSGDPYEQYFGPGTRLTVT (SEQ ID NO: 13)

Anti-MAGE-A4 TCR beta chain constant region (monoglycosylated or aglycosylated form)
EDLKNVFPPEVAVFEPSEAEISHTQKATLVCLATGFYPDHVELSWWVNGKEVHSGVCTDPQPLKEQPALQ
DSRYALSSRLRVSATFWQDPRNHFRCQVQFYGLSENDEWTQDRAKPVTQIVSAEAWGRAD (SEQ ID NO: 14)

Parental anti-MAGE-A4 TCR beta chain constant region (fully glycosylated form)
EDLKNVFPPEVAVFEPSEAEISHTQKATLVCLATGFYPDHVELSWWVNGKEVHSGVCTDPQPLKEQPALN
DSRYALSSRLRVSATFWQDPRNHFRCQVQFYGLSENDEWTQDRAKPVTQIVSAEAWGRAD (SEQ ID NO: 15)

Anti-MAGE-A4 TCR beta chain (monoglycosylated or aglycosylated form)
DVKVTQSSRYLVKRTGEKVFLECVQDLDHENMFWYRQDPGLGLRLIYFSRFATGKEKGDIPEGYSVSREK
KERFSLILESASTQQTSMYLCASSSDQNSGDPYEQYFGPGTRLTVTEDLKNVFPPEVAVFEPSEAEISHTQKA
TLVCLATGFYPDHVELSWWVNGKEVHSGVCTDPQPLKEQPALQDSRYALSSRLRVSATFWQDPRNHFRC
QVQFYGLSENDEWTQDRAKPVTQIVSAEAWGRAD (SEQ ID NO: 16)

Anti-CD3 scFv U28 variant
AIQMTQSPSSLSASVGDRVTITCRASQDIRNYLNWYQQKPGKAPKLLIYYTSRLESGVPSRFSGSGSGTDYT
LTISSLQPEDFATYYCQQGNTLPWTFGQGTKVEIKGGGGSGGGGSGGGGSGGGGSGGGSEVQLVESGGGL
VQPGGSLRLSCAASGYSFTGYAMNWVRQAPGKGLEWVALINPYKGVSTYNQKFKDRFTFSVDKSKNTAY
LQMNSLRAEDTAVYYCARSGYYGDSDWYFDVWGQGTLVTVSS (SEQ ID NO: 17)

Linker
GGGGS (SEQ ID NO: 18)

Linker
GGGSG (SEQ ID NO: 19)

Linker
GGSGG (SEQ ID NO: 20)

Linker
GSGGG (SEQ ID NO: 21)

Linker
GSGGGP (SEQ ID NO: 22)

| SEQUENCES |
| --- |

Linker
GGEPS (SEQ ID NO: 23)

Linker
GGEGGGP (SEQ ID NO: 24)

Linker
GGEGGGSEGGGS (SEQ ID NO: 25)

Fc domain with knob mutation
DKTHTCPPCPAPELLGGPSVFLFPPKPKDTLMISRTPEVTCVVVDVSHEDPEVKFNWYVDGVEVHNAKTKP
REEQYGSTYRVVSVLTVLHQDWLNGKEYKCKVSNKALPAPIEKTISKAKGQPREPQVYTLPPSRDELTKNQ
VSLWCLVKGFYPSDIAVEWESNGQPENNYKTTPPVLDSDGSFFLYSKLTVDKSRWQQGNVFSCSVMHEAL
HNHYTQKSLSLSPGK (SEQ ID NO: 26)

Fc domain with hole mutations
DKTHTCPPCPAPELLGGPSVFLFPPKPKDTLMISRTPEVTCVVVDVSHEDPEVKFNWYVDGVEVHNAKTKP
REEQYGSTYRVVSVLTVLHQDWLNGKEYKCKVSNKALPAPIEKTISKAKGQPREPQVYTLPPSRDELTKNQ
VSLSCAVKGFYPSDIA VEWESNGQPENNYKTTPPVLDSDGSFFLVSKLTVDKSRWQQGNVFSCSVMHEAL
HNHYTQKSLSLSPGK (SEQ ID NO: 27)

Monoglycosylated Anti-MAGE-A4 TCR: anti-CD3 scFv Fc fusion chain 1 (Fc with knob
mutation)
DKTHTCPPCPAPELLGGPSVFLFPPKPKDTLMISRTPEVTCVVVDVSHEDPEVKFNWYVDGVEVHNAKTKP
REEQYGSTYRVVSVLTVLHQDWLNGKEYKCKVSNKALPAPIEKTISKAKGQPREPQVYTLPPSRDELTKNQ
VSLWCLVKGFYPSDIAVEWESNGQPENNYKTTPPVLDSDGSFFLYSKLTVDKSRWQQGNVFSCSVMHEAL
HNHYTQKSLSLSPG (SEQ ID NO: 28)

Monoglycosylated Anti-MAGE-A4 TCR: anti-CD3 scFv Fc fusion chain 2 (TCR alpha chain
fused to Fc with hole mutations)
ANQVEQSPQSLIILEGKNVTLQCQYTVSPFSNLRWYKQDTGRGPVSLTILTFSENTKSNGRYTATLDADTKQ
SSLHITASQLSDSASYICVVNSAQGLYIPTFGRGTSLIVHPYIQKPDPAVYQLRDSKSSDKSVCLFTDFDSQTQ
VSQSKDSDVYITDKCVLDMRSMDFKSNSAVAWSQKSDFACANAFQNSIIPEDTDKTHTCPPCPAPELLGGP
SVFLFPPKPKDTLMISRTPEVTCVVVDVSHEDPEVKFNWYVDGVEVHNAKTKPREEQYGSTYRVVSVLTV
LHQDWLNGKEYKCKVSNKALPAPIEKTISKAKGQPREPQVYTLPPSRDELTKNQVSLSCAVKGFYPSDIAV
EWESNGQPENNYKTTPPVLDSDGSFFLVSKLTVDKSRWQQGNVFSCSVMHEALHNHYTQKSLSLSPG
(SEQ ID NO: 29)

Monoglycosylated Anti-MAGE-A4 TCR: anti-CD3 scFv Fc fusion chain 3 (variant anti-CD3
scFv fused to TCR beta chain)
AIQMTQSPSSLSASVGDRVTITCRASQDIRNYLNWYQQKPGKAPKLLIYYTSRLESGVPSRFSGSGSGTDYT
LTISSLQPEDFATYYCQQGNTLPWTFGQGTKVEIKGGGGSGGGGSGGGGSGGGGSGGGSEVQLVESGGGL
VQPGGSLRLSCAASGYSFTGYAMNWVRQAPGKGLEWVALINPYKGVSTYNQKFKDRFTFSVDKSKNTAY
LQMNSLRAEDTAVYYCARSGYYGDSDWYFDVWGQGTLVTVSSGGGGSDVKVTQSSRYLVKRTGEKVFL
ECVQDLDHENMFWYRQDPGLGLRLIYFSRFATGKEKGDIPEGYSVSREKKERFSLILESASTQQTSMYLCAS
SSDQNSGDPYEQYFGPGTRLTVTEDLKNVFPPEVAVFEPSEAEISHTQKATLVCLATGFYPDHVELSWWVN
GKEVHSGVCTDPQPLKEQPALQDSRYALSSRLRVSATFWQDPRNHFRCQVQFYGLSENDEWTQDRAKPVT
QIVSAEAWGRAD (SEQ ID NO: 30)

Hinge sequence
DKTHTCPP (SEQ ID NO: 31) or DKTHTCPPC (SEQ ID NO: 36)

Anti-MAGE-A4 TCR alpha variable chain (fully glycosylated form)
ANQVEQSPQSLIILEGKNVTLQCNYTVSPFSNLRWYKQDTGRGPVSLTILTFSENTKSNGRYTATLDADTKQ
SSLHITASQLSDSASYICVVNSAQGLYIPTFGRGTSLIVHP (SEQ ID NO: 32)

Anti-MAGE-A4 TCR beta variable chain (fully glycosylated form)
DVKVTQSSRYLVKRTGEKVFLECVQDLDHENMFWYRQDPGLGLRLIYFSRFATGKEKGDIPEGYSVSREK
KERFSLILESASTNQTSMYLCASSSDQNSGDPYEQYFGPGTRLTVT (SEQ ID NO: 33)

MAGE-A4 target antigen
GVYDGREHTV (SEQ ID NO: 34)

Anti-CD3 scFv (parental)
AIQMTQSPSSLSASVGDRVTITCRASQDIRNYLNWYQQKPGKAPKLLIYYTSRLESGVPSRFSGSGSG
TDYTLTISSLQPEDFATYYCQQGNTLPWTFGQGTKVEIKGGGGSGGGGSGGGGSGGGGSGGGSEVQLV
ESGGGLVQPGGSLRLSCAASGYSFTGYTMNWVRQAPGKGLEWVALINPYKGVSTYNQKFKDRFTISVD
KSKNTAYLQMNSLRAEDTAVYYCARSGYYGDSDWYFDVWGQGTLVTVSS (SEQ ID NO: 35)

| SEQUENCE LISTING |
| --- |

Sequence total quantity: 36
SEQ ID NO: 1          moltype = AA   length = 6

```
FEATURE                 Location/Qualifiers
source                  1..6
                        mol_type = protein
                        organism = synthetic construct
SEQUENCE: 1
VSPFSN                                                                    6

SEQ ID NO: 2            moltype = AA  length = 7
FEATURE                 Location/Qualifiers
source                  1..7
                        mol_type = protein
                        organism = synthetic construct
SEQUENCE: 2
LTFSENT                                                                   7

SEQ ID NO: 3            moltype = AA  length = 13
FEATURE                 Location/Qualifiers
source                  1..13
                        mol_type = protein
                        organism = synthetic construct
SEQUENCE: 3
VVNSAQGLYI PTF                                                           13

SEQ ID NO: 4            moltype = AA  length = 5
FEATURE                 Location/Qualifiers
source                  1..5
                        mol_type = protein
                        organism = synthetic construct
SEQUENCE: 4
LDHEN                                                                     5

SEQ ID NO: 5            moltype = AA  length = 6
FEATURE                 Location/Qualifiers
source                  1..6
                        mol_type = protein
                        organism = synthetic construct
SEQUENCE: 5
SRFATG                                                                    6

SEQ ID NO: 6            moltype = AA  length = 16
FEATURE                 Location/Qualifiers
source                  1..16
                        mol_type = protein
                        organism = synthetic construct
SEQUENCE: 6
ASSSDQNSGD PYEQYF                                                        16

SEQ ID NO: 7            moltype = AA  length = 113
FEATURE                 Location/Qualifiers
source                  1..113
                        mol_type = protein
                        organism = synthetic construct
SEQUENCE: 7
ANQVEQSPQS LIILEGKNVT LQCQYTVSPF SNLRWYKQDT GRGPVSLTIL TFSENTKSNG         60
RYTATLDADT KQSSLHITAS QLSDSASYIC VVNSAQGLYI PTFGRGTSLI VHP               113

SEQ ID NO: 8            moltype = AA  length = 113
FEATURE                 Location/Qualifiers
source                  1..113
                        mol_type = protein
                        organism = synthetic construct
SEQUENCE: 8
ANQVEQSPQS LIILEGKQVT LQCQYTVSPF SNLRWYKQDT GRGPVSLTIL TFSENTKSNG         60
RYTATLDADT KQSSLHITAS QLSDSASYIC VVNSAQGLYI PTFGRGTSLI VHP               113

SEQ ID NO: 9            moltype = AA  length = 86
FEATURE                 Location/Qualifiers
source                  1..86
                        mol_type = protein
                        organism = synthetic construct
SEQUENCE: 9
YIQKPDPAVY QLRDSKSSDK SVCLFTDFDS QTQVSQSKDS DVYITDKCVL DMRSMDFKSN         60
SAVAWSQKSD FACANAFQNS IIPEDT                                             86

SEQ ID NO: 10           moltype = AA  length = 86
FEATURE                 Location/Qualifiers
source                  1..86
                        mol_type = protein
                        organism = synthetic construct
```

```
SEQUENCE: 10
YIQKPDPAVY QLRDSKSSDK SVCLFTDFDS QTNVSQSKDS DVYITDKCVL DMRSMDFKSN    60
SAVAWSNKSD FACANAFNNS IIPEDT                                        86

SEQ ID NO: 11           moltype = AA   length = 199
FEATURE                 Location/Qualifiers
source                  1..199
                        mol_type = protein
                        organism = synthetic construct
SEQUENCE: 11
ANQVEQSPQS LIILEGKNVT LQCQYTVSPF SNLRWYKQDT GRGPVSLTIL TFSENTKSNG    60
RYTATLDADT KQSSLHITAS QLSDSASYIC VVNSAQGLYI PTFGRGTSLI VHPYIQKPDP   120
AVYQLRDSKS SDKSVCLFTD FDSQTQVSQS KDSDVYITDK CVLDMRSMDF KSNSAVAWSQ   180
KSDFACANAF QNSIIPEDT                                                199

SEQ ID NO: 12           moltype = AA   length = 199
FEATURE                 Location/Qualifiers
source                  1..199
                        mol_type = protein
                        organism = synthetic construct
SEQUENCE: 12
ANQVEQSPQS LIILEGKQVT LQCQYTVSPF SNLRWYKQDT GRGPVSLTIL TFSENTKSNG    60
RYTATLDADT KQSSLHITAS QLSDSASYIC VVNSAQGLYI PTFGRGTSLI VHPYIQKPDP   120
AVYQLRDSKS SDKSVCLFTD FDSQTQVSQS KDSDVYITDK CVLDMRSMDF KSNSAVAWSQ   180
KSDFACANAF QNSIIPEDT                                                199

SEQ ID NO: 13           moltype = AA   length = 116
FEATURE                 Location/Qualifiers
source                  1..116
                        mol_type = protein
                        organism = synthetic construct
SEQUENCE: 13
DVKVTQSSRY LVKRTGEKVF LECVQDLDHE NMFWYRQDPG LGLRLIYFSR FATGKEKGDI    60
PEGYSVSREK KERFSLILES ASTQQTSMYL CASSSDQNSG DPYEQYFGPG TRLTVT       116

SEQ ID NO: 14           moltype = AA   length = 130
FEATURE                 Location/Qualifiers
source                  1..130
                        mol_type = protein
                        organism = synthetic construct
SEQUENCE: 14
EDLKNVFPPE VAVFEPSEAE ISHTQKATLV CLATGFYPDH VELSWWVNGK EVHSGVCTDP    60
QPLKEQPALQ DSRYALSSRL RVSATFWQDP RNHFRCQVQF YGLSENDEWT QDRAKPVTQI   120
VSAEAWGRAD                                                          130

SEQ ID NO: 15           moltype = AA   length = 130
FEATURE                 Location/Qualifiers
source                  1..130
                        mol_type = protein
                        organism = synthetic construct
SEQUENCE: 15
EDLKNVFPPE VAVFEPSEAE ISHTQKATLV CLATGFYPDH VELSWWVNGK EVHSGVCTDP    60
QPLKEQPALN DSRYALSSRL RVSATFWQDP RNHFRCQVQF YGLSENDEWT QDRAKPVTQI   120
VSAEAWGRAD                                                          130

SEQ ID NO: 16           moltype = AA   length = 246
FEATURE                 Location/Qualifiers
source                  1..246
                        mol_type = protein
                        organism = synthetic construct
SEQUENCE: 16
DVKVTQSSRY LVKRTGEKVF LECVQDLDHE NMFWYRQDPG LGLRLIYFSR FATGKEKGDI    60
PEGYSVSREK KERFSLILES ASTQQTSMYL CASSSDQNSG DPYEQYFGPG TRLTVTEDLK   120
NVFPPEVAVF EPSEAEISHT QKATLVCLAT GFYPDHVELS WWVNGKEVHS GVCTDPQPLK   180
EQPALQDSRY ALSSRLRVSA TFWQDPRNHF RCQVQFYGLS ENDEWTQDRA KPVTQIVSAE   240
AWGRAD                                                              246

SEQ ID NO: 17           moltype = AA   length = 253
FEATURE                 Location/Qualifiers
source                  1..253
                        mol_type = protein
                        organism = synthetic construct
SEQUENCE: 17
AIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIKGGG GSGGGGSGGG   120
GSGGGGSGGG SEVQLVESGG GLVQPGGSLR LSCAASGYSF TGYAMNWVRQ APGKGLEWVA   180
LINPYKGVST YNQKFKDRFT FSVDKSKNTA YLQMNSLRAE DTAVYYCARS GYYGDSDWYF   240
DVWGQGTLVT VSS                                                      253
```

```
SEQ ID NO: 18              moltype = AA   length = 5
FEATURE                    Location/Qualifiers
source                     1..5
                           mol_type = protein
                           organism = synthetic construct
SEQUENCE: 18
GGGGS                                                                     5

SEQ ID NO: 19              moltype = AA   length = 5
FEATURE                    Location/Qualifiers
source                     1..5
                           mol_type = protein
                           organism = synthetic construct
SEQUENCE: 19
GGGSG                                                                     5

SEQ ID NO: 20              moltype = AA   length = 5
FEATURE                    Location/Qualifiers
source                     1..5
                           mol_type = protein
                           organism = synthetic construct
SEQUENCE: 20
GGSGG                                                                     5

SEQ ID NO: 21              moltype = AA   length = 5
FEATURE                    Location/Qualifiers
source                     1..5
                           mol_type = protein
                           organism = synthetic construct
SEQUENCE: 21
GSGGG                                                                     5

SEQ ID NO: 22              moltype = AA   length = 6
FEATURE                    Location/Qualifiers
source                     1..6
                           mol_type = protein
                           organism = synthetic construct
SEQUENCE: 22
GSGGGP                                                                    6

SEQ ID NO: 23              moltype = AA   length = 5
FEATURE                    Location/Qualifiers
source                     1..5
                           mol_type = protein
                           organism = synthetic construct
SEQUENCE: 23
GGEPS                                                                     5

SEQ ID NO: 24              moltype = AA   length = 7
FEATURE                    Location/Qualifiers
source                     1..7
                           mol_type = protein
                           organism = synthetic construct
SEQUENCE: 24
GGEGGGP                                                                   7

SEQ ID NO: 25              moltype = AA   length = 12
FEATURE                    Location/Qualifiers
source                     1..12
                           mol_type = protein
                           organism = synthetic construct
SEQUENCE: 25
GGEGGGSEGG GS                                                            12

SEQ ID NO: 26              moltype = AA   length = 227
FEATURE                    Location/Qualifiers
source                     1..227
                           mol_type = protein
                           organism = synthetic construct
SEQUENCE: 26
DKTHTCPPCP APELLGGPSV FLFPPKPKDT LMISRTPEVT CVVVDVSHED PEVKFNWYVD         60
GVEVHNAKTK PREEQYGSTY RVVSVLTVLH QDWLNGKEYK CKVSNKALPA PIEKTISKAK        120
GQPREPQVYT LPPSRDELTK NQVSLWCLVK GFYPSDIAVE WESNGQPENN YKTTPPVLDS        180
DGSFFLYSKL TVDKSRWQQG NVFSCSVMHE ALHNHYTQKS LSLSPGK                      227

SEQ ID NO: 27              moltype = AA   length = 227
FEATURE                    Location/Qualifiers
source                     1..227
                           mol_type = protein
```

```
                              organism = synthetic construct
SEQUENCE: 27
DKTHTCPPCP APELLGGPSV FLFPPKPKDT LMISRTPEVT CVVVDVSHED PEVKFNWYVD    60
GVEVHNAKTK PREEQYGSTY RVVSVLTVLH QDWLNGKEYK CKVSNKALPA PIEKTISKAK   120
GQPREPQVYT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLSPGK                 227

SEQ ID NO: 28             moltype = AA  length = 226
FEATURE                   Location/Qualifiers
source                    1..226
                          mol_type = protein
                          organism = synthetic construct
SEQUENCE: 28
DKTHTCPPCP APELLGGPSV FLFPPKPKDT LMISRTPEVT CVVVDVSHED PEVKFNWYVD    60
GVEVHNAKTK PREEQYGSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALHNHYTQKS LSLSPG                  226

SEQ ID NO: 29             moltype = AA  length = 425
FEATURE                   Location/Qualifiers
source                    1..425
                          mol_type = protein
                          organism = synthetic construct
SEQUENCE: 29
ANQVEQSPQS LIILEGKNVT LQCQYTVSPF SNLRWYKQDT GRGPVSLTIL TFSENTKSNG    60
RYTATLDADT KQSSLHITAS QLSDSASYIC VVNSAQGLYI PTFGRGTSLI VHPYIQKPDP   120
AVYQLRDSKS SDKSVCLFTD FDSQTQVSQS KDSDVYITDK CVLDMRSMDF KSNSAVAWSQ   180
KSDFACANAF QNSIIPEDTD KTHTCPPCPA PELLGGPSVF LFPPKPKDTL MISRTPEVTC   240
VVVDVSHEDP EVKFNWYVDG VEVHNAKTKP REEQYGSTYR VVSVLTVLHQ DWLNGKEYKC   300
KVSNKALPAP IEKTISKAKG QPREPQVYTL PPSRDELTKN QVSLSCAVKG FYPSDIAVEW   360
ESNGQPENNY KTTPPVLDSD GSFFLVSKLT VDKSRWQQGN VFSCSVMHEA LHNHYTQKSL   420
SLSPG                                                              425

SEQ ID NO: 30             moltype = AA  length = 504
FEATURE                   Location/Qualifiers
source                    1..504
                          mol_type = protein
                          organism = synthetic construct
SEQUENCE: 30
AIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIKGGG GSGGGGSGGG   120
GSGGGGSGGG SEVQLVESGG GLVQPGGSLR LSCAASGYSF TGYAMNWVRQ APGKGLEWVA   180
LINPYKGVST YNQKFKDRFT FSVDKSKNTA YLQMNSLRAE DTAVYYCARS GYYGDSDWYF   240
DVWGQGTLVT VSSGGGGSDV KVTQSSRYLV KRTGEKVFLE CVQDLDHENM FWYRQDPGLG   300
LRLIYFSRFA TGKEKGDIPE GYSVSREKKE RFSLILESAS TQQTSMYLCA SSSDQNSGDP   360
YEQYFGPGTR LTVTEDLKNV FPPEVAVFEP SEAEISHTQK ATLVCLATGF YPDHVELSWW   420
VNGKEVHSGV CTDPQPLKEQ PALQDSRYAL SSRLRVSATF WQDPRNHFRC QVFYGLSEN    480
DEWTQDRAKP VTQIVSAEAW GRAD                                         504

SEQ ID NO: 31             moltype = AA  length = 8
FEATURE                   Location/Qualifiers
source                    1..8
                          mol_type = protein
                          organism = synthetic construct
SEQUENCE: 31
DKTHTCPP                                                             8

SEQ ID NO: 32             moltype = AA  length = 113
FEATURE                   Location/Qualifiers
source                    1..113
                          mol_type = protein
                          organism = synthetic construct
SEQUENCE: 32
ANQVEQSPQS LIILEGKNVT LQCNYTVSPF SNLRWYKQDT GRGPVSLTIL TFSENTKSNG    60
RYTATLDADT KQSSLHITAS QLSDSASYIC VVNSAQGLYI PTFGRGTSLI VHP          113

SEQ ID NO: 33             moltype = AA  length = 116
FEATURE                   Location/Qualifiers
source                    1..116
                          mol_type = protein
                          organism = synthetic construct
SEQUENCE: 33
DVKVTQSSRY LVKRTGEKVF LECVQDLDHE NMFWYRQDPG LGLRLIYFSR FATGKEKGDI    60
PEGYSVSREK KERFSLILES ASTNQTSMYL CASSSDQNSG DPYEQYFGPG TRLTVT       116

SEQ ID NO: 34             moltype = AA  length = 10
FEATURE                   Location/Qualifiers
source                    1..10
                          mol_type = protein
```

```
                        organism = synthetic construct
SEQUENCE: 34
GVYDGREHTV                                                         10

SEQ ID NO: 35           moltype = AA  length = 253
FEATURE                 Location/Qualifiers
source                  1..253
                        mol_type = protein
                        organism = synthetic construct
SEQUENCE: 35
AIQMTQSPSS LSASVGDRVT ITCRASQDIR NYLNWYQQKP GKAPKLLIYY TSRLESGVPS   60
RFSGSGSGTD YTLTISSLQP EDFATYYCQQ GNTLPWTFGQ GTKVEIKGGG GSGGGGSGGG  120
GSGGGGSGGG SEVQLVESGG GLVQPGGSLR LSCAASGYSF TGYTMNWVRQ APGKGLEWVA  180
LINPYKGVST YNQKFKDRFT ISVDKSKNTA YLQMNSLRAE DTAVYYCARS GYYGDSDWYF  240
DVWGQGTLVT VSS                                                    253

SEQ ID NO: 36           moltype = AA  length = 9
FEATURE                 Location/Qualifiers
source                  1..9
                        mol_type = protein
                        organism = Synthetic construct
SEQUENCE: 36
DKTHTCPPC                                                          9
```

What is claimed is:

1. A T cell receptor (TCR) fusion protein comprising a TCR that binds to GVYDGREHTV (SEQ ID NO: 34) HLA-A*02 complex, wherein the TCR fusion protein comprises a first polypeptide comprising the amino acid sequence of SEQ ID NO:29, a second polypeptide comprising the amino acid sequence of SEQ ID NO:30, and a third polypeptide comprising the amino acid sequence of SEQ ID NO:28.

2. A polynucleotide encoding the TCR fusion protein according to claim 1.

3. A kit of polynucleotides encoding the TCR fusion protein according to claim 1, wherein the kit comprises a first polynucleotide encoding the first polypeptide, a second polynucleotide encoding the second polypeptide, and a third polynucleotide encoding the third polypeptide.

4. A vector comprising the polynucleotide of claim 2.

5. A kit of vectors encoding the TCR fusion protein according to claim 1, wherein the kit comprises a first vector encoding the first polypeptide, a second vector encoding the second polypeptide, and a third vector encoding the third polypeptide.

6. A host cell comprising the polynucleotide of claim 2.

7. The host cell of claim 6, wherein the host cell is a mammalian cell.

8. The host cell of claim 7, wherein the mammalian cell is a Chinese hamster ovary (CHO) cell.

9. A method of producing a TCR fusion protein, comprising culturing the host cell of claim 6 under conditions suitable for production of the TCR fusion protein.

10. The method of claim 9, further comprising recovering the TCR fusion protein from the host cell.

11. A TCR fusion protein produced by the method of claim 9.

12. A pharmaceutical composition comprising the TCR fusion protein according to claim 1 and a pharmaceutically acceptable carrier.

13. A method of treating cancer, comprising administering an effective amount of the pharmaceutical composition of claim 12 to an individual.

14. The method of claim 13, wherein the individual is a human.

15. The method of claim 14, wherein the individual has a cancer that expresses MAGE-A4.

16. The method of claim 14, wherein the individual is of HLA-A*02 subtype.

17. The method of claim 13, wherein the composition is administered intravenously or by intratumoral injection.

18. The method of claim 13, further comprising administering to the individual a second anti-cancer agent.

19. The fusion protein of claim 1, wherein the TCR fusion protein is glycosylated at a single N-linked glycosylation site at residue N18 of the first polypeptide, numbering according to SEQ ID NO:29.

20. The fusion protein of claim 1, wherein the first and third polypeptides are linked via one or more disulfide bonds.

21. The fusion protein of claim 1, wherein the first and second polypeptides are linked via one or more disulfide bonds.

* * * * *